US010864196B2

(12) United States Patent
Pliushchev et al.

(10) Patent No.: US 10,864,196 B2
(45) Date of Patent: Dec. 15, 2020

(54) MODULATORS OF THE INTEGRATED STRESS PATHWAY

(71) Applicants: Calico Life Sciences LLC, South San Francisco, CA (US); AbbVie Inc., North Chicago, IL (US)

(72) Inventors: Marina Pliushchev, Vernon Hills, IL (US); Jennifer M. Frost, Gurnee, IL (US); Lawrence A. Black, Lahaina, HI (US); Xiangdong Xu, Vernon Hills, IL (US); Ramzi Farah Sweis, Vernon Hills, IL (US); Lei Shi, Vernon Hills, IL (US); Qingwei I. Zhang, Libertyville, IL (US); Yunsong Tong, Libertyville, IL (US); Charles W. Hutchins, Green Oaks, IL (US); Seungwon Chung, Libertyville, IL (US); Michael J. Dart, Highland Park, IL (US)

(73) Assignees: Calico Life Sciences, LLC, South San Francisco, CA (US); AbbVie Inc., North Chicago, IL (US)

( * ) Notice: Subject to any disclaimer, the term of this patent is extended or adjusted under 35 U.S.C. 154(b) by 0 days.

(21) Appl. No.: 16/098,950

(22) PCT Filed: May 5, 2017

(86) PCT No.: PCT/US2017/031352
§ 371 (c)(1),
(2) Date: Nov. 5, 2018

(87) PCT Pub. No.: WO2017/193030
PCT Pub. Date: Nov. 9, 2017

(65) Prior Publication Data
US 2019/0142806 A1 May 16, 2019

Related U.S. Application Data

(60) Provisional application No. 62/332,284, filed on May 5, 2016.

(51) Int. Cl.
| | | |
|---|---|---|
| C07D 413/12 | (2006.01) |
| A61K 31/42 | (2006.01) |
| C07D 271/10 | (2006.01) |
| C07D 471/04 | (2006.01) |
| C07D 271/06 | (2006.01) |
| C07D 401/12 | (2006.01) |
| C07D 233/64 | (2006.01) |
| A61P 3/08 | (2006.01) |
| A61P 25/28 | (2006.01) |
| A61P 9/00 | (2006.01) |
| A61P 35/00 | (2006.01) |

(52) U.S. Cl.
CPC ............ *A61K 31/42* (2013.01); *A61P 3/08* (2018.01); *A61P 9/00* (2018.01); *A61P 25/28* (2018.01); *A61P 35/00* (2018.01); *C07D 233/64* (2013.01); *C07D 271/06* (2013.01); *C07D 271/10* (2013.01); *C07D 401/12* (2013.01); *C07D 413/12* (2013.01); *C07D 471/04* (2013.01)

(58) Field of Classification Search
CPC .................................................. C07D 413/12
See application file for complete search history.

(56) References Cited

U.S. PATENT DOCUMENTS

| | | |
|---|---|---|
| 7,994,211 B2 | 8/2011 | Ray et al. |
| 2004/0133011 A1 | 7/2004 | Waddell et al. |
| 2006/0149070 A1 | 7/2006 | Rohde et al. |
| 2007/0185079 A1 | 8/2007 | Evertsson et al. |
| 2015/0057289 A1 | 2/2015 | Li et al. |
| 2016/0096800 A1 | 4/2016 | Walter et al. |

FOREIGN PATENT DOCUMENTS

| | | | |
|---|---|---|---|
| WO | WO-2011/087758 A1 | 7/2011 |
| WO | WO-2012/088365 A1 | 6/2012 |
| WO | WO-2014/144952 A2 | 9/2014 |
| WO | WO-2015/038778 A1 | 3/2015 |
| WO | WO-2017223275 A1 * | 12/2017 | ......... A61K 47/6883 |

OTHER PUBLICATIONS

André et al. "(S)-ABOC: A Rigid Bicyclic β-Amino Acid as Turn Inducer" Organic Letters (2012) vol. 14(4), pp. 960-963.
Database PubChem Compound [Online] Jul. 10, 2005, retrieved from NCBI, Database accession No. 1300563.
Database PubChem Compound [Online] Nov. 13, 2007, retrieved from NCBI, Database accession No. 17565335.
Database PubChem Compound [Online] Dec. 5, 2007, retrieved from NCBI, Database accession No. 20755106.
Database PubChem Compound [Online] Nov. 15, 2010, retrieved from NCBI, Database accession No. 46939935.
Database PubChem Compound [Online] Nov. 15, 2010, retrieved from NCBI, Database accession No. 46939936.
Database PubChem Compound [Online] May 3, 2011, retrieved from NCBI, Database accession No. 51064332.
Database PubChem Compound [Online] Nov. 30, 2012, retrieved from NCBI, Database accession No. 66910924.
Database PubChem Compound [Online] Nov. 30, 2012, retrieved from NCBI, Database accession No. 66910946.
Database PubChem Compound [Online] Nov. 30, 2012, retrieved from NCBI, Database accession No. 66910949.
Database PubChem Compound [Online] Nov. 30, 2012, retrieved from NCBI, Database accession No. 68048074.
Database PubChem Compound [Online] Dec. 1, 2012, retrieved from NCBI, Database accession No. 69612403.
Database PubChem Compound [Online] Mar. 23, 2015, retrieved from NCBI, Database accession No. 91663862.

(Continued)

*Primary Examiner* — John S Kenyon
(74) *Attorney, Agent, or Firm* — Goodwin Procter LLP

(57) ABSTRACT

Provided herein are compounds, compositions, and methods useful for modulating the integrated stress response (ISR) and for treating related diseases; disorders and conditions.

22 Claims, No Drawings

(56) References Cited

OTHER PUBLICATIONS

Database PubChem Compound [Online] Dec. 11, 2015, retrieved from NCBI, Database accession No. 98260962.
Database PubChem Compound [Online] Dec. 18, 2015, retrieved from NCBI, Database accession No. 101566942.
Database PubChem Compound [Online] Feb. 23, 2016, retrieved from NCBI, Database accession No. 118417886.
Fogli and Boespflug-Tanguy "The large spectrum of eIF2B-related diseases" Biochemical Society Transactions (2006) vol. 34, pp. 22-29.
Font et a. "Structural characteristics of novel symmetrical diaryl derivatives with nitrogenated functions. Requirements for cytotoxic activity" Bioorganic & Medicinal Chemistry (2006) vol. 14, pp. 1942-1948.
International Search Report and Written Opinion dated Jul. 10, 2017 for Application No. PCT/US2017/031352 (12 pages).
International Search Report and Written Opinion dated Jun. 26, 2017 for Application No. PCT/US2017/031360 (16 pages).
International Search Report and Written Opinion dated Jun. 26, 2017 for Application No. PCT/US2017/031367 (13 pages).
International Search Report and Written Opinion dated Jul. 3, 2017 for Application No. PCT/US2017/031393 (13 pages).
Patel et al. "Discovery of adamantine ethers as inhibitors of 11β-HSD-1: Synthesis and biological evaluation" Bioorganic & Medicinal Chemistry Letters (2007) vol. 17, pp. 750-755.
Smith et al. "Norbornyl Dipeptide Analogues: Mimics of Both a Transition State and a Torsionally Distorted Ground State" Bioorganic Chemistry (1995) vol. 23, pp. 397-414.

\* cited by examiner

MODULATORS OF THE INTEGRATED STRESS PATHWAY

CROSS REFERENCE TO RELATED APPLICATIONS

This application is a national stage filing under U.S.C. § 371 of PCT/US2017/031352, filed on May 5, 2017, which claims the benefit of, and priority to, U.S. provisional application No. 62/332,284, filed May 5, 2016, the content of each of which is hereby incorporated by reference in its entirety.

BACKGROUND

In metazoa, diverse stress signals converge at a single phosphorylation event at serine 51 of a common effector, the translation initiation factor eIF2α. This step is carried out by four eIF2α kinases in mammalian cells: PERK, which responds to an accumulation of unfolded proteins in the endoplasmic reticulum (ER), GCN2 to amino acid starvation and UV light, PKR to viral infection and metabolic stress, and HRI to heme deficiency. This collection of signaling pathways has been termed the "integrated stress response" (ISR), as they converge on the same molecular event. eIF2α phosphorylation results in an attenuation of translation with consequences that allow cells to cope with the varied stresses (Wek, R. C. et al, *Biochem Soc Trans* (2006) 34(Pt 1):7-11).

eIF2 (which is comprised of three subunits, α, β and γ) binds GTP and the initiator Met-tRNA to form the ternary complex (eIF2-GTP-Met-tRNA$_i$), which, in turn, associates with the 40S ribosomal subunit scanning the 5'UTR of mRNAs to select the initiating AUG codon. Upon phosphorylation of its α-subunit, eIF2 becomes a competitive inhibitor of its GTP-exchange factor (GEF), eIF2B (Hinnebusch, A. G. and Lorsch, J. R. *Cold Spring Harbor Perspect Biol* (2012) 4(10)). The tight and nonproductive binding of phosphorylated eIF2 to eIF2B prevents loading of the eIF2 complex with GTP, thus blocking ternary complex formation and reducing translation initiation (Krishnamoorthy, T. et al, *Mol Cell Biol* (2001) 21(15):5018-5030). Because eIF2B is less abundant than eIF2, phosphorylation of only a small fraction of the total eIF2 has a dramatic impact on eIF2B activity in cells.

eIF2B is a complex molecular machine, composed of five different subunits, eIF2B1 through eIF2B5. eIF2B5 catalyzes the GDP/GTP exchange reaction and, together with a partially homologous subunit eIF2B3, constitutes the "catalytic core" (Williams, D. D. et al, *J Biol Chem* (2001) 276:24697-24703). The three remaining subunits (eIF2B1, eIF2B2, and eIF2B4) are also highly homologous to one another and form a "regulatory sub-complex" that provides binding sites for eIF2B's substrate eIF2 (Dev, K. et al, *Mol Cell Biol* (2010) 30:5218-5233). The exchange of GDP with GTP in eIF2 is catalyzed by its dedicated guanine nucleotide exchange factor (GEF) eIF2B. eIF2B exists as a decamer (B1$_2$ B2$_2$ B3$_2$ B4$_2$ B5$_2$) or dimer of two pentamers in cells (Gordiyenko, Y. et al, *Nat Commun* (2014) 5:3902; Wortham, N.C. et al, *FASEB J* (2014) 28:2225-2237). Molecules such as ISRIB interact with and stabilize the eIF2B dimer conformation, thereby enhancing intrinsic GEF activity and making cells less sensitive to the cellular effects of phosphorylation of eIF2α (Sidrauski, C. et al, *eLife* (2015) e07314; Sekine, Y. et al, *Science* (2015) 348:1027-1030). As such, small molecule therapeutics that can modulate eIF2B activity may have the potential to attenuate the PERK branch of the UPR and the overall ISR, and therefore may be used in the prevention and/or treatment of various diseases, such as a neurodegenerative disease, a leukodystrophy, cancer, an inflammatory disease, a musculoskeletal disease, or a metabolic disease.

SUMMARY OF THE INVENTION

The present invention features compounds, compositions, and methods for the modulation of eIF2B (e.g., activation of eIF2B) and the attenuation of the ISR signaling pathway. In some embodiments, the present invention features an eIF2B modulator (e.g., an eIF2B activator) comprising a compound of Formula (I) or a pharmaceutically acceptable salt, solvate, hydrate, tautomer, or stereoisomer thereof. In other embodiments, the present invention features methods of using a compound of Formula (I) or a pharmaceutically acceptable salt, solvate, hydrate, tautomer, or stereoisomer thereof for the treatment of a disease or disorder, e.g., a neurodegenerative disease, a leukodystrophy, cancer, an inflammatory disease, a musculoskeletal disease, a metabolic disease, or a disease or disorder associated with impaired function of eIF2B or components in the ISR pathway (e.g., eIF2 pathway).

In one aspect, the present invention features a compound of Formula (I):

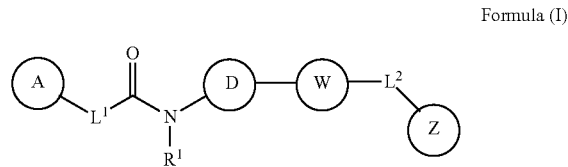

Formula (I)

or a pharmaceutically acceptable salt, solvate, hydrate, tautomer, or stereoisomer thereof, wherein D is a bridged monocyclic cycloalkyl, bridged monocyclic heterocyclyl, or cubanyl, wherein each bridged monocyclic cycloalkyl, bridged monocyclic heterocyclyl, or cubanyl is optionally substituted with 1-4 $R^X$; $L^1$ and $L^2$ are each independently $C_1$-$C_6$ alkylene, 2-7 membered heteroalkylene, or —O—, wherein each $C_1$-$C_6$ alkylene or 2-7 membered heteroalkylene is optionally substituted with 1-5 $R^X$; $R^1$ is hydrogen or $C_1$-$C_6$ alkyl; A and W are each independently phenyl or 5-6-membered heteroaryl, wherein each phenyl or 5-6-membered heteroaryl is optionally substituted with 1-5 $R^Y$; Z is hydrogen, phenyl, or 5-6-membered heteroaryl, wherein each phenyl or 5-6-membered heteroaryl is optionally substituted with 1-5 $R^Y$; each $R^X$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, —$SR^E$, —$S(O)R^D$, and —$S(O)_2R^D$; each $R^Y$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, —$S(R^F)_m$, —$S(O)R^D$, —$S(O)_2R^D$, and $G^1$; or 2 $R^Y$ groups on adjacent atoms, together with the atoms to which they are attached form a 3-7-membered fused cycloalkyl, 3-7-membered fused heterocyclyl, aryl, or 5-6 membered fused heteroaryl optionally substituted with 1-5 $R^X$; each $G^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 $R^Z$; each $R^Z$ is independently selected from the group consisting of $C_1$-$C_6$ alkyl, hydroxy-$C_1$-$C_6$ alkyl, halo-$C_1$-$C_6$ alkyl, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, and —$S(O)_2R^D$; $R^A$ is, at each occurrence, independently hydrogen, $C_1$-$C_6$ alkyl, halo-$C_1$-$C_6$ alkyl, —$C(O)NR^BR^C$, —$C(O)R^D$, —$C(O)OH$, or —$C(O)OR^D$; each of $R^B$ and $R^C$ is independently hydrogen or $C_1$-$C_6$ alkyl; or $R^B$ and $R^C$ together with the atom to which they are attached form a 3-7-membered heterocyclyl ring optionally substituted with 1-3 $R^Z$; each $R^D$ is independently $C_1$-$C_6$ alkyl or halo-$C_1$-$C_6$ alkyl; each $R^E$ is independently hydrogen $C_1$-$C_6$ alkyl, or halo-$C_1$-$C_6$ alkyl; each $R^F$ is independently hydrogen, $C_1$-$C_6$ alkyl, or halo; and m is 1, 3, or 5.

In some embodiments, D is a bridged monocyclic cycloalkyl optionally substituted with 1-4 $R^X$. In some embodiments, D is a bridged 4-6 membered cycloalkyl optionally substituted with 1-4 $R^X$. In some embodiments, D is bicyclo[1.1.1]pentane, bicyclo[2.2.1]heptane, bicyclo[2.1.1]hexane, or bicyclo[2.2.2]octane, each of which is optionally substituted with 1-4 $R^X$ groups. In some embodiments, D is bicyclo[1.1.1]pentane or bicyclo[2.2.2]octane, each of which is optionally substituted with 1-4 $R^X$ groups. In some embodiments, D is

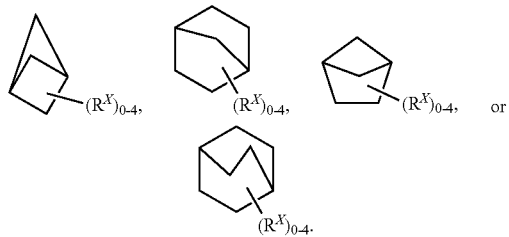

In some embodiments, D is

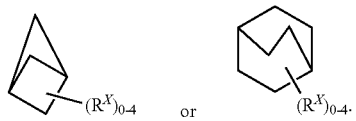

In some embodiments, D is

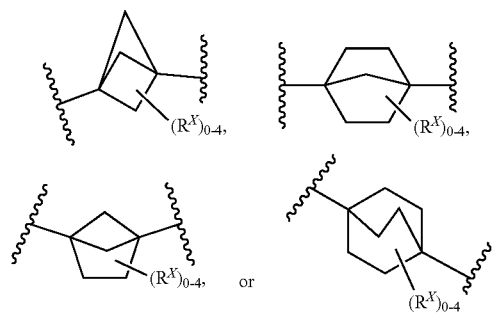

In some embodiments, D is

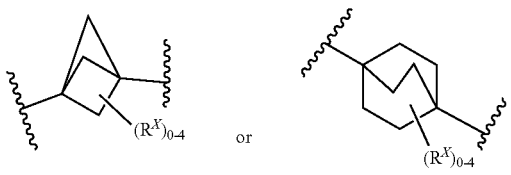

In some embodiments, D is substituted with 0 $R^X$. In some embodiments, D is

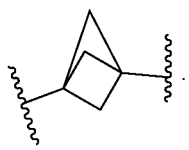 [SMILES: *C12CC(*)(C1)C2 ; "."]

In some embodiments, D is substituted with 1 $R^X$. In some embodiments, D is

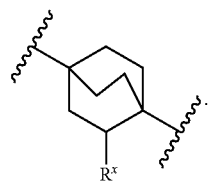

In some embodiments, $R^X$ is oxo or —$OR^A$(e.g., oxo or OH). In some embodiments, D is

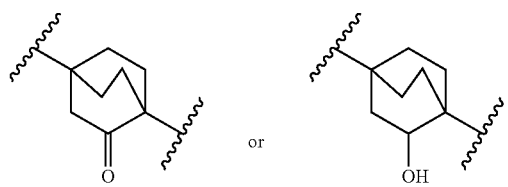

In some embodiments, both of $L^1$ and $L^2$ are independently 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is substituted by 0 $R^X$. In some embodiments, each $L^1$ and $L^2$ is independently selected from $CH_2O$—*, $CH_2OCH_2$—*, or —O—, and "-*" indicates the attachment point to A or Z, respectively. In some embodiments, $L^1$ is $CH_2O$—* or $CH_2OCH_2$—*, $L^2$ is selected from $CH_2O$—*, $CH_2O$-$CH_2$—*, or —O—, and "-*" indicates the attachment point to A or Z, respectively. In some embodiments, $L^1$ is $CH_2O$—* or $CH_2OCH_2$—*, $L^2$ is selected from $CH_2O$—* or —O—, and "-*" indicates the attachment point to A or Z, respectively.

In some embodiments, $R^1$ is hydrogen.

In some embodiments, each A and W is independently phenyl or 5-6-membered heteroaryl and Z is hydrogen, phenyl, or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A, W, and Z is independently phenyl, pyridyl, oxadiazolyl, imidazolyl, triazolyl, or isoxazolyl, each of which is optionally substituted with 1-5 $R^Y$ groups. In some embodiments, each of A, W, and Z is independently phenyl, pyridyl, oxadiazolyl, triazolyl, or isoxazolyl, each of which is optionally substituted with 1-5 $R^Y$ groups.

In some embodiments, each of A, W, and Z is selected from:

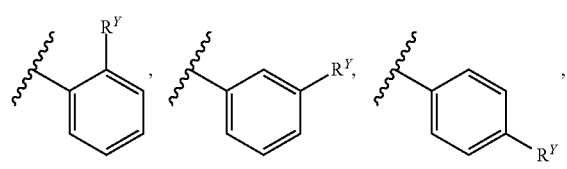

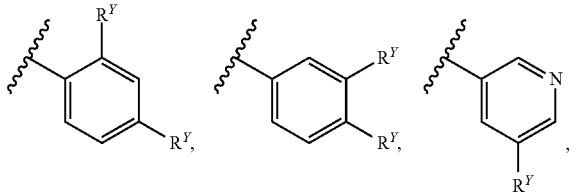

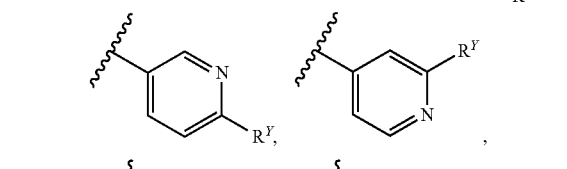

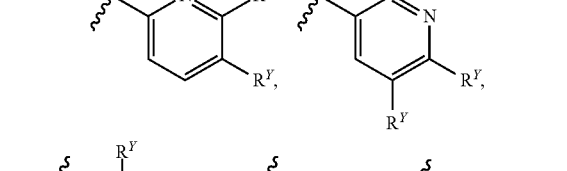

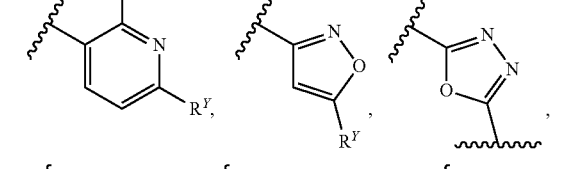

In some embodiments, each of A, W, and Z is selected from:

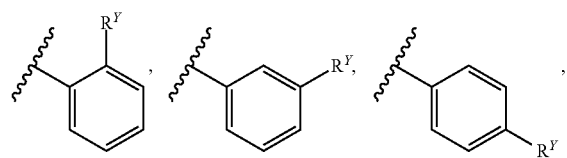

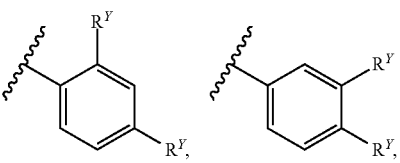

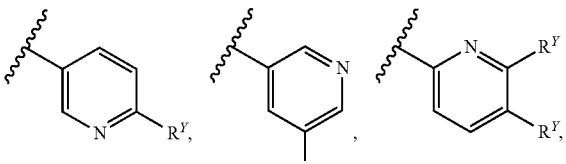

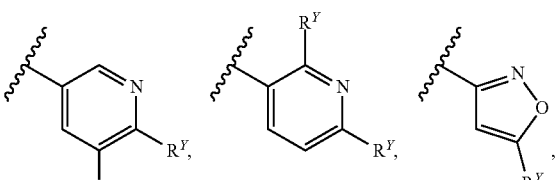

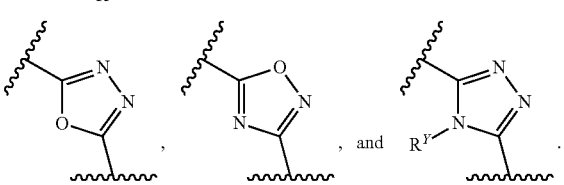

, and

In some embodiments, A is phenyl, pyridyl, or isoxazolyl, each of which is optionally substituted with 1-2 $R^Y$ groups. In some embodiments, A is selected from:

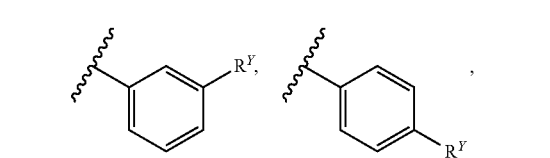

In some embodiments, A is phenyl optionally substituted with 1-2 $R^Y$ groups. In some embodiments, A is selected from:

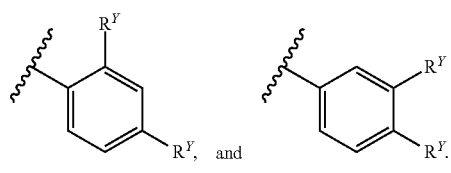

In some embodiments, W is oxadiazolyl, imidazolyl, or triazolyl. In some embodiments, W is selected from:

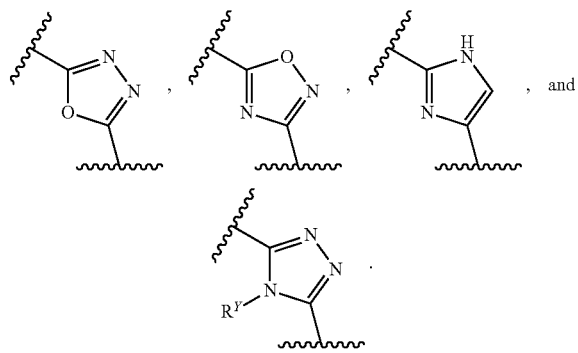

In some embodiments, W is oxadiazolyl or triazolyl. In some embodiments, W is selected from:

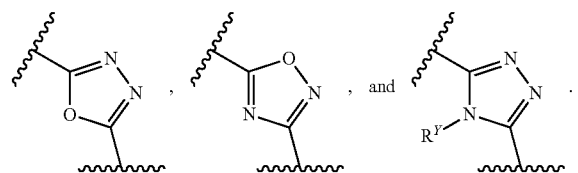

In some embodiments, Z is hydrogen, phenyl or pyridyl. In some embodiments, Z is hydrogen. In some embodiments, Z is phenyl or pyridyl, each of which is optionally substituted with 1-2 $R^Y$ groups. In some embodiments, Z is selected from:

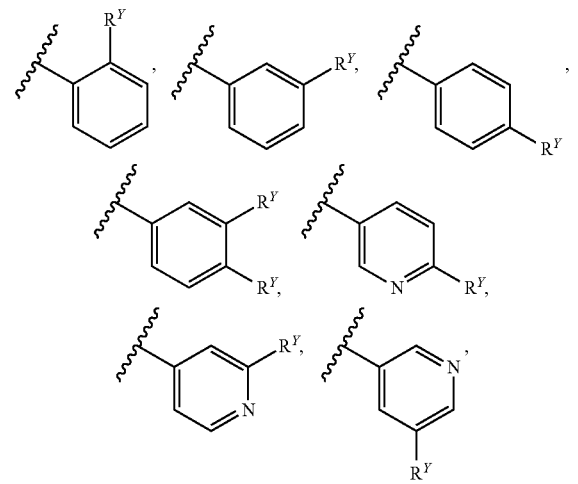

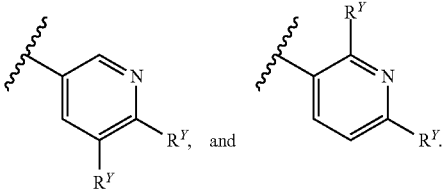

In some embodiments, A is phenyl, pyridyl, or isoxazolyl, W is oxadiazolyl, imidazolyl, or triazolyl, and Z is phenyl or pyridyl, wherein each phenyl, pyridyl, oxadiazolyl, imidazolyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, A is phenyl, pyridyl, or isoxazolyl, W is oxadiazolyl or triazolyl, and Z is phenyl or pyridyl, wherein each phenyl, pyridyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, each A and Z is independently substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, A is substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, Z is substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) is a compound of Formula (I-a):

Formula (I-a)

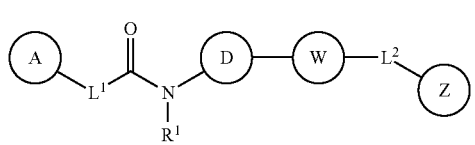

or a pharmaceutically acceptable salt, solvate, hydrate, tautomer, or stereoisomer thereof, wherein D is bicyclo[1.1.1]pentanyl, each of which is optionally substituted with 1-4 $R^X$ groups; $L^1$ and $L^2$ are each independently $CH_2O$—*, $CH_2OCH_2$—*, or —O—, and "-*" indicates the attachment point to A or Z, respectively; $R^1$ is hydrogen; A and W are each independently phenyl, pyridyl, oxadiazolyl, imidazolyl, triazolyl, or isoxazolyl, each of which is optionally substituted with 1-5 $R^Y$ groups; Z is hydrogen, phenyl, or pyridyl, wherein each phenyl or pyridyl is optionally substituted with 1-5 $R^Y$ groups; each $R^X$ is fluoro, oxo, or OH; each $R^Y$ is independently chloro, fluoro, $CF_3$, $CH_3$, $CH_2CH_3$, $CH(CH_3)_2$, $OCH_3$, $OCH(CH_3)_2$, CN, or $G^1$; or 2 $R^Y$ groups on adjacent atoms, together with the atoms to which they are attached form a furanyl, pyrrolyl, or dioxolanyl ring, each of which is optionally substituted with 1-2 $R^X$; and $G^1$ is cyclopropyl.

In some embodiments, the compound of Formula (I) is a compound of Formula (I-b):

Formula (I-b)

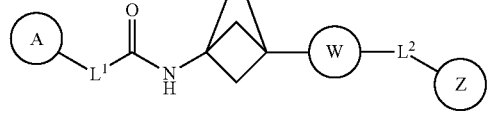

or a pharmaceutically acceptable salt, solvate, hydrate, tautomer, or stereoisomer thereof, wherein each of A, W, Z, $L^1$, and $L^2$ is defined as for Formula (I).

In some embodiments, the compound of Formula (I) is a compound of Formula (I-c):

Formula (I-c)

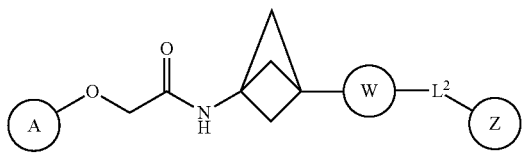

or a pharmaceutically acceptable salt, solvate, hydrate, tautomer, or stereoisomer thereof, wherein each of A, W, Z, and $L^2$ is defined as for Formula (I).

In some embodiments, the compound of Formula (I) is a compound of Formula (I-d):

Formula (I-d)

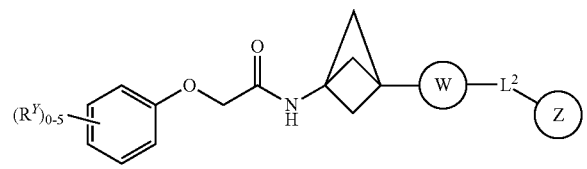

or a pharmaceutically acceptable salt, solvate, hydrate, tautomer, or stereoisomer thereof, wherein each of W, Z, $L^2$, and $R^Y$ is defined as for Formula (I).

In some embodiments, the compound of Formula (I) is a compound of Formula (I-e-1), Formula (I-e-2), Formula (I-e-3), Formula (I-e-4), or Formula (I-e-5):

Formula (I-e-1)

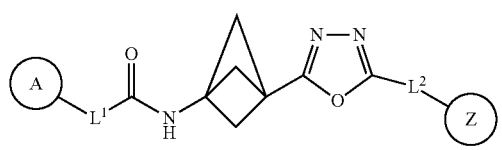

Formula (I-e-2)

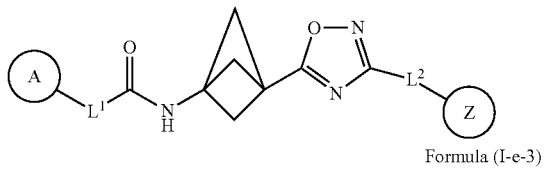

Formula (I-e-3)

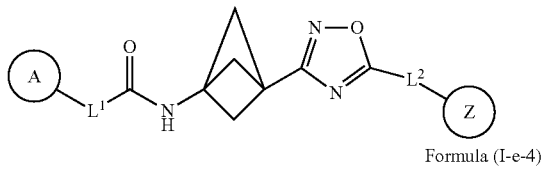

Formula (I-e-4)

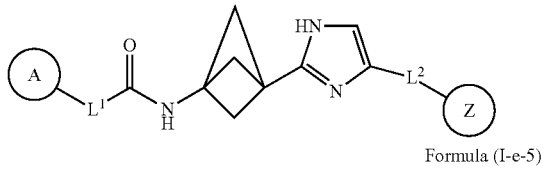

Formula (I-e-5)

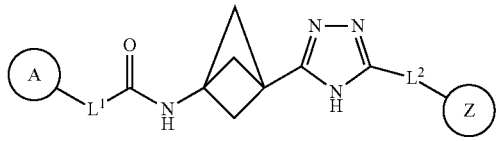

or a pharmaceutically acceptable salt, solvate, hydrate, tautomer, or stereoisomer thereof, wherein each of A, Z, $L^1$, and $L^2$ is defined as for Formula (I).

In some embodiments, the compound of Formula (I) is a compound of Formula (I-f):

Formula (I-f)

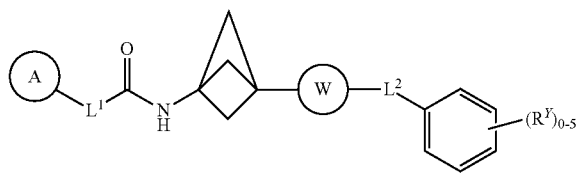

or a pharmaceutically acceptable salt, solvate, hydrate, tautomer, or stereoisomer thereof, wherein each of A, W, $L^1$, $L^2$, and $R^Y$ is defined as for Formula (I).

In some embodiments, the compound of Formula (I) is a compound of Formula (I-g):

Formula (I-g)

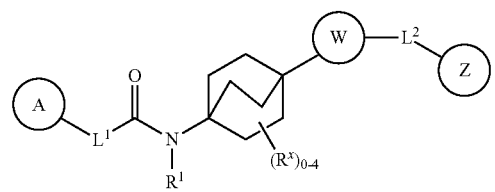

or a pharmaceutically acceptable salt, solvate, hydrate, tautomer, or stereoisomer thereof, wherein each of A, W, Z, $L^1$, $L^2$, and $R^X$ is defined as for Formula (I).

In some embodiments, the compound is selected from any compound set forth in Table 1 or a pharmaceutically acceptable salt, solvate, hydrate, tautomer, or stereoisomer thereof.

In some embodiments, the compound of Formula (I) (e.g., a compound of Formula (I-a), (I-b), (I-c), (I-d), (I-e-1), (I-e-2), (I-e-3), (I-e-4), (I-e-5), (I-f), or (I-g)) or a pharmaceutically acceptable salt thereof is formulated as a pharmaceutically acceptable composition comprising a compound of any one of the preceding claims and a pharmaceutically acceptable carrier.

In another aspect, the present invention features a method of treating a neurodegenerative disease, a leukodystrophy, cancer, an inflammatory disease, a musculoskeletal disease, a metabolic disease, or a disease or disorder associated with impaired function of eIF2B or components in the ISR pathway (e.g., eIF2 pathway) in a subject, wherein the method comprises administering a compound of Formula (I) or a pharmaceutically acceptable salt, solvate, hydrate, tautomer, or stereoisomer thereof, or a composition thereof, to a subject.

In some embodiments, the method comprises the treatment of a neurodegenerative disease. In some embodiments, the neurodegenerative disease comprises vanishing white matter disease, childhood ataxia with CNS hypo-myelination, a leukodystrophy, a leukoencephalopathy, hypomyelinating or demyelinating disease, an intellectual disability syndrome, Alzheimer's disease, amyotrophic lateral sclerosis, Creutzfeldt-Jakob disease, Frontotemporal dementia, Gerstmann-Straussler-Scheinker disease, Huntington's disease, dementia (e.g., HIV-associated dementia or Lewy body dementia), Kuru, Parkinson's disease, progressive nuclear palsy, a tauopathy, or a prion disease. In some embodiments, the neurodegenerative disease comprises vanishing white matter disease. In some embodiments, the neurodegenerative disease comprises a psychiatric disease such as agoraphobia, Alzheimer's disease, anorexia nervosa, amnesia, anxiety disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania. In some embodiments, the neurodegenerative disease comprises a disease or disorder with symptoms of cognitive impairment or cognitive decline such as Alzheimer's disease, Parkinson's disease, Huntington's disease, schizophrenia, autism, frontotemporal dementia, dementia (e.g., HIV-associated dementia or Lewy body dementia), age related dementia, chronic traumatic encephalopathy, HIV-induced neurocognitive impairment, a HIV-associated neurocognitive disorder, a hypoxic injury (e.g., premature brain injury, chronic perinatal hypoxia), traumatic brain injury, or postoperative cognitive dysfunction. In some embodiments, the neurodegenerative disease comprises an intellectual disability syndrome. In some embodiments, the neurodegenerative disease comprises mild cognitive impairment.

In some embodiments, the method comprises the treatment of cancer. In some embodiments, the cancer comprises pancreatic cancer, breast cancer, multiple myeloma, or a cancer of the secretory cells. In some embodiments, the method comprises the treatment of cancer in combination with a chemotherapeutic agent for the enhancement of memory (e.g., long term memory).

In some embodiments, the method comprises the treatment of an inflammatory disease. In some embodiments, the inflammatory disease comprises postoperative cognitive dysfunction, traumatic brain injury, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, or atopic dermatitis.

In some embodiments, the method comprises the treatment of a musculoskeletal disease. In some embodiments, the musculoskeletal disease comprises muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, or paralysis.

In some embodiments, the method comprises the treatment of a metabolic disease. In some embodiments, the metabolic disease comprises non-alcoholic steatohepatitis (NASH), non-alcoholic fatty liver disease (NAFLD), liver fibrosis, obesity, heart disease, atherosclerosis, arthritis, cystinosis, phenylketonuria, proliferative retinopathy, or Kearns-Sayre disease.

In another aspect, the present invention features a method of treating a disease or disorder related to modulation (e.g., a decrease) in eIF2B activity or level, modulation (e.g., a decrease) of eIF2α activity or level, modulation (e.g., an increase) in eIF2α phosphorylation, modulation (e.g., an increase) of phosphorylated eIF2α pathway activity, or modulation (e.g., an increase) of ISR activity in a subject, wherein the method comprises administering a compound of Formula (I) or a pharmaceutically acceptable salt, solvate, hydrate, tautomer, or stereoisomer thereof, or a composition thereof, to a subject. In some embodiments, the disease may be caused by a mutation to a gene or protein sequence related to a member of the eIF2 pathway (e.g., the eIF2α signaling pathway or ISR pathway).

In another aspect, the present invention features a method of treating a leukodystrophy such as vanishing white matter disease (VWMD) or childhood ataxia with central nervous system hypomyelination. In some embodiments, the leukodystrophy is characterized by an amino acid mutation (e.g., an amino acid deletion, amino acid addition, or amino acid substitution) in a tRNA synthetase. In some embodiments, administration of a compound of Formula (I) enhances eIF2B activity in a subject with a leukodystrophy, such as vanishing white matter disease (VWMD) or childhood ataxia with central nervous system hypomyelination.

In another aspect, the present invention features a method of treating a disease or disorder related to an amino acid mutation (e.g., an amino acid deletion, amino acid addition, or amino acid substitution) in a gene or gene product (e.g., RNA or protein) that modulates (e.g., reduces) protein synthesis. In some embodiments, administration of a compound of Formula (I) enhances residual GEF activity of a mutant GEF complex in a subject.

In another aspect, the present invention features a composition for use in treating a neurodegenerative disease, a leukodystrophy, cancer, an inflammatory disease, a musculoskeletal disease, or a metabolic disease in a subject, wherein the composition comprises a compound of Formula (I) or a pharmaceutically acceptable salt, solvate, hydrate, tautomer, or stereoisomer thereof.

In some embodiments, the neurodegenerative disease comprises vanishing white matter disease, childhood ataxia with CNS hypo-myelination, a leukodystrophy, a leukoencephalopathy, hypomyelinating or demyelinating disease, an intellectual disability syndrome, Alzheimer's disease, amyotrophic lateral sclerosis, Creutzfeldt-Jakob disease, Frontotemporal dementia, Gerstmann-Straussler-Scheinker disease, Huntington's disease, dementia (e.g., HIV-associated dementia or Lewy body dementia), Kuru, Parkinson's disease, progressive nuclear palsy, a tauopathy, or a prion disease. In some embodiments, the neurodegenerative disease comprises vanishing white matter disease. In some embodiments, the neurodegenerative disease comprises a psychiatric disease such as agoraphobia, Alzheimer's disease, anorexia nervosa, amnesia, anxiety disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania. In some embodiments, the neurodegenerative disease comprises a disease or disorder with symptoms of cognitive impairment or cognitive decline such as Alzheimer's disease, Parkinson's disease, Huntington's disease, schizophrenia, autism, frontotemporal dementia, dementia (e.g., HIV-associated dementia or Lewy body dementia), age related dementia, chronic traumatic encephalopathy, HIV-induced neurocognitive impairment, a HIV-associated neurocognitive disorder, a hypoxic injury (e.g., premature brain injury, chronic perinatal hypoxia), traumatic brain injury, or postoperative cognitive dysfunction. In some embodiments, the neurodegenerative disease comprises an intellectual disability syndrome. In some embodiments, the neurodegenerative disease comprises mild cognitive impairment.

In some embodiments, the cancer comprises pancreatic cancer, breast cancer, multiple myeloma, or a cancer of the secretory cells. In some embodiments, the method comprises the treatment of cancer in combination with a chemotherapeutic agent for the enhancement of memory (e.g., long term memory).

In some embodiments, the inflammatory disease comprises postoperative cognitive dysfunction, traumatic brain injury, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, or atopic dermatitis.

In some embodiments, the musculoskeletal disease comprises muscular dystrophy, multiple sclerosis, Freidrich's ataxia, a muscle wasting disorder (e.g., muscle atrophy, sarcopenia, cachexia), inclusion body myopathy, progressive muscular atrophy, motor neuron disease, carpal tunnel syndrome, epicondylitis, tendinitis, back pain, muscle pain, muscle soreness, repetitive strain disorders, or paralysis.

In some embodiments, the metabolic disease comprises non-alcoholic steatohepatitis (NASH), non-alcoholic fatty liver disease (NAFLD), liver fibrosis, obesity, heart disease, atherosclerosis, arthritis, cystinosis, phenylketonuria, proliferative retinopathy, or Kearns-Sayre disease.

In another aspect, the present invention features a composition for use in treating a disease or disorder related to modulation (e.g., a decrease) in eIF2B activity or level, modulation (e.g., a decrease) of eIF2α activity or level, modulation (e.g., an increase) in eIF2α phosphorylation, modulation (e.g., an increase) of phosphorylated eIF2α pathway activity, or modulation (e.g., an increase) of ISR activity in a subject, wherein the composition comprises a compound of Formula (I) or a pharmaceutically acceptable salt, solvate, hydrate, tautomer, or stereoisomer thereof. In some embodiments, the disease may be caused by a mutation to a gene or protein sequence related to a member of the eIF2 pathway (e.g., the eIF2α signaling pathway or ISR pathway).

In another aspect, the present invention features a composition for use in treating a leukodystrophy such as vanishing white matter disease (VWMD) or childhood ataxia with central nervous system hypomyelination. In some embodiments, the leukodystrophy is characterized by an amino acid mutation (e.g., an amino acid deletion, amino acid addition, or amino acid substitution) in a tRNA synthetase. In some embodiments, the composition comprising a compound of Formula (I) enhances eIF2B activity in a subject with a leukodystrophy, such as vanishing white matter disease (VWMD) or childhood ataxia with central nervous system hypomyelination.

In another aspect, the present invention features a composition for use in treating a disease or disorder related to an amino acid mutation (e.g., an amino acid deletion, amino acid addition, or amino acid substitution) in a gene or gene product (e.g., RNA or protein) that modulates (e.g., reduces) protein synthesis. In some embodiments, the composition comprising a compound of Formula (I) enhances residual GEF activity of a mutant GEF complex in a subject.

DETAILED DESCRIPTION OF THE INVENTION

The present invention features compounds, compositions, and methods comprising a compound of Formula (I) or a pharmaceutically acceptable salt, solvate, hydrate, tautomer, or stereoisomer thereof for use, e.g., in the modulation (e.g., activation) of eIF2B and the attenuation of the ISR signaling pathway.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley &

Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_1$-$C_{20}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_8$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-6}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. The term "alkenylene," by itself or as part of another substituent, means, unless otherwise stated, a divalent radical derived from an alkene. An alkylene group may be described as, e.g., a $C_1$-$C_6$-membered alkylene, wherein the term "membered" refers to the non-hydrogen atoms within the moiety.

"Alkenyl" refers to a radical of a straight-chain or branched hydrocarbon group having from 2 to 20 carbon atoms, one or more carbon-carbon double bonds, and no triple bonds ("$C_2$-$C_{20}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include, but are not limited to, phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

In certain embodiments, an aryl group is substituted with one or more of groups selected from halo, $C_1$-$C_8$ alkyl, halo-$C_1$-$C_8$ alkyl, haloxy-$C_1$-$C_8$ alkyl, cyano, hydroxy, alkoxy $C_1$-$C_8$ alkyl, and amino.

Examples of representative substituted aryls include the following

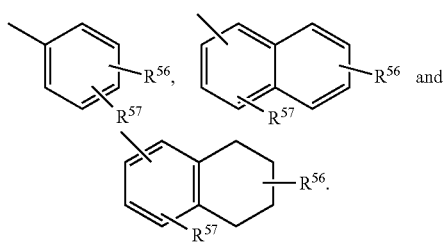

wherein one of $R^{56}$ and $R^{57}$ may be hydrogen and at least one of $R^{56}$ and $R^{57}$ is each independently selected from $C_1$-$C_8$ alkyl, halo-$C_1$-$C_8$ alkyl, 4-10 membered heterocyclyl, alkanoyl, alkoxy-$C_1$-$C_8$ alkyl, heteroaryloxy, alkylamino, arylamino, heteroarylamino, $NR^{58}COR^{59}$, $NR^{58}SOR^{59}$, $NR^{58}SO_2R^{59}$, C(O)Oalkyl, C(O)Oaryl, $CONR^{58}R^{59}$, $CONR^{58}OR^{59}$, $NR^{58}R^{59}$, $SO_2NR^{58}R^{59}$, S-alkyl, S(O)-alkyl, $S(O)_2$-alkyl, S-aryl, S(O)-aryl, $S(O)_2$-aryl; or $R^{56}$ and $R^{57}$ may be joined to form a cyclic ring (saturated or unsaturated) from 5 to 8 atoms, optionally containing one or more heteroatoms selected from the group N, O, or S.

Other representative aryl groups having a fused heterocyclyl group include the following:

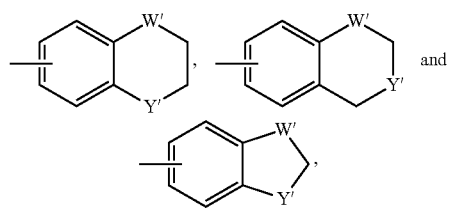

wherein each W' is selected from $C(R^{66})_2$, $NR^{66}$, O, and S; and each Y' is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

Additionally, terms such as "haloalkyl" are meant to include monohaloalkyl and polyhaloalkyl. For example, the term "halo-$C_1$-$C_6$ alkyl" includes, but is not limited to, fluoromethyl, difluoromethyl, trifluoromethyl, 2,2,2-trifluoroethyl, 4-chlorobutyl, 3-bromopropyl, and the like.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)$_2$, —S(O)—$CH_3$, —S(O)$_2$—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—Si($CH_3$)$_3$. Where "heteroalkyl" is recited, followed by recitations of specific heteroalkyl groups, such as —$CH_2$O, —$NR^BR^C$, or the like, it will be understood that the terms heteroalkyl and —$CH_2$O or —$NR^BR^C$ are not redundant or mutually exclusive. Rather, the specific heteroalkyl groups are recited to add clarity. Thus, the term "heteroalkyl" should not be interpreted herein as excluding specific heteroalkyl groups, such as —$CH_2$O, —$NR^BR^C$, or the like.

Similarly, the term "heteroalkylene," by itself or as part of another substituent, means, unless otherwise stated, a divalent radical derived from heteroalkyl, as exemplified, but not limited by, —$CH_2$O— and —$CH_2CH_2$O—. A heteroalkylene group may be described as, e.g., a 2-7-membered heteroalkylene, wherein the term "membered" refers to the non-hydrogen atoms within the moiety. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

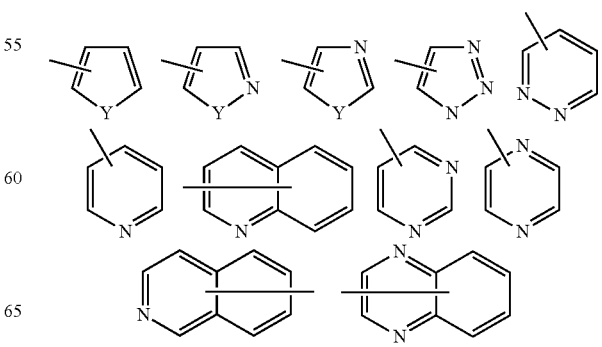

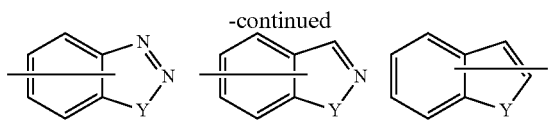

wherein each Y is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

In some embodiments, "cycloalkyl" is a monocyclic, saturated cycloalkyl group having from 3 to 10 ring carbon atoms ("$C_3$-$C_{10}$ cycloalkyl"). In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 5 to 6 ring carbon atoms ("$C_5$-$C_6$ cycloalkyl"). In some embodiments, a cycloalkyl group has 5 to 10 ring carbon atoms ("$C_5$-$C_{10}$ cycloalkyl"). Examples of $C_5$-$C_6$ cycloalkyl groups include cyclopentyl ($C_5$) and cyclohexyl ($C_5$). Examples of $C_3$-$C_6$ cycloalkyl groups include the aforementioned $C_5$-$C_6$ cycloalkyl groups as well as cyclopropyl ($C_3$) and cyclobutyl ($C_4$). Examples of $C_3$-$C_8$ cycloalkyl groups include the aforementioned $C_3$-$C_6$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is substituted $C_3$-$C_{10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

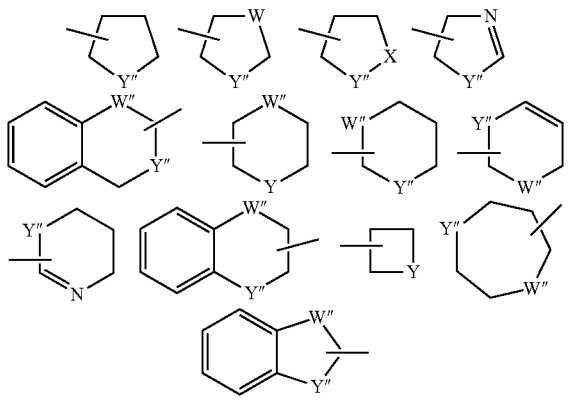

wherein each W″ is selected from $CR^{67}$, $C(R^{67})_2$, $NR^{67}$, O, and S; and each Y″ is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Amino" refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, 4-10 membered heterocyclyl, $C_6$-$C_{10}$ aryl, and 5-10-membered heteroaryl. In some embodiments, amino refers to $NH_2$.

"Cyano" refers to the radical —CN.

"Hydroxy" refers to the radical —OH.

Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2- sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in a first buffer, e.g., in 1 mM-50 mM histidine, 0.1%-2% sucrose, 2%-7% mannitol at a pH range of 4.5 to 5.5, that is combined with a second buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. pancreatic cancer, breast cancer, multiple myeloma, cancers of secretory cells), neurodegenerative diseases (e.g. Alzheimer's disease, Parkinson's disease, frontotemporal dementia), leukodystrophies (e.g., vanishing white matter disease, childhood ataxia with CNS hypo-myelination), postsurgical cognitive dysfunction, traumatic brain injury, intellectual disability syndromes, inflammatory diseases, musculoskeletal diseases, metabolic diseases, or diseases or disorders associated with impaired function of eIF2B or components in a signal transduction or signaling pathway including the ISR and decreased eIF2 pathway activity). For example certain methods herein treat cancer by decreasing or reducing or preventing the occurrence, growth, metastasis, or progression of cancer or decreasing a symptom of cancer; treat neurodegeneration by improving mental wellbeing, increasing mental function, slowing the decrease of mental function, decreasing dementia, delaying the onset of dementia, improving cognitive skills, decreasing the loss of cognitive skills, improving memory, decreasing the degradation of memory, decreasing a symptom of neurodegeneration or extending survival; treat vanishing white matter disease by reducing a symptom of vanishing white matter disease or reducing the loss of white matter or reducing the loss of myelin or increasing the amount of myelin or increasing the amount of white matter; treat childhood ataxia with CNS hypo-myelination by decreasing a symptom of childhood ataxia with CNS hypo-myelination or increasing the level of myelin or decreasing the loss of myelin; treat an intellectual disability syndrome by decreasing a symptom of an intellectual disability syndrome, treat an inflammatory disease by treating a symptom of the inflammatory disease; treat a musculoskeletal disease by treating a symptom of the musculoskeletal disease; or treat a metabolic disease by treating a symptom of the metabolic disease. Symptoms of a disease, disorder, or condition described herein (e.g., cancer, a neurodegenerative disease, a leukodystrophy, an inflammatory disease, a musculoskeletal disease, a metabolic disease, or a condition or disease associated with impaired function of eIF2B or components in a signal transduction pathway including the eIF2 pathway, eIF2α phosphorylation. or ISR pathway) would be known or may be determined by a person of ordinary skill in the art. The term "treating" and conjugations thereof, include prevention of an injury, pathology, condition, or disease (e.g. preventing the development of one or more symptoms of a disease, disorder, or condition described herein).

An "effective amount" is an amount sufficient to accomplish a stated purpose (e.g. achieve the effect for which it is administered, treat a disease, reduce enzyme activity, increase enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

A "reduction" of a symptom or symptoms (and grammatical equivalents of this phrase) means decreasing of the severity or frequency of the symptom(s), or elimination of the symptom(s).

The term "associated" or "associated with" in the context of a substance or substance activity or function associated with a disease (e.g., a disease or disorder described herein, e.g., cancer, a neurodegenerative disease, a leukodystrophy, an inflammatory disease, a musculoskeletal disease, a metabolic disease, or a disease or disorder associated with impaired function of eIF2B or components in a signal transduction pathway including the eIF2 pathway, eIF2α phosphorylation. or ISR pathway) means that the disease is caused by (in whole or in part), or a symptom of the disease is caused by (in whole or in part) the substance or substance activity or function. For example, a symptom of a disease or condition associated with an impaired function of the eIF2B may be a symptom that results (entirely or partially) from a decrease in eIF2B activity (e.g. decrease in eIF2B activity or levels, increase in eIF2α phosphorylation or activity of phosphorylated eIF2α or reduced eIF2 activity or increase in activity of phosphorylated eIF2α signal transduction or the ISR signalling pathway). As used herein, what is described as being associated with a disease, if a causative agent, could be a target for treatment of the disease. For example, a disease associated with decreased eIF2 activity or eIF2 pathway activity, may be treated with an agent (e.g., compound as described herein) effective for increasing the level or activity of eIF2 or eIF2 pathway or a decrease in phosphorylated eIF2α activity or the ISR pathway. For example, a disease associated with phosphorylated eIF2α may be treated with an agent (e.g., compound as described herein) effective for decreasing the level of activity of phosphorylated eIF2α or a downstream component or effector of phosphorylated eIF2α. For example, a disease associated with eIF2α may be treated with an agent (e.g., compound as described herein) effective for increasing the level of activity of eIF2 or a downstream component or effector of eIF2.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. eIF2B, eIF2α, or a component of the eIF2 pathway or ISR pathway). In some embodiments contacting includes allowing a compound described herein to interact with a protein or enzyme that is involved in a signaling pathway (e.g. eIF2B, eIF2α, or a component of the eIF2 pathway or ISR pathway).

As defined herein, the term "inhibition", "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g., eIF2B, eIF2α, or a component of the eIF2 pathway, pathway activated by eIF2α phosphorylation, or ISR pathway). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. eIF2B, eIF2α, or a component of the eIF2 pathway or ISR pathway, wherein each is associated with cancer, a neurodegenerative disease, a leukodystrophy, an inflammatory disease, a musculoskeletal disease, or a metabolic disease). Inhibition may include, at least in part, partially or totally decreasing stimulation, decreasing or reducing activation, or deactivating, desensitizing, or down-regulating signal transduction or enzymatic activity or the amount of a protein (e.g. eIF2B, eIF2α, or component of the eIF2 pathway or ISR pathway) that may modulate the level of another protein or increase cell survival (e.g., decrease in phosphorylated eIF2α pathway activity may increase cell survival in cells that may or may not have an increase in phosphorylated eIF2α pathway activity relative to a non-disease control or decrease in eIF2α pathway activity may increase cell survival in cells that may or may not have an increase in eIF2α pathway activity relative to a non-disease control).

As defined herein, the term "activation", "activate", "activating" and the like in reference to a protein-activator (e.g. agonist) interaction means positively affecting (e.g. increasing) the activity or function of the protein (e.g. eIF2B, eIF2α, or component of the eIF2 pathway or ISR pathway) relative to the activity or function of the protein in the absence of the activator (e.g. compound described herein). In some embodiments, activation refers to an increase in the activity of a signal transduction pathway or signaling pathway (e.g. eIF2B, eIF2α, or component of the eIF2 pathway or ISR pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of eIF2B, eIF2α, or component of the eIF2 pathway or ISR pathway associated with cancer, a neurodegenerative disease, a leukodystrophy, an inflammatory disease, a musculoskeletal disease, or a metabolic disease). Activation may include, at least in part, partially or totally increasing stimulation, increasing or enabling activation, or activating, sensitizing, or up-regulating signal transduction or enzymatic activity or the amount of a protein (e.g., eIF2B, eIF2α, or component of the eIF2 pathway or ISR pathway) that may modulate the level of another protein or increase cell survival (e.g., increase in eIF2α activity may increase cell survival in cells that may or may not have a reduction in eIF2α activity relative to a non-disease control).

The term "modulation" refers to an increase or decrease in the level of a target molecule or the function of a target molecule. In some embodiments, modulation of eIF2B, eIF2α, or a component of the eIF2 pathway or ISR pathway may result in reduction of the severity of one or more symptoms of a disease associated with eIF2B, eIF2α, or a component of the eIF2 pathway or ISR pathway (e.g., cancer, a neurodegenerative disease, a leukodystrophy, an inflammatory disease, a musculoskeletal disease, or a metabolic disease) or a disease that is not caused by eIF2B, eIF2α, or a component of the eIF2 pathway or ISR pathway but may benefit from modulation of eIF2B, eIF2α, or a component of the eIF2 pathway or ISR pathway (e.g., decreasing in level or level of activity of eIF2B, eIF2α or a component of the eIF2 pathway).

The term "modulator" as used herein refers to modulation of (e.g., an increase or decrease in) the level of a target molecule or the function of a target molecule. In embodiments, a modulator of eIF2B, eIF2α, or component of the eIF2 pathway or ISR pathway is an anti-cancer agent. In embodiments, a modulator of eIF2B, eIF2α, or component of the eIF2 pathway or ISR pathway is a neuroprotectant. In embodiments, a modulator of eIF2B, eIF2α, or component of the eIF2 pathway or ISR pathway is a memory enhancing agent. In embodiments, a modulator of eIF2B, eIF2α, or component of the eIF2 pathway or ISR pathway is a memory enhancing agent (e.g., a long term memory enhancing agent). In embodiments, a modulator of eIF2B, eIF2α, or component of the eIF2 pathway or ISR pathway is an anti-inflammatory agent. In some embodiments, a modulator of eIF2B, eIF2α, or component of the eIF2 pathway or ISR pathway is a pain-relieving agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease", "disorder" or "condition" refers to a state of being or health status of a patient or subject capable of being treated with a compound, pharmaceutical composition, or method provided herein. In some embodiments, the compounds and methods described herein comprise reduction or elimination of one or more symptoms of the disease, disorder, or condition, e.g., through administration of a compound of Formula (I) or a pharmaceutically acceptable salt thereof.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

The term "eIF2B" as used herein refers to the heteropentameric eukaryotic translation initiation factor 2B. eIF2B is composed of five subunits: eIF2B1, eIF2B2, eIF2B3, eIF2B4 and eIF2B5. eIF2B1 refers to the protein associated with Entrez gene 1967, OMIM 606686, Uniprot Q14232, and/or RefSeq (protein) NP_001405. eIF2B2 refers to the protein associated with Entrez gene 8892, OMIM 606454, Uniprot P49770, and/or RefSeq (protein) NP_055054. eIF2B3 refers to the protein associated with Entrez gene 8891, OMIM 606273, Uniprot Q9NR50, and/or RefSeq (protein) NP_065098. eIF2B4 refers to the protein associated with Entrez gene 8890, OMIM 606687, Uniprot Q9UI10, and/or RefSeq (protein) NP_751945. eIF2B5 refers to the protein associated with Entrez gene 8893, OMIM 603945, Uniprot Q13144, and/or RefSeq (protein) NP_003898.

The terms "eIF2alpha," "eIF2α," or "eIF2α" are interchangeable and refer to the protein "eukaryotic translation initiation factor 2 alpha subunit eIF2S1". In embodiments, "eIF2alpha", "eIF2α" or "eIF2α" refer to the human protein. Included in the terms "eIF2alpha", "eIF2α" or "eIF2α" are the wildtype and mutant forms of the protein. In embodiments, "eIF2alpha", "eIF2α" or "eIF2α" refer to the protein associated with Entrez Gene 1965, OMIM 603907, UniProt P05198, and/or RefSeq (protein) NP_004085. In embodiments, the reference numbers immediately above refer to the protein and associated nucleic acids known as of the date of filing of this application.

Compounds

In one aspect, the present invention features a compound of Formula (I):

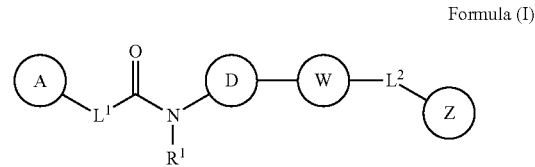

Formula (I)

or a pharmaceutically acceptable salt, solvate, hydrate, tautomer, or stereoisomer thereof, wherein D is a bridged monocyclic cycloalkyl, bridged monocyclic heterocyclyl, or cubanyl, wherein each bridged monocyclic cycloalkyl, bridged monocyclic heterocyclyl, or cubanyl is optionally substituted with 1-4 $R^X$; $L^1$ and $L^2$ are each independently $C_1$-$C_6$ alkylene, 2-7 membered heteroalkylene, or —O—, wherein each $C_1$-$C_6$ alkylene or 2-7 membered heteroalkylene is optionally substituted with 1-5 $R^X$; $R^1$ is hydrogen or $C_1$-$C_6$ alkyl; A and W are each independently phenyl or 5-6-membered heteroaryl, wherein each phenyl or 5-6-membered heteroaryl is optionally substituted with 1-5 $R^Y$; Z is hydrogen, phenyl, or 5-6-membered heteroaryl, wherein each phenyl or 5-6-membered heteroaryl is optionally substituted with 1-5 $R^Y$; each $R^X$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, —$SR^E$, —$S(O)R^D$, and —$S(O)_2R^D$; each $R^Y$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl oxo, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, —$S(R^F)_m$, —$S(O)R^D$, —$S(O)_2R^D$, and $G^1$; or 2 $R^Y$ groups on adjacent atoms, together with the atoms to which they are attached form a 3-7-membered fused cycloalkyl, 3-7-membered fused heterocyclyl, aryl, or 5-6 membered fused heteroaryl optionally substituted with 1-5 $R^X$; each $G^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 $R^Z$; each $R^Z$ is independently selected from the group consisting of $C_1$-$C_6$ alkyl, hydroxy-$C_1$-$C_6$ alkyl, halo-$C_1$-$C_6$ alkyl, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, and —$S(O)_2R^D$; $R^A$ is, at each occurrence, independently hydrogen, $C_1$-$C_6$ alkyl, halo-$C_1$-$C_6$ alkyl, —$C(O)NR^BR^C$, —$C(O)R^D$, —$C(O)OH$, or —$C(O)OR^D$; each of $R^B$ and $R^C$ is independently hydrogen or $C_1$-$C_6$ alkyl; or $R^B$ and $R^C$ together with the atom to which they are attached form a 3-7-membered heterocyclyl ring optionally substituted with 1-3 $R^Z$; each $R^D$ is independently $C_1$-$C_6$ alkyl or halo-$C_1$-$C_6$ alkyl; each $R^E$ is independently hydrogen $C_1$-$C_6$ alkyl, or halo-$C_1$-$C_6$ alkyl; each $R^F$ is independently hydrogen, $C_1$-$C_6$ alkyl, or halo; and m is 1, 3, or 5.

In some embodiments, D is a bridged monocyclic cycloalkyl optionally substituted with 1-4 $R^X$. In some embodiments, D is a bridged 4-6 membered cycloalkyl optionally substituted with 1-4 $R^X$. In some embodiments, D is bicyclo[1.1.1]pentane, bicyclo[2.2.2]heptane, bicyclo[2.1.1]hexane, or bicyclo[2.2.2]octane, each of which is optionally substituted with 1-4 $R^X$ groups. In some embodiments, D is bicyclo[1.1.1]pentane or bicyclo[2.2.2]octane, each of which is optionally substituted with 1-4 $R^X$ groups. In some embodiments, D is

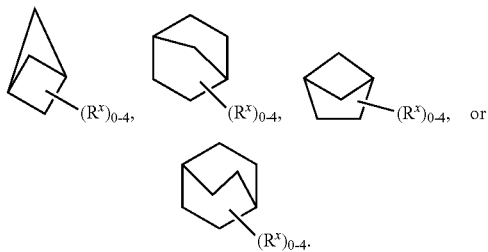

In some embodiments, D is

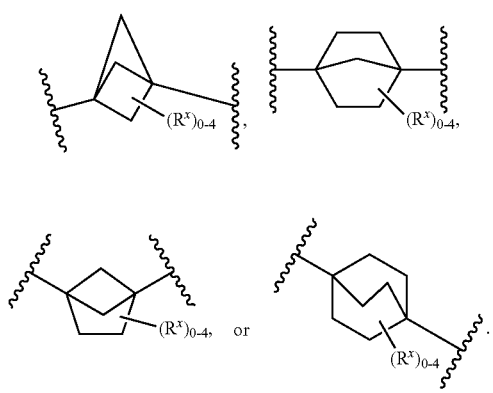

In some embodiments, D is

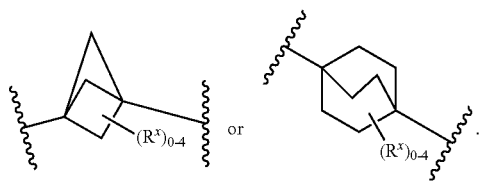

In some embodiments, D is substituted with 0 $R^X$. In some embodiments, D is

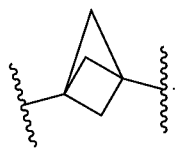 [SMILES: *C12CC(*)(C1)C2]

In some embodiments, D is substituted with 1 $R^X$. In some embodiments, D is

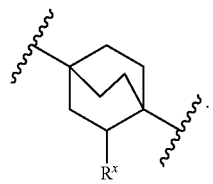

In some embodiments, $R^X$ is oxo or —$OR^A$ (e.g., oxo, or OH). In some embodiments, D is

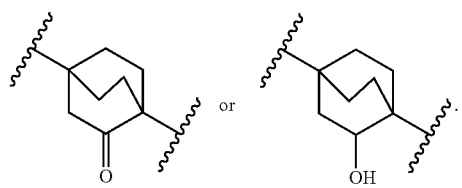 [SMILES: *C12CCC(*)(CC1)C(=O)C2 ; *C12CCC(*)(CC1)C(O)C2]

In some embodiments, both of $L^1$ and $L^2$ are independently 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is substituted by 0 $R^X$. In some embodiments, each $L^1$ and $L^2$ is independently selected from $CH_2O$—*, $CH_2OCH_2$—*, or —O—, and "-*" indicates the attachment point to A or Z, respectively. In some embodiments, $L^1$ is $CH_2O$—* or $CH_2OCH_2$—*, $L^2$ selected from $CH_2O$—*, $CH_2OCH_2$—* or —O—, and "-*" indicates the attachment point to A or Z, respectively. In some embodiments, $L^1$ is $CH_2O$—* or $CH_2OCH_2$—*, $L^2$ is selected from $CH_2O$—* or —O—, and "-*" indicates the attachment point to A or Z, respectively.

In some embodiments, $R^1$ is hydrogen.

In some embodiments, each A and W is independently phenyl or 5-6-membered heteroaryl and Z is hydrogen, phenyl, or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A, W, and Z is independently phenyl, pyridyl, oxadiazolyl, imidazolyl, triazolyl, or isoxazolyl, each of which is optionally substituted with 1-5 $R^Y$ groups. In some embodiments, each of A, W, and Z is independently phenyl, pyridyl, oxadiazolyl, triazolyl, or isoxazolyl, each of which is optionally substituted with 1-5 $R^Y$ groups.

In some embodiments, each of A, W, and Z is selected from:

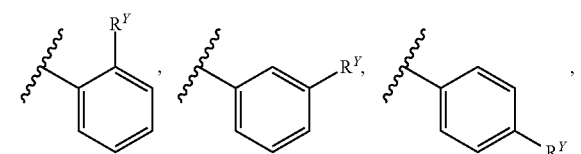
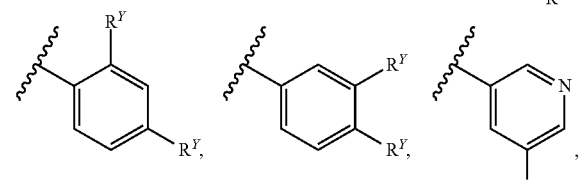
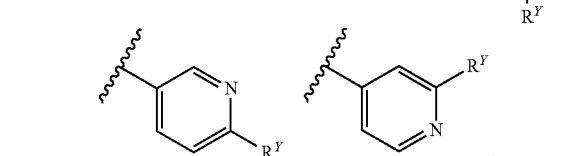
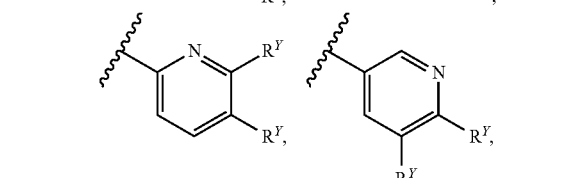
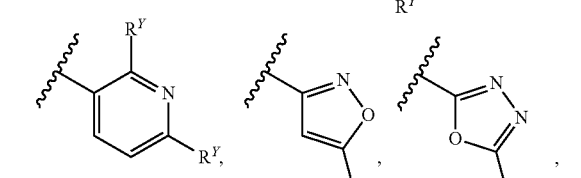
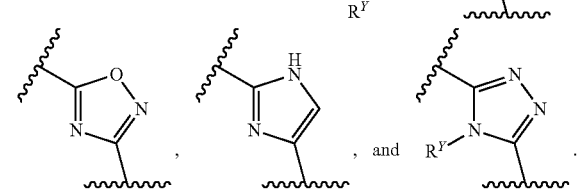

In some embodiments, each of A, W, and Z is selected from:

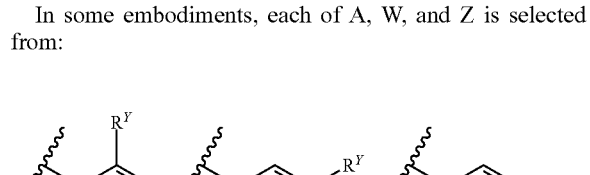

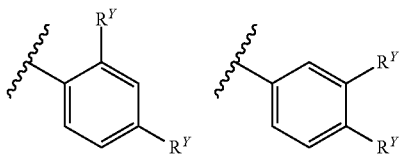
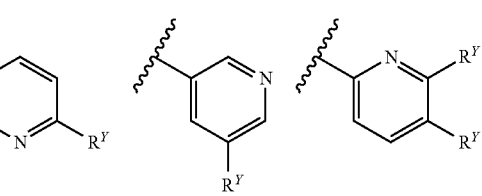
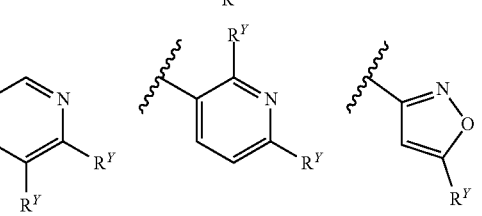
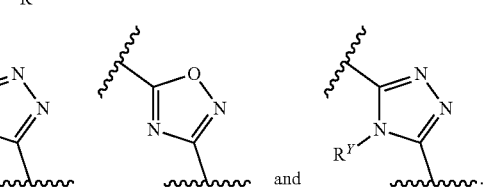

and

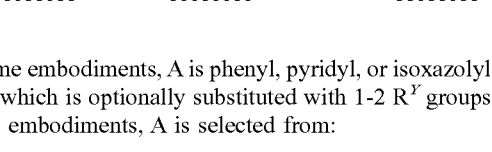

In some embodiments, A is phenyl, pyridyl, or isoxazolyl, each of which is optionally substituted with 1-2 $R^Y$ groups. In some embodiments, A is selected from:

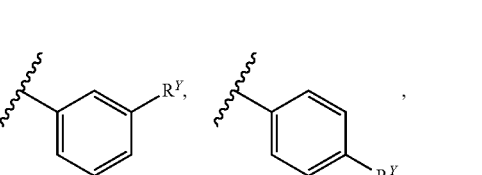
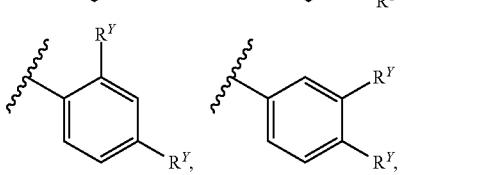
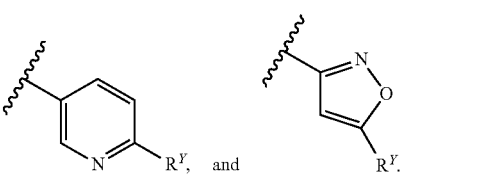

and

In some embodiments, A is phenyl substituted with 1-2 $R^Y$ groups. In some embodiments, A is selected from:

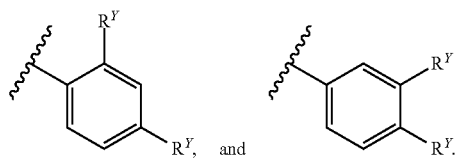

In some embodiments, W is oxadiazolyl, imidazolyl, or triazolyl. In some embodiments, W is selected from:

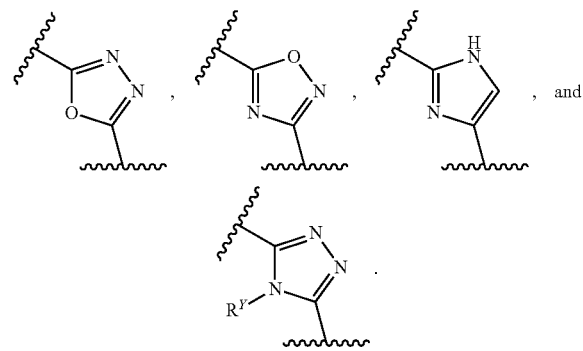

In some embodiments, W is oxadiazolyl or triazolyl. In some embodiments, W is selected from:

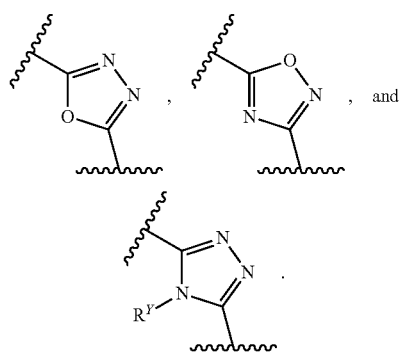

In some embodiments, Z is phenyl or pyridyl, each of which is optionally substituted with 1-2 $R^Y$ groups. In some embodiments, Z is selected from:

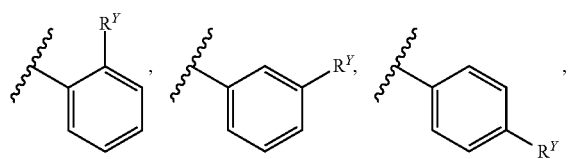

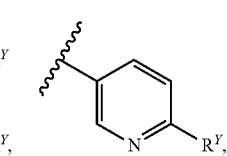

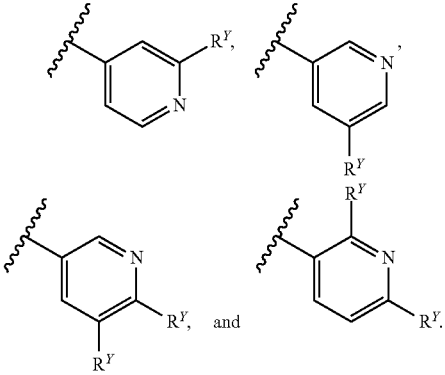

In some embodiments, A is phenyl, pyridyl, or isoxazolyl, W is oxadiazolyl, imidazolyl, or triazolyl, and Z is phenyl or pyridyl, wherein each phenyl, pyridyl, oxadiazolyl, imidazolyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, A is phenyl, pyridyl, or isoxazolyl, W is oxadiazolyl or triazolyl, and Z is phenyl or pyridyl, wherein each phenyl, pyridyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, Z is hydrogen.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, each A and Z is independently substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) is a compound of Formula (I-a):

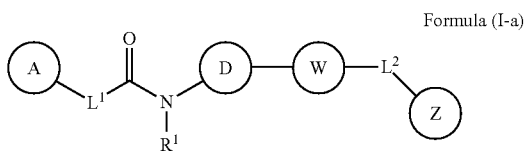

Formula (I-a)

or a pharmaceutically acceptable salt, solvate, hydrate, tautomer, or stereoisomer thereof,
wherein D is bicyclo[1.1.1]pentanyl, each of which is optionally substituted with 1-4 $R^X$ groups; $L^1$ and $L^2$ are each independently $CH_2O$—*, $CH_2OCH_2$—*, or —O—, and "-*" indicates the attachment point to A or Z, respectively; $R^1$ is hydrogen; A and W are each independently phenyl, pyridyl, oxadiazolyl, imidazolyl, triazolyl, or isoxazolyl, each of which is optionally substituted with 1-5 $R^Y$ groups; Z is hydrogen, phenyl, or pyridyl, wherein each phenyl or pyridyl is optionally substituted with 1-5 $R^Y$ groups; each $R^X$ is fluoro, oxo, or OH; each $R^Y$ is independently chloro, fluoro, $CF_3$, $CH_3$, $CH_2CH_3$, $CH(CH_3)_2$, OCH$_3$, OCH(CH$_3$)$_2$, CN, or G$^1$; or 2 R$^Y$ groups on adjacent atoms, together with the atoms to which they are attached form a furanyl, pyrrolyl, or dioxolanyl ring, each of which is optionally substituted with 1-2 R$^X$; and G$^1$ is cyclopropyl.

In some embodiments, the compound of Formula (I) is a compound of Formula (I-b):

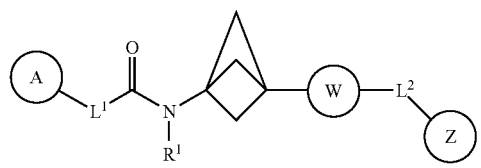

Formula (I-b)

or a pharmaceutically acceptable salt, solvate, hydrate, tautomer, or stereoisomer thereof, wherein each of A, W, Z, L$^1$, and L$^2$ is defined as for Formula (I).

In some embodiments, both of L$^1$ and L$^2$ are independently 2-7 membered heteroalkylene or —O—, and each 2-7 membered heteroalkylene is optionally substituted by 1-5 R$^X$. In some embodiments, L$^1$ is 2-7 membered heteroalkylene, L$^2$ is 2-7 membered heteroalkylene or —O—, and each 2-7 membered heteroalkylene is optionally substituted by 1-5 R$^X$. In some embodiments, L$^1$ is 2-7 membered heteroalkylene, L$^2$ is 2-7 membered heteroalkylene or —O—, and each 2-7 membered heteroalkylene is substituted by 0 R$^X$. In some embodiments, each L$^1$ and L$^2$ is independently selected from CH$_2$O—*, CH$_2$OCH$_2$—*, or —O—, and "-*" indicates the attachment point to A or Z, respectively. In some embodiments, L$^1$ is CH$_2$O—* or CH$_2$OCH$_2$—*, L$^2$ is selected from CH$_2$O—*, CH$_2$OCH$_2$—*, or —O—, and "-*" indicates the attachment point to A or Z, respectively.

In some embodiments, each A and W is independently phenyl or 5-6-membered heteroaryl and Z is hydrogen, phenyl, or 5-6-membered heteroaryl, wherein each phenyl or 5-6-membered heteroaryl is optionally substituted with 1-5 R$^Y$, and each R$^Y$ is independently C$_1$-C$_6$ alkyl, halo-C$_1$-C$_6$ alkyl, halo, cyano, —OR$^A$, or G$^1$. In some embodiments, each of A, W, and Z is independently phenyl, pyridyl, oxadiazolyl, imidazolyl, triazolyl, or isoxazolyl, each of which is optionally substituted with 1-5 R$^Y$ groups. In some embodiments, each of A, W, and Z is selected from:

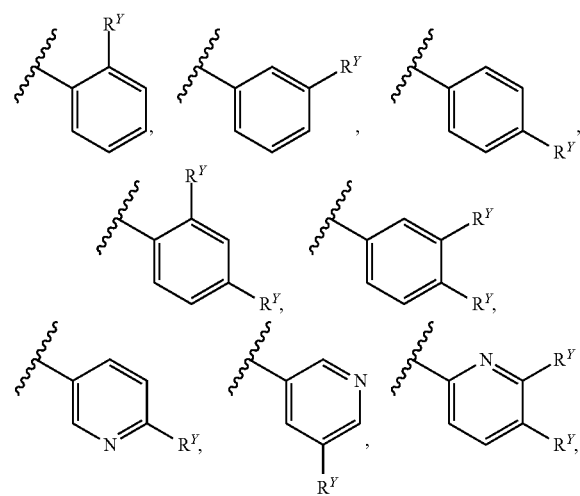

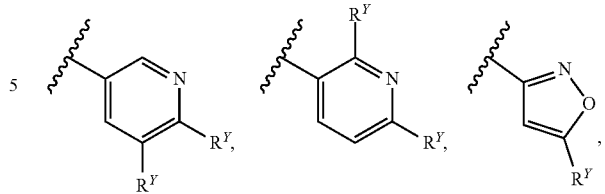

In some embodiments, A is phenyl, pyridyl, or isoxazolyl, each of which is optionally substituted with 1-2 R$^Y$ groups. In some embodiments, A is selected from:

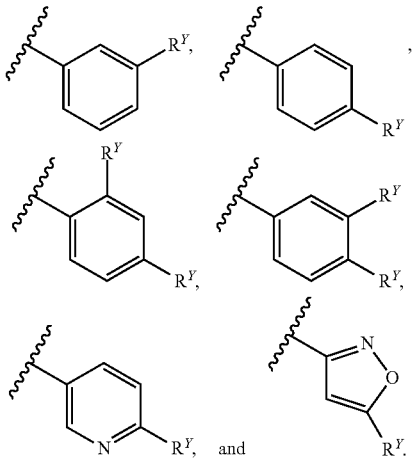

In some embodiments, W is oxadiazolyl, imidazolyl, or triazolyl. In some embodiments, W is selected from:

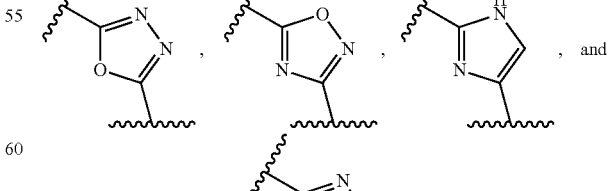

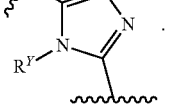

In some embodiments, W is oxadiazolyl or triazolyl. In some embodiments, W is selected from:

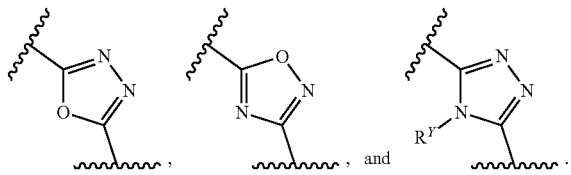

In some embodiments, Z is phenyl or pyridyl, each of which is optionally substituted with 1-2 $R^Y$ groups. In some embodiments, Z is selected from:

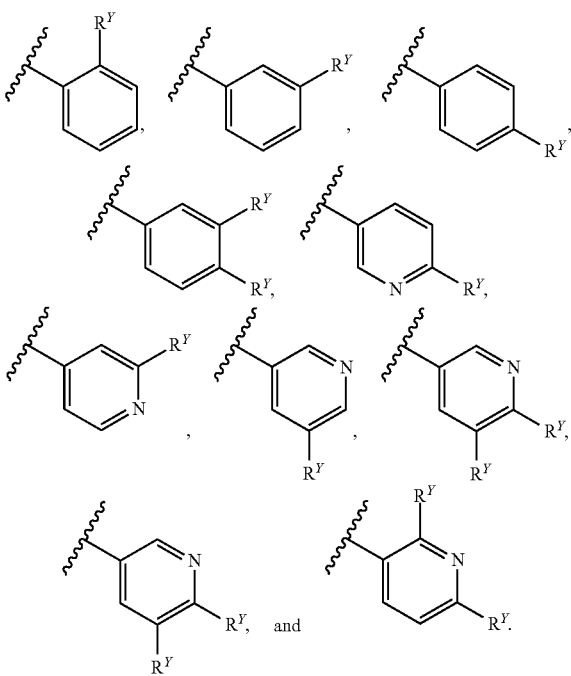

In some embodiments, A is phenyl, pyridyl, or isoxazolyl, W is oxadiazolyl, imidazolyl, or triazolyl, and Z is phenyl or pyridyl, wherein each phenyl, pyridyl, triazolyl, imidazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, Z is hydrogen.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, each A and Z is independently substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) is a compound of Formula (I-c):

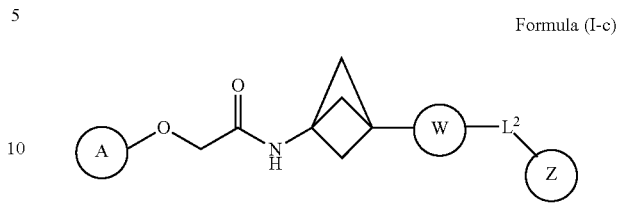

Formula (I-c)

or a pharmaceutically acceptable salt, solvate, hydrate, tautomer, or stereoisomer thereof, wherein each of A, W, Z, and $L^2$ is defined as for Formula (I).

In some embodiments, $L^2$ is 2-7 membered heteroalkylene or —O—, and each 2-7 membered heteroalkylene is optionally substituted by 1-5 $R^X$. In some embodiments, $L^2$ is 2-7 membered heteroalkylene or —O—, and each 2-7 membered heteroalkylene is substituted by 0 $R^X$. In some embodiments, $L^2$ is selected from $CH_2O$—*, $CH_2OCH_2$—*, or —O—, and "-*" indicates the attachment point to Z. In some embodiments, $L^2$ is selected from $CH_2O$—*, $CH_2OCH_2$—*, or —O—, and "-*" indicates the attachment point to Z.

In some embodiments, each A and W is independently phenyl or 5-6-membered heteroaryl and Z is hydrogen, phenyl, or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A, W, and Z is independently phenyl, pyridyl, oxadiazolyl, imidazolyl, triazolyl, or isoxazolyl, each of which is optionally substituted with 1-5 $R^Y$ groups. In some embodiments, each of A, W, and Z is selected from:

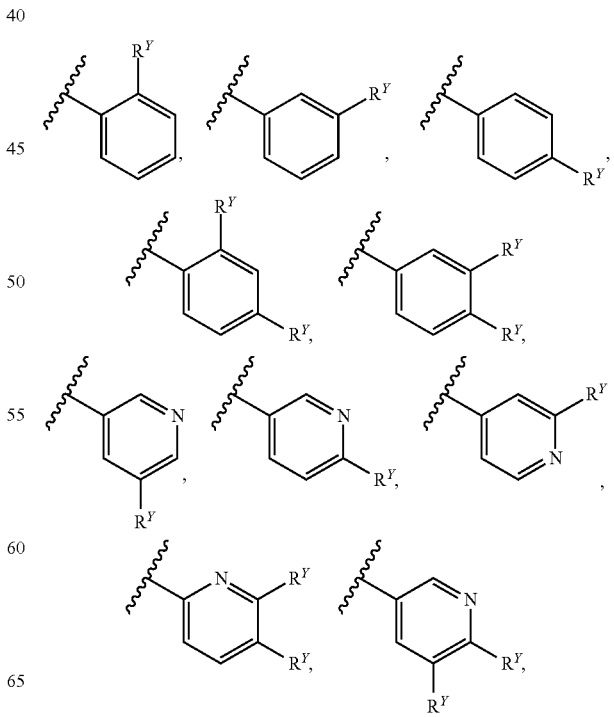

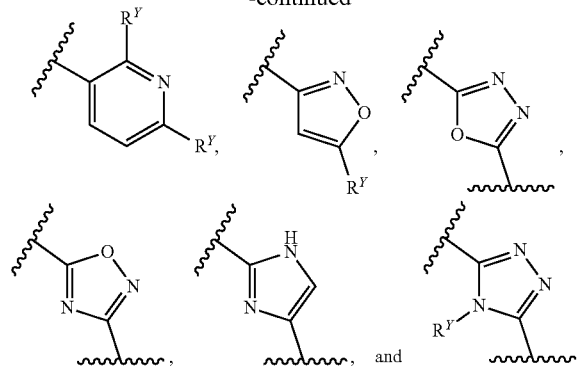

In some embodiments, A is phenyl, pyridyl, or isoxazolyl, each of which is optionally substituted with 1-2 $R^Y$ groups. In some embodiments, A is selected from:

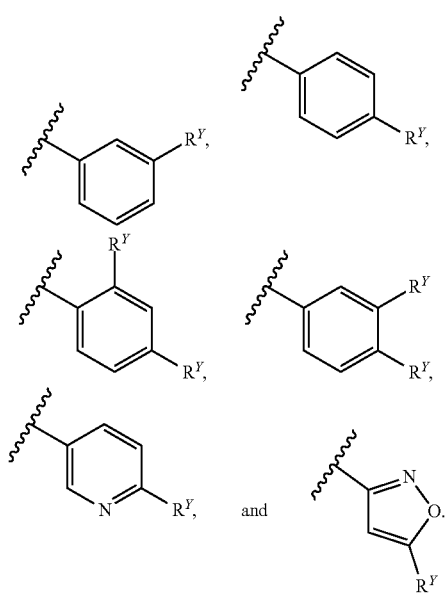

In some embodiments, W is oxadiazolyl, imidazolyl, or triazolyl. In some embodiments, W is selected from:

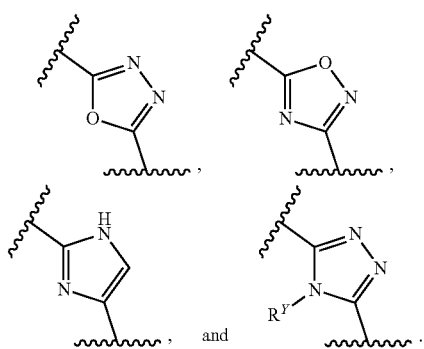

In some embodiments, Z is phenyl or pyridyl, each of which is optionally substituted with 1-2 $R^Y$ groups. In some embodiments, Z is selected from:

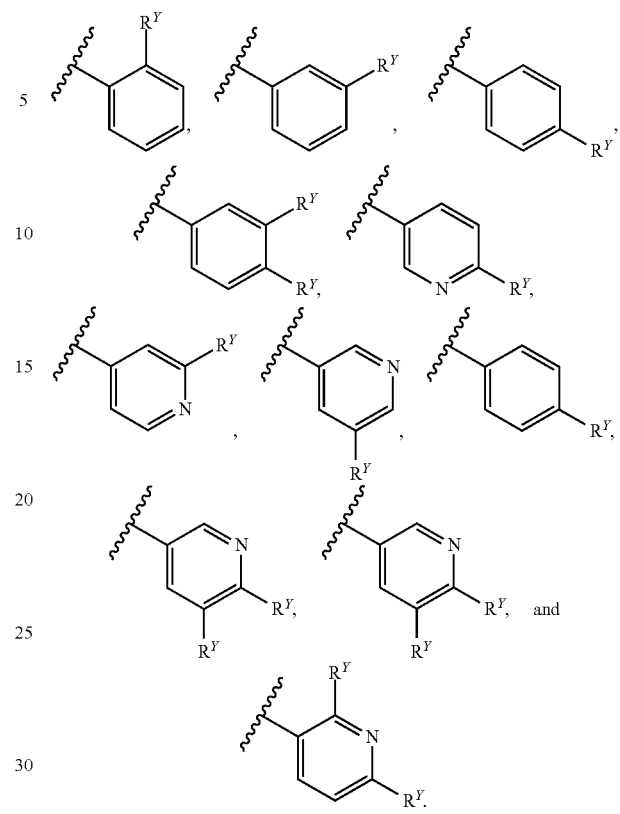

In some embodiments, A is phenyl, pyridyl, or isoxazolyl, W is oxadiazolyl, imidazolyl, or triazolyl, and Z is phenyl or pyridyl, wherein each phenyl, pyridyl, triazolyl, imidazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, Z is hydrogen.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, each A and Z is independently substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$ In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) is a compound of Formula (I-d):

Formula (I-d)

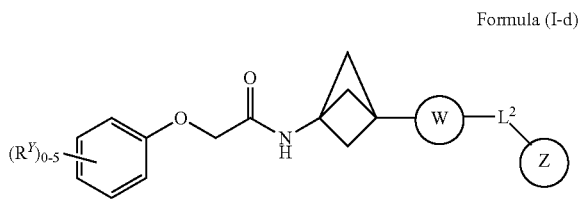

or a pharmaceutically acceptable salt, solvate, hydrate, tautomer, or stereoisomer thereof, wherein each of W, Z, $L^2$, and $R^Y$ is defined as for Formula (I).

In some embodiments, $L^2$ is 2-7 membered heteroalkylene or —O—, and each 2-7 membered heteroalkylene is optionally substituted by 1-5 $R^X$. In some embodiments, $L^2$ is 2-7 membered heteroalkylene or —O—, and each 2-7 membered heteroalkylene is substituted by 0 $R^X$. In some embodiments, $L^2$ is selected from $CH_2O$—*, $CH_2OCH_2$—*, or —O—, and "-*" indicates the attachment point to Z. In some embodiments, $L^2$ is selected from $CH_2O$—*, $CH_2OCH_2$—*, or —O—, and "-*" indicates the attachment point to Z.

In some embodiments, W is phenyl or 5-6-membered heteroaryl and Z is hydrogen, phenyl, or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of W and Z is independently phenyl, pyridyl, oxadiazolyl, imidazolyl, triazolyl, or isoxazolyl, each of which is optionally substituted with 1-5 $R^Y$ groups. In some embodiments, each of W and Z is selected from:

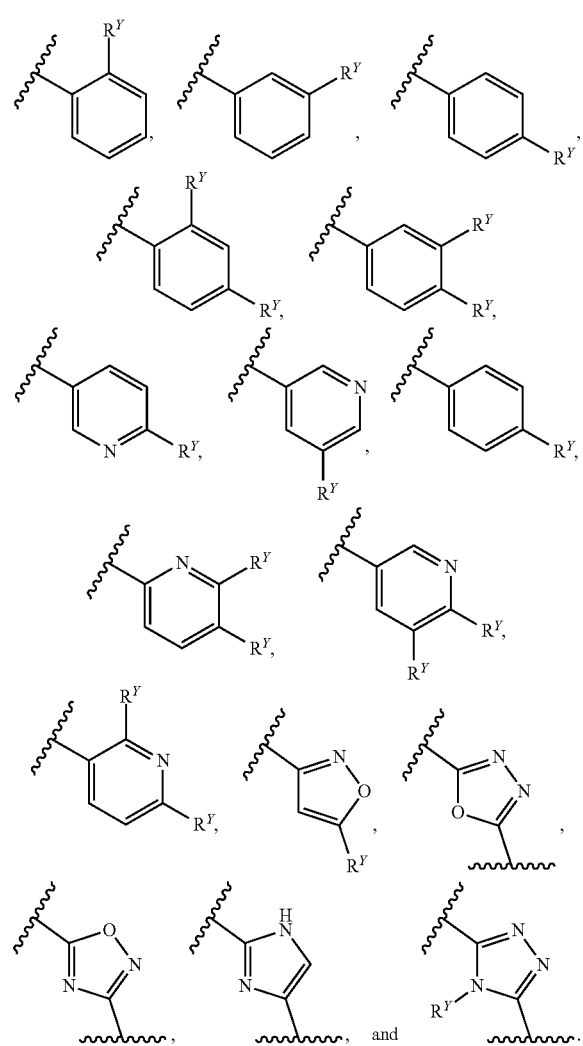

In some embodiments, W is oxadiazolyl, imidazolyl, or triazolyl. In some embodiments, W is selected from:

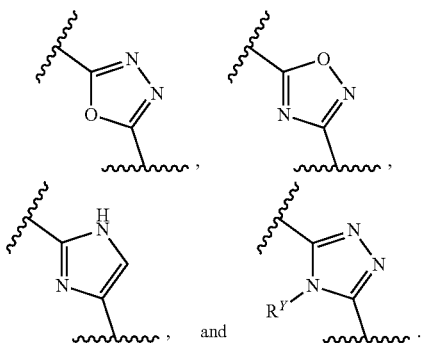

In some embodiments, Z is phenyl or pyridyl, each of which is optionally substituted with 1-2 $R^Y$ groups. In some embodiments, Z is selected from:

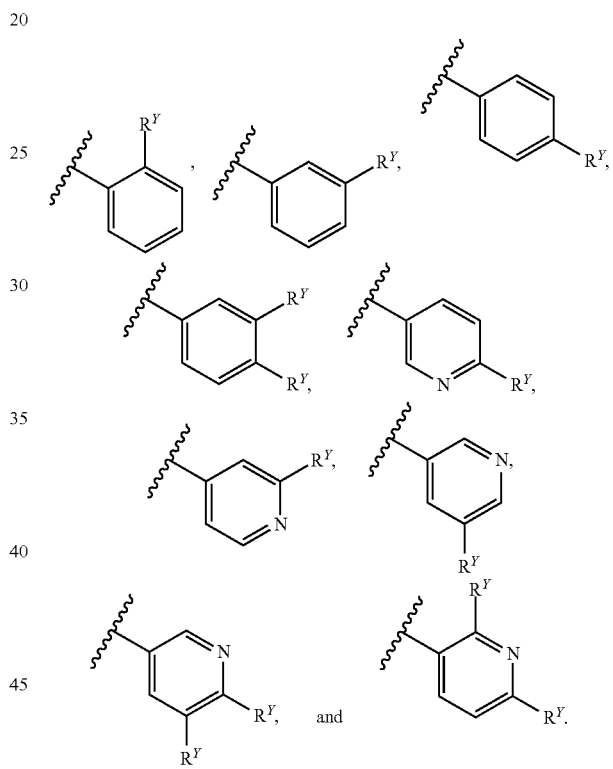

In some embodiments, W is oxadiazolyl, imidazolyl, or triazolyl, and Z is phenyl or pyridyl, wherein each phenyl, pyridyl, triazolyl, imidazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, Z is hydrogen.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, Z is substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, G¹ is cyclopropyl optionally substituted with 1-5 $R^Z$.

In some embodiments, the compound of Formula (I) is a compound of Formula (I-e-1), Formula (I-e-2), Formula (I-e-3), Formula (I-e-4), or Formula (I-e-5):

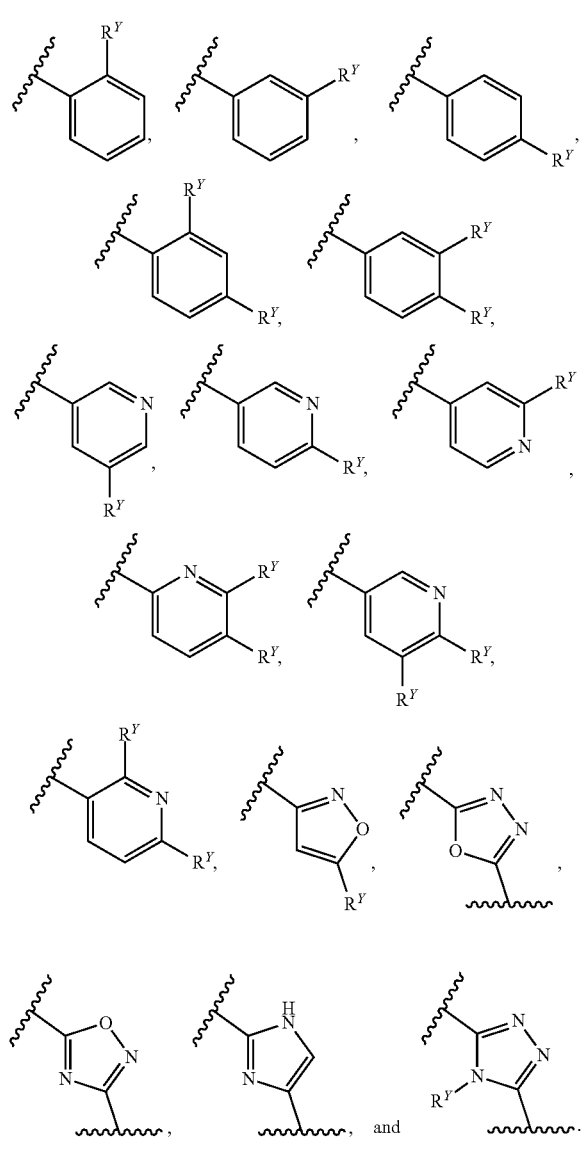

or a pharmaceutically acceptable salt, solvate, hydrate, tautomer, or stereoisomer thereof, wherein each of A, Z, L¹, and L² is defined as for Formula (I).

In some embodiments, both of L¹ and L² are independently 2-7 membered heteroalkylene or —O—, and each 2-7 membered heteroalkylene is optionally substituted by 1-5 $R^X$. In some embodiments, L¹ is 2-7 membered heteroalkylene, L² is 2-7 membered heteroalkylene or —O—, and each 2-7 membered heteroalkylene is optionally substituted by 1-5 $R^X$. In some embodiments, L¹ is 2-7 membered heteroalkylene, L² is 2-7 membered heteroalkylene or —O—, and each 2-7 membered heteroalkylene is substituted by 0 $R^X$. In some embodiments, each L¹ and L² is independently selected from CH₂O—*, CH₂OCH₂—*, or —O—, and "-*" indicates the attachment point to A or Z, respectively. In some embodiments, L¹ is CH₂O—* or CH₂OCH₂—*, L² is selected from CH₂O—*, CH₂OCH₂—*, or —O—, and "-*" indicates the attachment point to A or Z, respectively.

In some embodiments, A is phenyl or 5-6-membered heteroaryl and Z is hydrogen, phenyl, or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or G¹. In some embodiments, each of A and Z is independently phenyl, pyridyl, oxadiazolyl, triazolyl, or isoxazolyl, each of which is optionally substituted with 1-5 $R^Y$ groups. In some embodiments, each of A and Z is selected from:

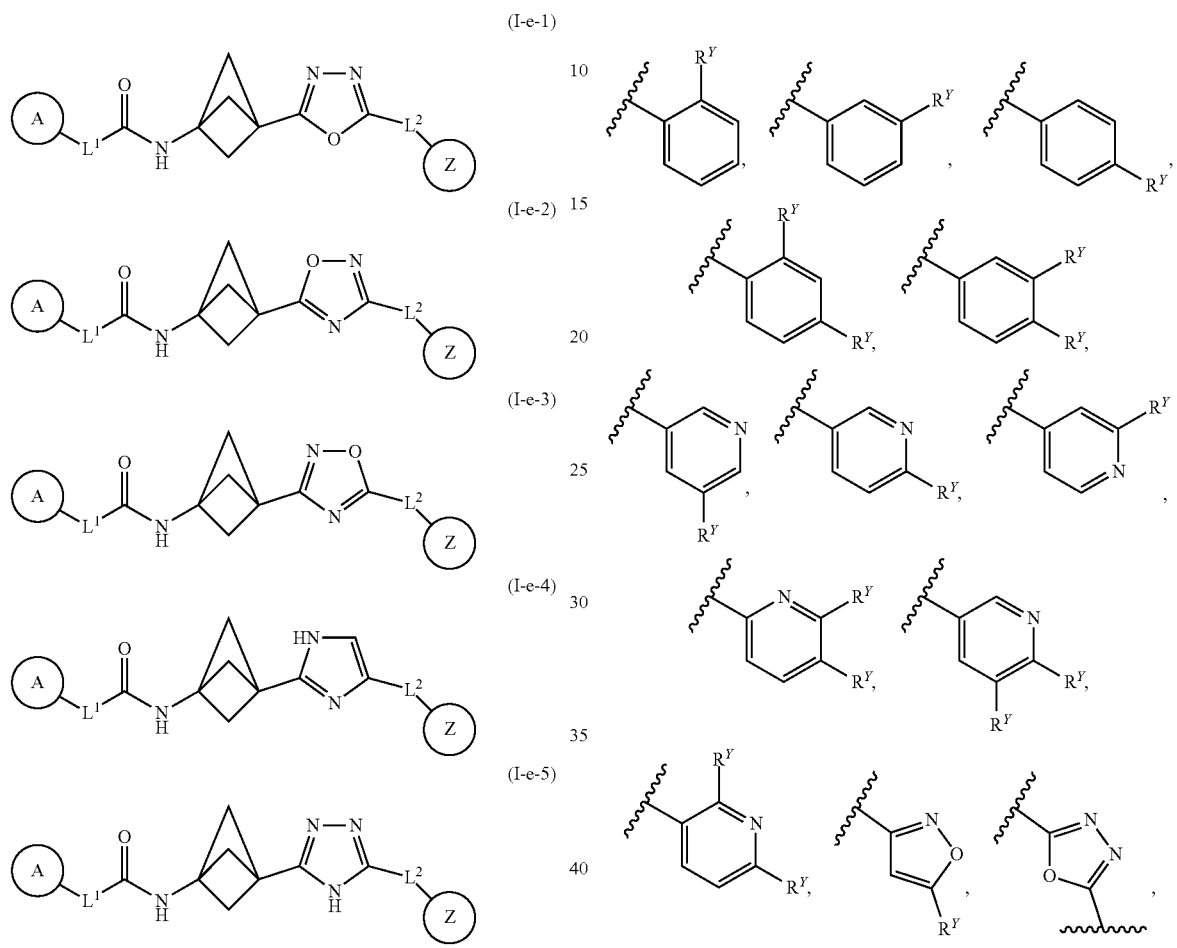

In some embodiments, A is phenyl, pyridyl, or isoxazolyl, each of which is optionally substituted with 1-2 $R^Y$ groups. In some embodiments, A is selected from:

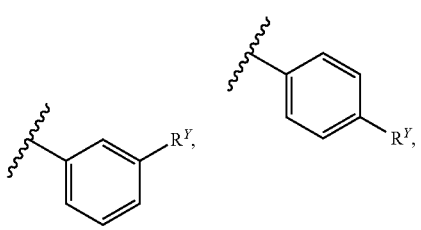

-continued

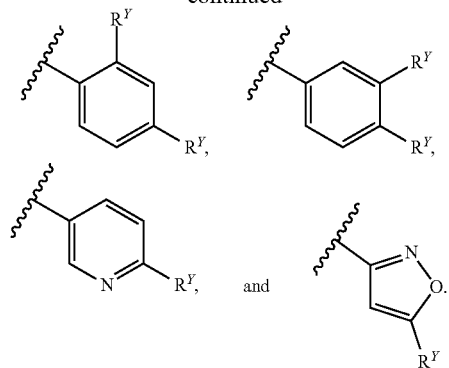

In some embodiments, Z is phenyl or pyridyl, each of which is optionally substituted with 1-2 $R^Y$ groups. In some embodiments, Z is selected from:

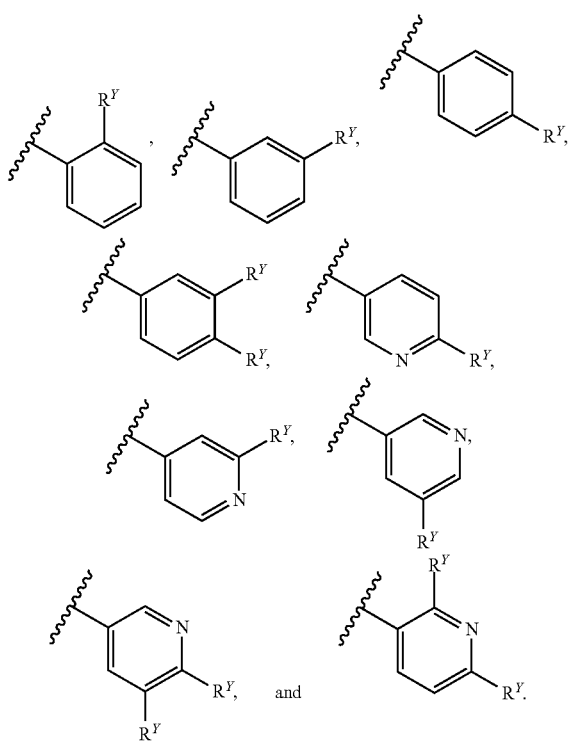

In some embodiments, A is phenyl, pyridyl, or isoxazolyl, and Z is phenyl or pyridyl, wherein each phenyl, pyridyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, Z is hydrogen.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, each A and Z is independently substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) is a compound of Formula (I-f):

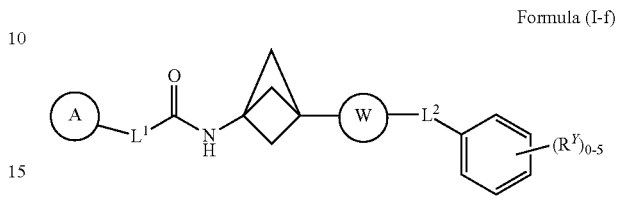

Formula (I-f)

or a pharmaceutically acceptable salt, solvate, hydrate, tautomer, or stereoisomer thereof, wherein each of A, W, $L^1$, $L^2$, and $R^Y$ is defined as for Formula (I).

In some embodiments, both of $L^1$ and $L^2$ are independently 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is substituted by 0 $R^X$. In some embodiments, each $L^1$ and $L^2$ is independently selected from $CH_2O$—*, $CH_2OCH_2$—*, or —O—, and "-*" indicates the attachment point to A or Z, respectively. In some embodiments, $L^1$ is $CH_2O$—* or $CH_2OCH_2$—*, $L^2$ is selected from $CH_2O$—*, $CH_2OCH_2$—*, or —O—, and "-*" indicates the attachment point to A or Z, respectively.

In some embodiments, each A and W is independently phenyl or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A and W is independently phenyl, pyridyl, oxadiazolyl, imidazolyl, triazolyl, or isoxazolyl, each of which is optionally substituted with 1-5 $R^Y$ groups. In some embodiments, each of A and W is selected from:

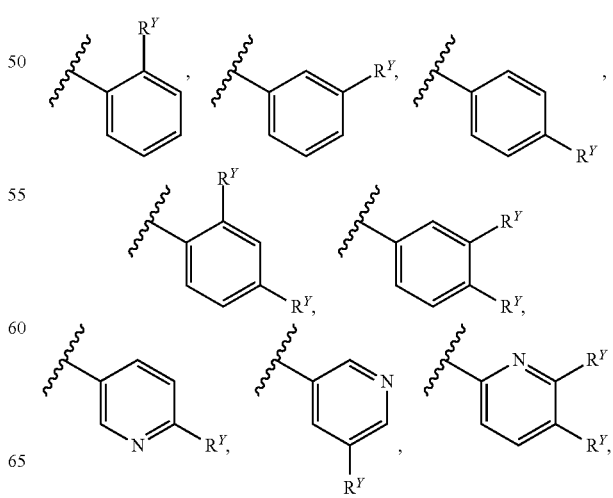

-continued

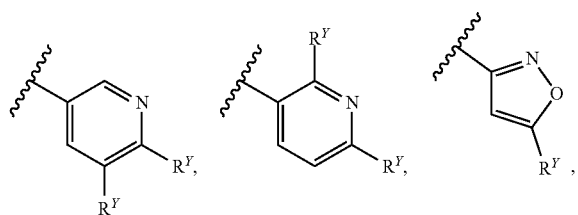

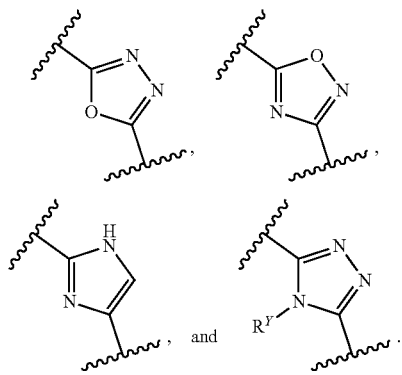

In some embodiments, A is phenyl, pyridyl, or isoxazolyl, each of which is optionally substituted with 1-2 $R^Y$ groups. In some embodiments, A is selected from:

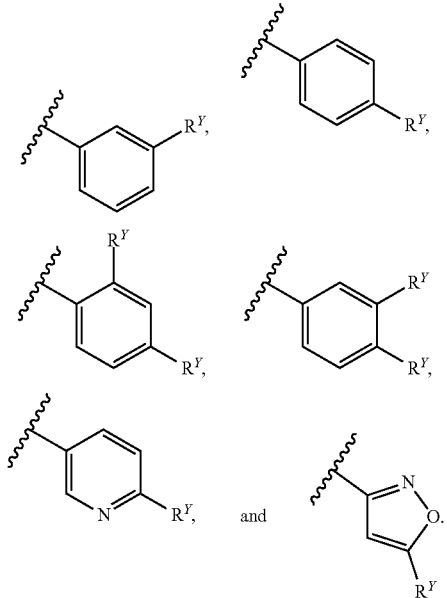

In some embodiments, W is oxadiazolyl, imidazolyl, or triazolyl. In some embodiments, W is selected from:

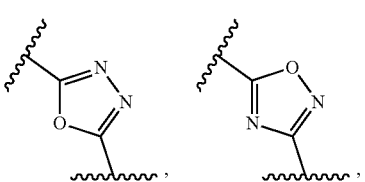

-continued

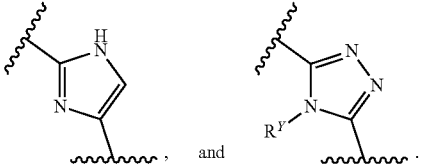

In some embodiments, W is oxadiazolyl or triazolyl. In some embodiments, W is selected from:

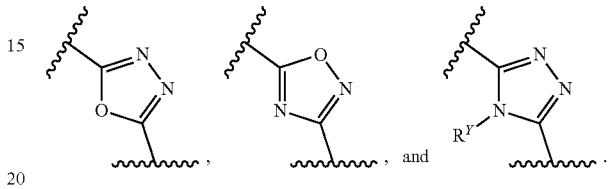

In some embodiments, A is phenyl, pyridyl, or isoxazolyl, and W is oxadiazolyl or triazolyl, wherein each phenyl, pyridyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, A is substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) is a compound of Formula (I-g):

Formula (I-g)

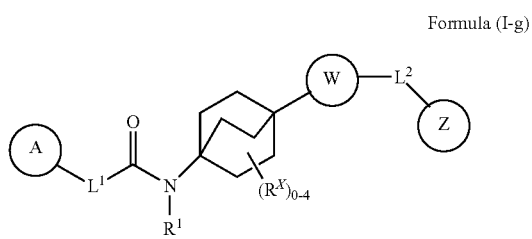

or a pharmaceutically acceptable salt, solvate, hydrate, tautomer, or stereoisomer thereof, wherein each of A, W, Z, $L^1$, $L^2$, and $R^X$ is defined as for Formula (I).

In some embodiments, $R^X$ is oxo or —$OR^A$ (e.g., oxo, or OH).

In some embodiments, both of $L^1$ and $L^2$ are independently 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is optionally substituted by 1-5 $R^X$. In some embodiments, $L^1$ is 2-7 membered heteroalkylene, $L^2$ is 2-7 membered heteroalkylene or —O—, and each 2-7 membered heteroalkylene is substituted by 0 $R^X$. In some embodiments, each $L^1$ and $L^2$ is independently selected from $CH_2O$—*, $CH_2OCH_2$—*, or —O—, and "-*" indicates the attachment point to A or Z, respectively. In some embodiments, $L^1$ is $CH_2O$—* or $CH_2OCH_2$—*, $L^2$ is selected from $CH_2O$—*, $CH_2OCH_2$—*, or —O—, and "-*" indicates the attachment point to A or Z, respectively.

In some embodiments, $R^1$ is hydrogen.

In some embodiments, each A and W is independently phenyl or 5-6-membered heteroaryl and Z is hydrogen, phenyl, or 5-6-membered heteroaryl, wherein each phenyl or 5-6-membered heteroaryl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$. In some embodiments, each of A, W, and Z is independently phenyl, pyridyl, oxadiazolyl, triazolyl, or isoxazolyl, each of which is optionally substituted with 1-5 $R^Y$ groups. In some embodiments, each of A, W, and Z is selected from:

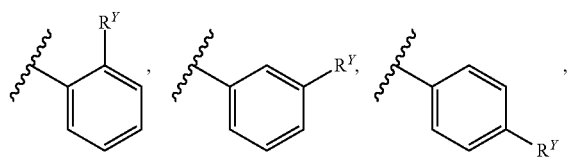

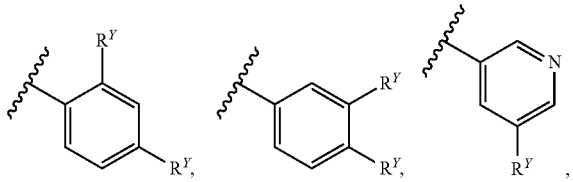

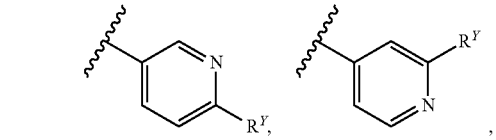

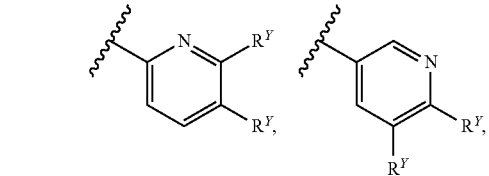

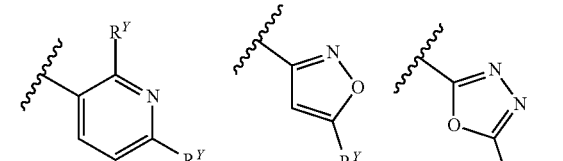

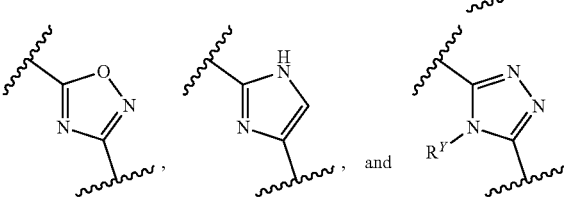

In some embodiments, A is phenyl, pyridyl, or isoxazolyl, each of which is optionally substituted with 1-2 $R^Y$ groups. In some embodiments, A is selected from:

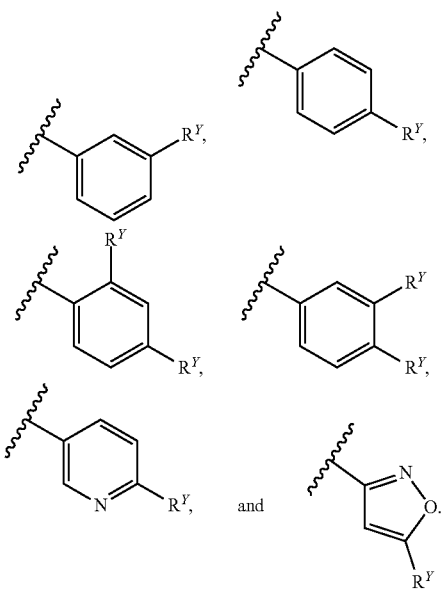

In some embodiments, W is oxadiazolyl, imidazolyl, or triazolyl. In some embodiments, W is selected from:

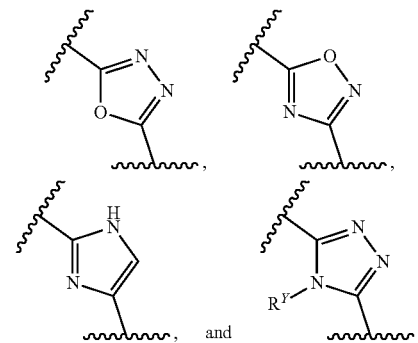

In some embodiments, Z is phenyl or pyridyl, each of which is optionally substituted with 1-2 $R^Y$ groups. In some embodiments, Z is selected from:

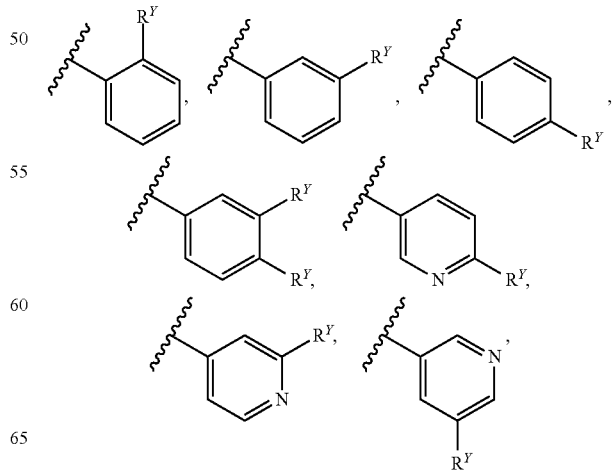

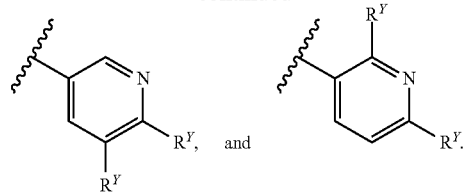

In some embodiments, A is phenyl, pyridyl, or isoxazolyl, W is oxadiazolyl or triazolyl, and Z is phenyl or pyridyl, wherein each phenyl, pyridyl, triazolyl, and isoxazolyl is optionally substituted with 1-5 $R^Y$, and each $R^Y$ is independently $C_1$-$C_6$ alkyl, halo-$C_1$-$C_6$ alkyl, halo, cyano, —$OR^A$, or $G^1$.

In some embodiments, Z is hydrogen.

In some embodiments, each $R^Y$ is independently chloro, fluoro, $CF_3$, $CH_3$, $CH_2CH_3$, $CH(CH_3)_2$, $OCH_3$, $OCH(CH_3)_2$, CN, or $G^1$.

In some embodiments, each A and Z is independently substituted with 2 $R^Y$ on adjacent atoms, and the 2 $R^Y$, together with the atoms to which they are attached, form a 3-7 membered fused heterocyclyl or 5-6 membered fused heteroaryl ring optionally substituted with 1-5 $R^X$. In some embodiments, 2 $R^Y$ together with the atoms to which they are attached form a furanyl, pyrrolyl, or dioxolanyl ring, each of which is optionally substituted with 1-5 $R^X$. In some embodiments, each $R^X$ is independently fluoro.

In some embodiments, $G^1$ is cyclopropyl optionally substituted with 1-5 $R^Z$.

In some embodiments, the compound of Formula (I) (e.g., a compound of Formula (I-a), (I-b), (I-c), (I-d), (I-e-1), (I-e-2). (I-e-3), (I-e-4), (I-e-5), (I-f), or (I-g)) or a pharmaceutically acceptable salt thereof is formulated as a pharmaceutically acceptable composition comprising a compound of any one of the preceding claims and a pharmaceutically acceptable carrier In some embodiments, the compound is selected from any compound set forth in Table 1 or a pharmaceutically acceptable salt, solvate, hydrate, tautomer, or stereoisomer thereof.

TABLE 1

Exemplary compounds of the invention

| Compound No. | Structure |
|---|---|
| 100 | 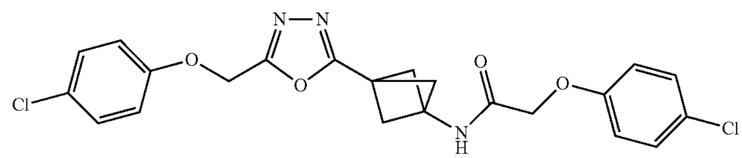 [SMILES: O=C(COc1ccc(Cl)cc1)NC12CC(c3nnc(COc4ccc(Cl)cc4)o3)(C1)C2] |
| 101 | 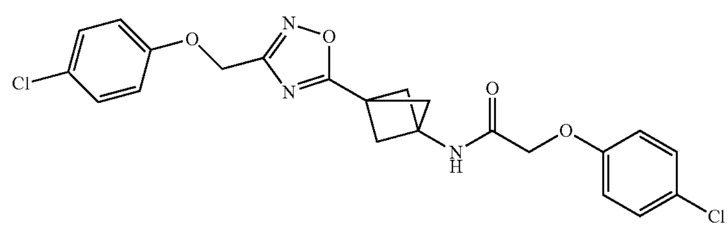 [SMILES: O=C(COc1ccc(Cl)cc1)NC12CC(c3nc(COc4ccc(Cl)cc4)no3)(C1)C2] |
| 102 | 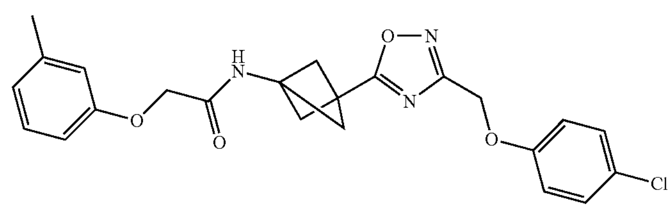 [SMILES: Cc1cccc(OCC(=O)NC23CC(c4nc(COc5ccc(Cl)cc5)no4)(C2)C3)c1] |
| 103 | 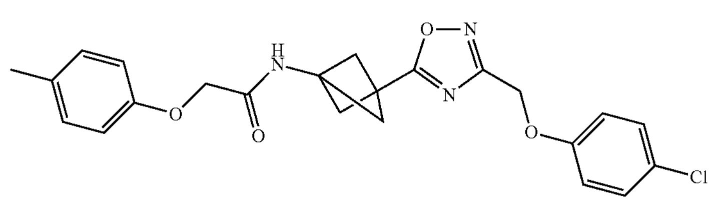 [SMILES: Cc1ccc(OCC(=O)NC23CC(c4nc(COc5ccc(Cl)cc5)no4)(C2)C3)cc1] |
| 104 | 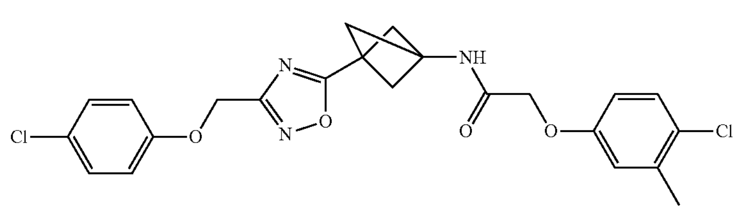 [SMILES: Cc1cc(OCC(=O)NC23CC(c4nc(COc5ccc(Cl)cc5)no4)(C2)C3)ccc1Cl] |

TABLE 1-continued

Exemplary compounds of the invention

| Compound No. | Structure |
| --- | --- |
| 105 | 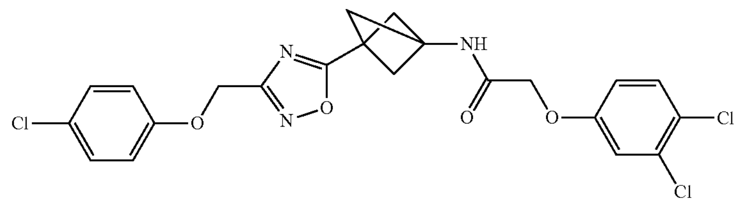 [SMILES: O=C(COc1ccc(Cl)c(Cl)c1)NC12CC(c3nc(COc4ccc(Cl)cc4)no3)(C1)C2] |
| 106 | 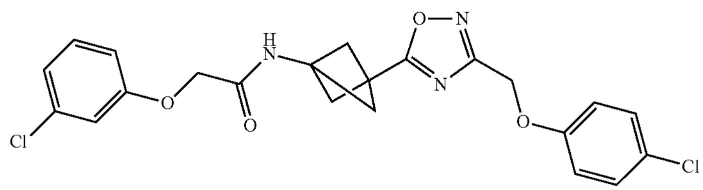 [SMILES: O=C(COc1cccc(Cl)c1)NC12CC(c3nc(COc4ccc(Cl)cc4)no3)(C1)C2] |
| 107 | 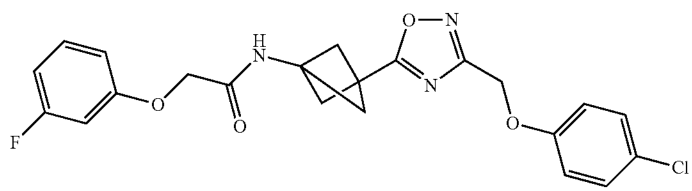 [SMILES: O=C(COc1cccc(F)c1)NC12CC(c3nc(COc4ccc(Cl)cc4)no3)(C1)C2] |
| 108 | 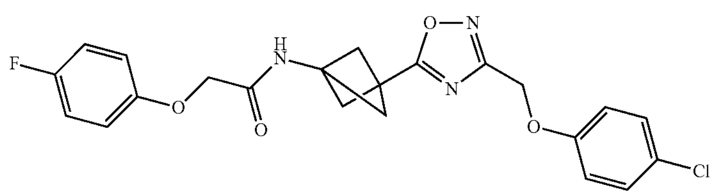 [SMILES: O=C(COc1ccc(F)cc1)NC12CC(c3nc(COc4ccc(Cl)cc4)no3)(C1)C2] |
| 109 | 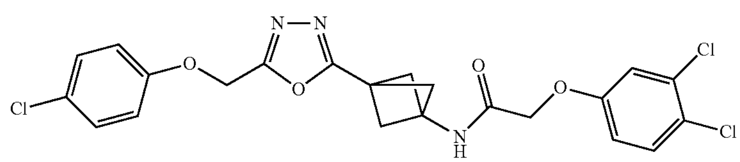 [SMILES: O=C(COc1ccc(Cl)c(Cl)c1)NC12CC(c3nnc(COc4ccc(Cl)cc4)o3)(C1)C2] |
| 110 | 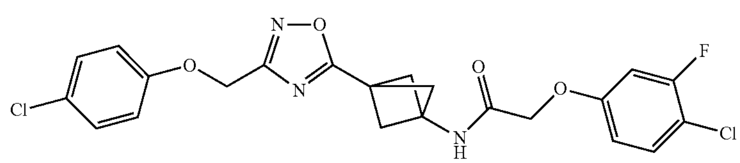 [SMILES: O=C(COc1ccc(Cl)c(F)c1)NC12CC(c3nc(COc4ccc(Cl)cc4)no3)(C1)C2] |
| 111 | 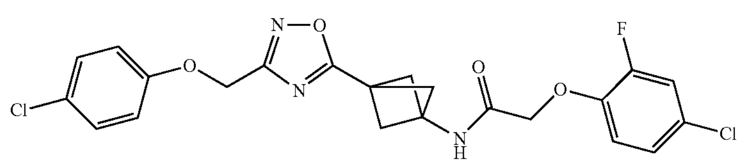 [SMILES: O=C(COc1ccc(Cl)cc1F)NC12CC(c3nc(COc4ccc(Cl)cc4)no3)(C1)C2] |
| 112 | 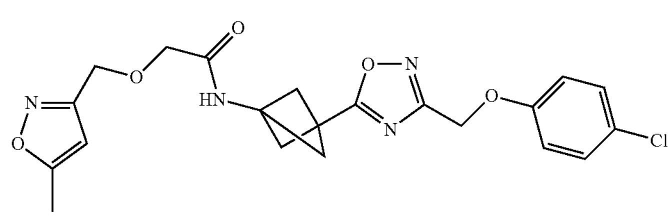 [SMILES: Cc1cc(COCC(=O)NC23CC(c4nc(COc5ccc(Cl)cc5)no4)(C2)C3)no1] |

TABLE 1-continued

Exemplary compounds of the invention

| Compound No. | Structure |
|---|---|
| 113 | 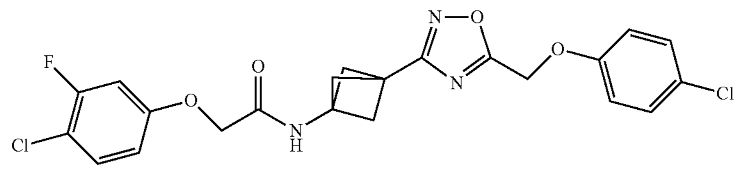 [SMILES: O=C(COc1ccc(Cl)c(F)c1)NC12CC(c3noc(COc4ccc(Cl)cc4)n3)(C1)C2] |
| 114 | 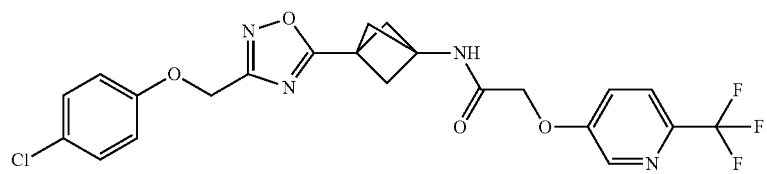 [SMILES: O=C(COc1ccc(C(F)(F)F)nc1)NC12CC(c3nc(COc4ccc(Cl)cc4)no3)(C1)C2] |
| 115 | 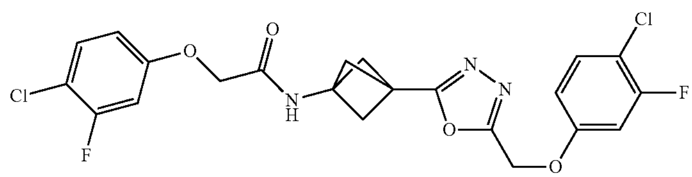 [SMILES: O=C(COc1ccc(Cl)c(F)c1)NC12CC(c3nnc(COc4ccc(Cl)c(F)c4)o3)(C1)C2] |
| 116 | 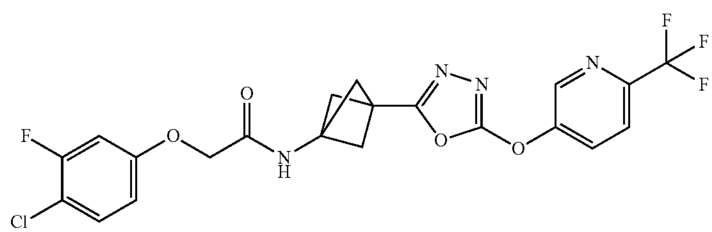 [SMILES: O=C(COc1ccc(Cl)c(F)c1)NC12CC(c3nnc(Oc4ccc(C(F)(F)F)nc4)o3)(C1)C2] |
| 117 | 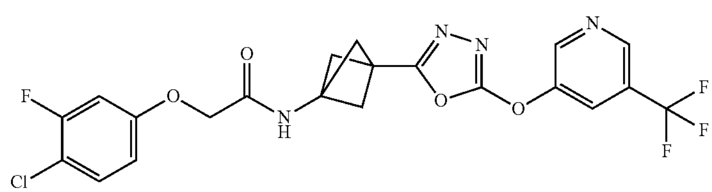 [SMILES: O=C(COc1ccc(Cl)c(F)c1)NC12CC(c3nnc(Oc4cncc(C(F)(F)F)c4)o3)(C1)C2] |
| 118 | 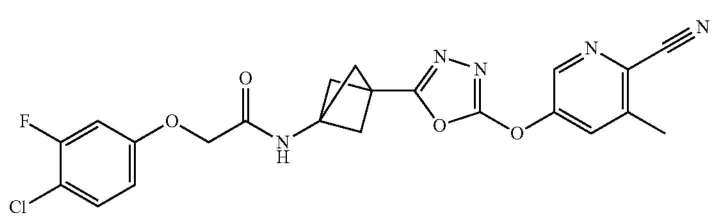 [SMILES: Cc1cc(Oc2nnc(C34CC(NC(=O)COc5ccc(Cl)c(F)c5)(C3)C4)o2)cnc1C#N] |
| 119 | 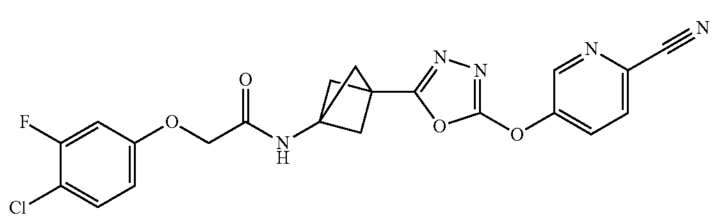 [SMILES: N#Cc1ccc(Oc2nnc(C34CC(NC(=O)COc5ccc(Cl)c(F)c5)(C3)C4)o2)cn1] |

TABLE 1-continued

Exemplary compounds of the invention

| Compound No. | Structure |
|---|---|
| 120 | 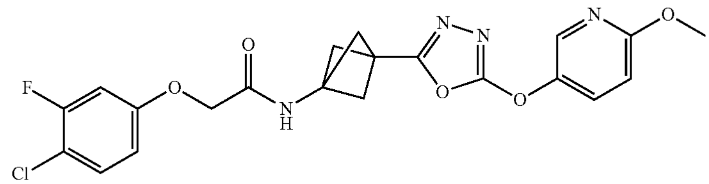 [SMILES: COc1ccc(Oc2nnc(C34CC(NC(=O)COc5ccc(Cl)c(F)c5)(C3)C4)o2)cn1] |
| 121 | 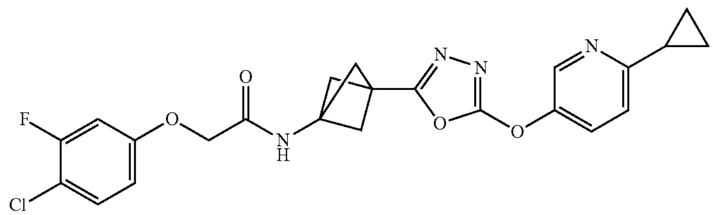 [SMILES: O=C(COc1ccc(Cl)c(F)c1)NC12CC(c3nnc(Oc4ccc(C5CC5)nc4)o3)(C1)C2] |
| 122 | 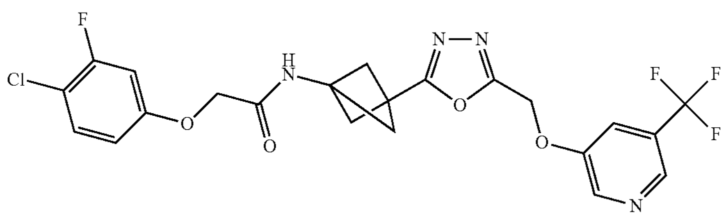 [SMILES: O=C(COc1ccc(Cl)c(F)c1)NC12CC(c3nnc(COc4cncc(C(F)(F)F)c4)o3)(C1)C2] |
| 123 | 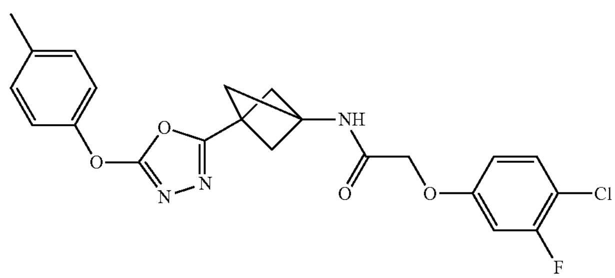 [SMILES: Cc1ccc(Oc2nnc(C34CC(NC(=O)COc5ccc(Cl)c(F)c5)(C3)C4)o2)cc1] |
| 124 | 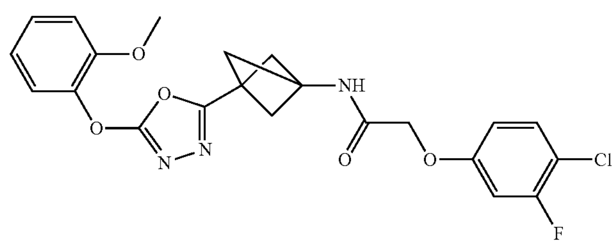 [SMILES: COc1ccccc1Oc1nnc(C23CC(NC(=O)COc4ccc(Cl)c(F)c4)(C2)C3)o1] |
| 125 | 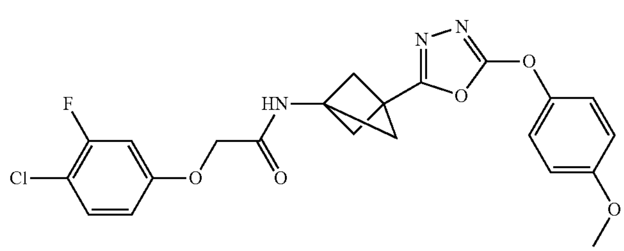 [SMILES: COc1ccc(Oc2nnc(C34CC(NC(=O)COc5ccc(Cl)c(F)c5)(C3)C4)o2)cc1] |

TABLE 1-continued

Exemplary compounds of the invention

| Compound No. | Structure |
| --- | --- |
| 126 | 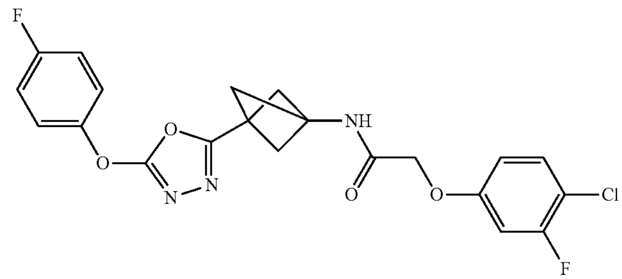 [SMILES: O=C(COc1ccc(Cl)c(F)c1)NC12CC(c3nnc(Oc4ccc(F)cc4)o3)(C1)C2] |
| 127 | 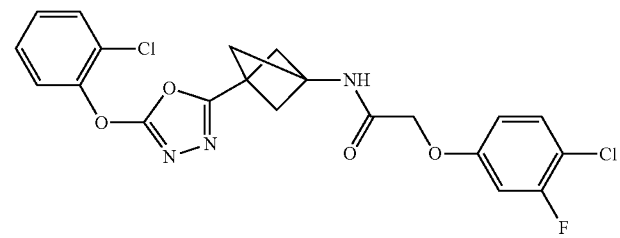 [SMILES: O=C(COc1ccc(Cl)c(F)c1)NC12CC(c3nnc(Oc4ccccc4Cl)o3)(C1)C2] |
| 128 | 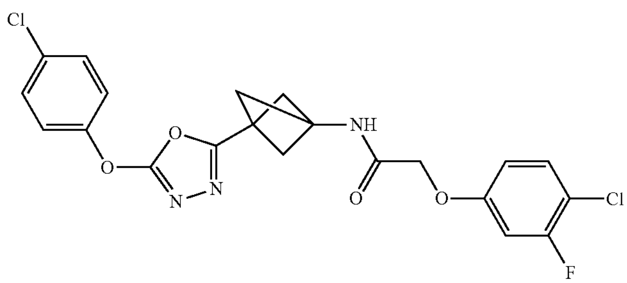 [SMILES: O=C(COc1ccc(Cl)c(F)c1)NC12CC(c3nnc(Oc4ccc(Cl)cc4)o3)(C1)C2] |
| 129 | 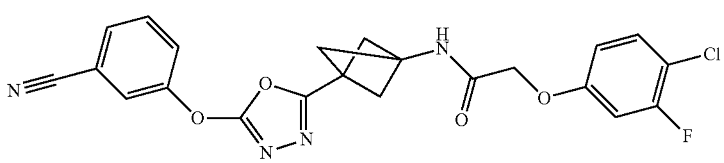 [SMILES: N#Cc1cccc(Oc2nnc(C34CC(NC(=O)COc5ccc(Cl)c(F)c5)(C3)C4)o2)c1] |
| 130 | 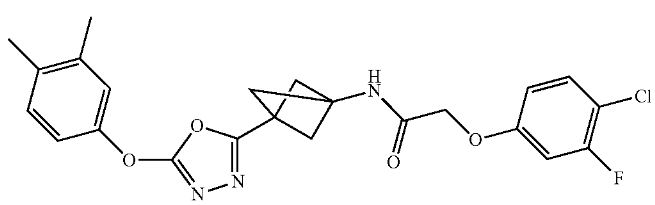 [SMILES: Cc1ccc(Oc2nnc(C34CC(NC(=O)COc5ccc(Cl)c(F)c5)(C3)C4)o2)cc1C] |
| 131 | 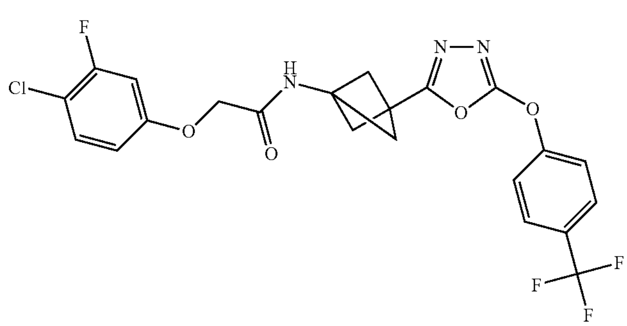 [SMILES: O=C(COc1ccc(Cl)c(F)c1)NC12CC(c3nnc(Oc4ccc(C(F)(F)F)cc4)o3)(C1)C2] |

TABLE 1-continued

Exemplary compounds of the invention

| Compound No. | Structure |
|---|---|
| 132 | 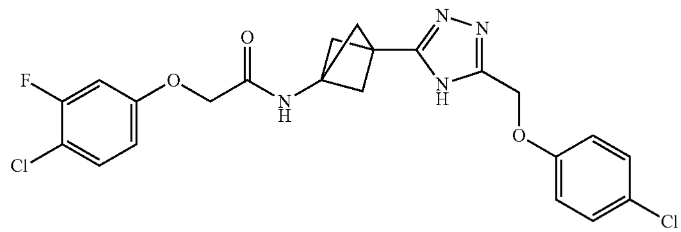 [SMILES: O=C(COc1ccc(Cl)c(F)c1)NC12CC(c3nnc(COc4ccc(Cl)cc4)[nH]3)(C1)C2] |
| 133 | 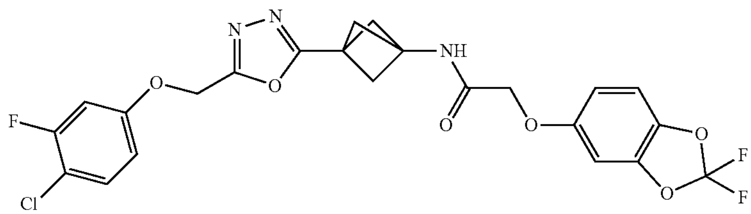 [SMILES: O=C(COc1ccc2c(c1)OC(F)(F)O2)NC12CC(c3nnc(COc4ccc(Cl)c(F)c4)o3)(C1)C2] |
| 134 | 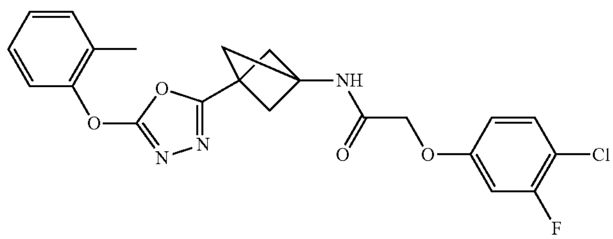 [SMILES: Cc1ccccc1Oc1nnc(C23CC(NC(=O)COc4ccc(Cl)c(F)c4)(C2)C3)o1] |
| 135 | 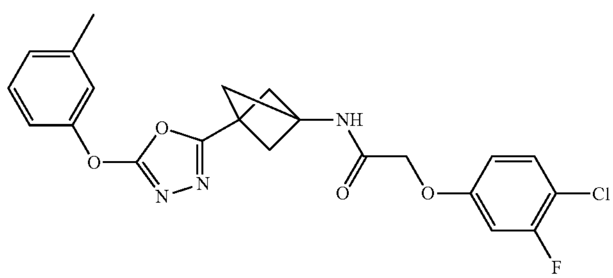 [SMILES: Cc1cccc(Oc2nnc(C34CC(NC(=O)COc5ccc(Cl)c(F)c5)(C3)C4)o2)c1] |
| 136 | 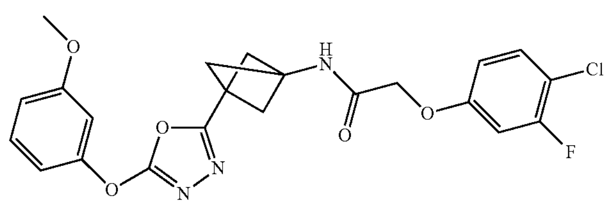 [SMILES: COc1cccc(Oc2nnc(C34CC(NC(=O)COc5ccc(Cl)c(F)c5)(C3)C4)o2)c1] |
| 137 | 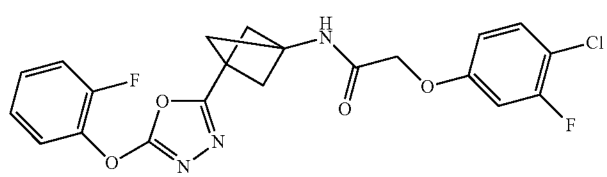 [SMILES: O=C(COc1ccc(Cl)c(F)c1)NC12CC(c3nnc(Oc4ccccc4F)o3)(C1)C2] |
| 138 | 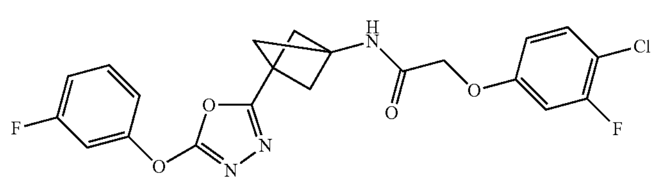 [SMILES: O=C(COc1ccc(Cl)c(F)c1)NC12CC(c3nnc(Oc4cccc(F)c4)o3)(C1)C2] |

TABLE 1-continued

Exemplary compounds of the invention

| Compound No. | Structure |
|---|---|
| 139 | 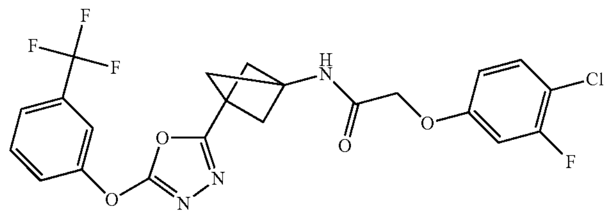 [SMILES: O=C(COc1ccc(Cl)c(F)c1)NC12CC(c3nnc(Oc4cccc(C(F)(F)F)c4)o3)(C1)C2] |
| 140 | 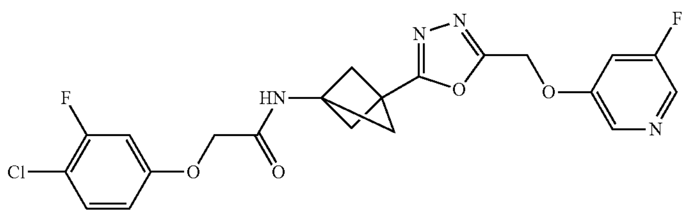 [SMILES: O=C(COc1ccc(Cl)c(F)c1)NC12CC(c3nnc(COc4cncc(F)c4)o3)(C1)C2] |
| 141 | 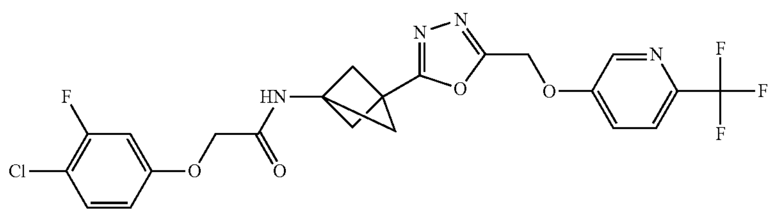 [SMILES: O=C(COc1ccc(Cl)c(F)c1)NC12CC(c3nnc(COc4ccc(C(F)(F)F)nc4)o3)(C1)C2] |
| 142 | 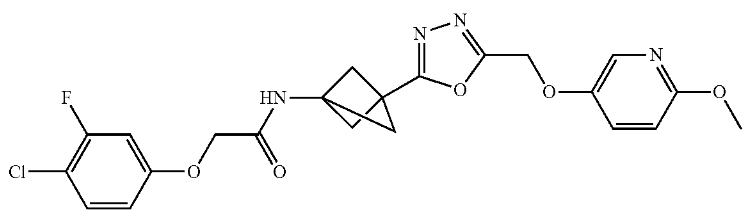 [SMILES: COc1ccc(OCc2nnc(C34CC(NC(=O)COc5ccc(Cl)c(F)c5)(C3)C4)o2)cn1] |
| 143 | 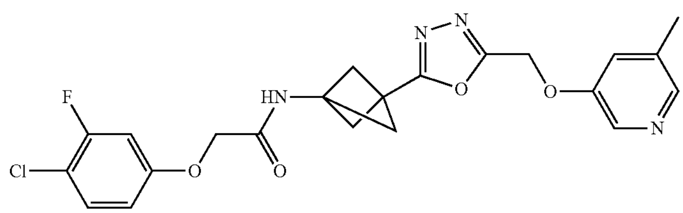 [SMILES: Cc1cncc(OCc2nnc(C34CC(NC(=O)COc5ccc(Cl)c(F)c5)(C3)C4)o2)c1] |
| 144 | 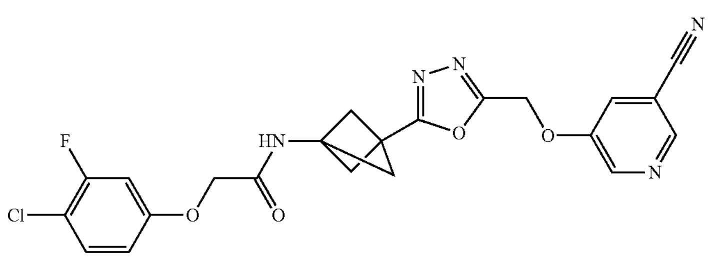 [SMILES: N#Cc1cncc(OCc2nnc(C34CC(NC(=O)COc5ccc(Cl)c(F)c5)(C3)C4)o2)c1] |
| 145 | 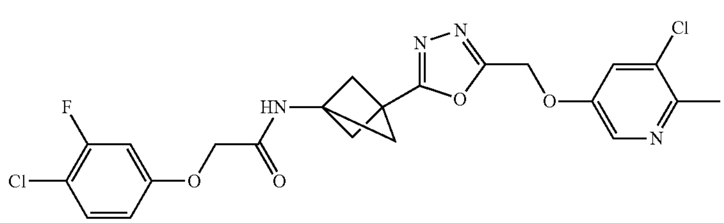 [SMILES: Cc1ncc(OCc2nnc(C34CC(NC(=O)COc5ccc(Cl)c(F)c5)(C3)C4)o2)cc1Cl] |

TABLE 1-continued

Exemplary compounds of the invention

| Compound No. | Structure |
| --- | --- |
| 146 | 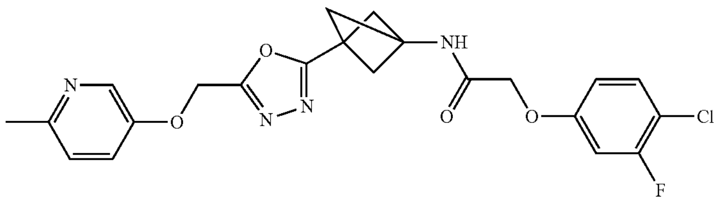 [SMILES: Cc1ccc(OCc2nnc(C34CC(NC(=O)COc5ccc(Cl)c(F)c5)(C3)C4)o2)cn1] |
| 147 | 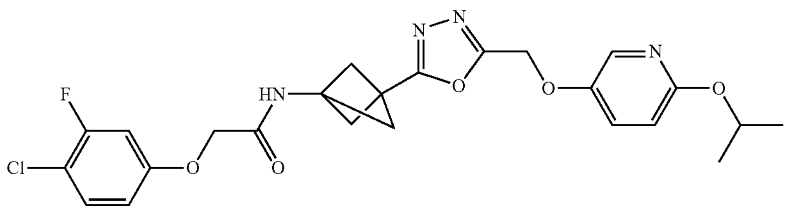 [SMILES: CC(C)Oc1ccc(OCc2nnc(C34CC(NC(=O)COc5ccc(Cl)c(F)c5)(C3)C4)o2)cn1] |
| 148 | 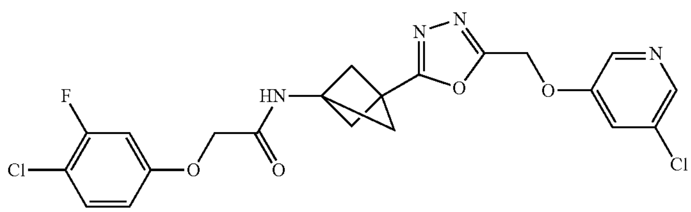 [SMILES: O=C(COc1ccc(Cl)c(F)c1)NC12CC(c3nnc(COc4cncc(Cl)c4)o3)(C1)C2] |
| 149 | 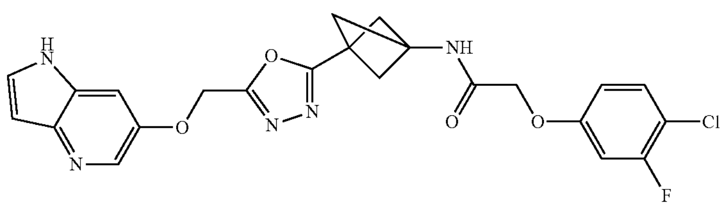 [SMILES: O=C(COc1ccc(Cl)c(F)c1)NC12CC(c3nnc(COc4cnc5cc[nH]c5c4)o3)(C1)C2] |
| 150 | 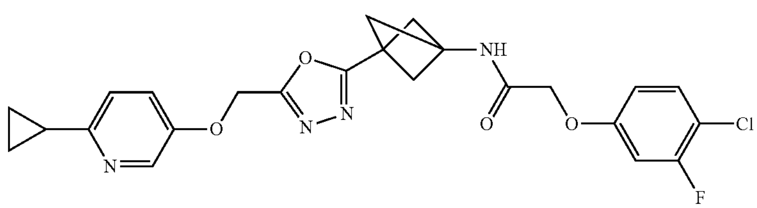 [SMILES: O=C(COc1ccc(Cl)c(F)c1)NC12CC(c3nnc(COc4ccc(C5CC5)nc4)o3)(C1)C2] |
| 151 | 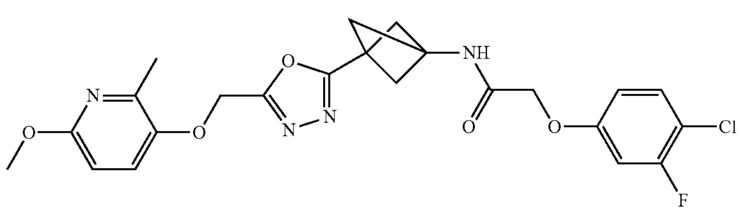 [SMILES: COc1ccc(OCc2nnc(C34CC(NC(=O)COc5ccc(Cl)c(F)c5)(C3)C4)o2)c(C)n1] |
| 152 | 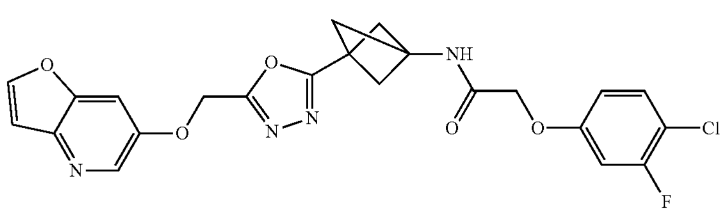 [SMILES: O=C(COc1ccc(Cl)c(F)c1)NC12CC(c3nnc(COc4cnc5ccoc5c4)o3)(C1)C2] |

TABLE 1-continued

Exemplary compounds of the invention

| Compound No. | Structure |
|---|---|
| 153 | 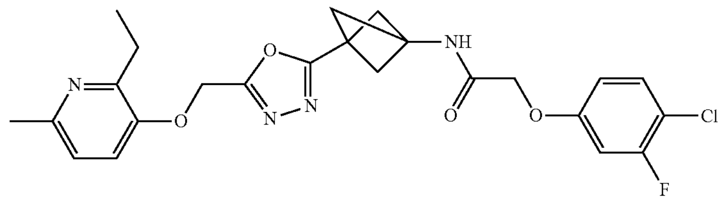 [SMILES: CCc1nc(C)ccc1OCc1nnc(C23CC(NC(=O)COc4ccc(Cl)c(F)c4)(C2)C3)o1] |
| 154 | 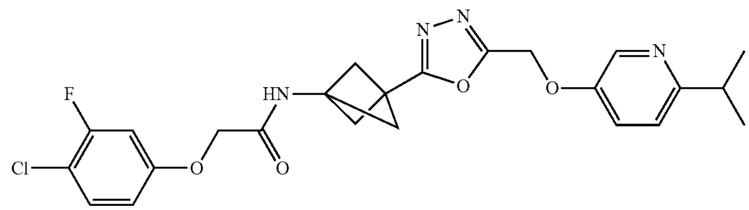 [SMILES: CC(C)c1ccc(OCc2nnc(C34CC(NC(=O)COc5ccc(Cl)c(F)c5)(C3)C4)o2)cn1] |
| 155 | 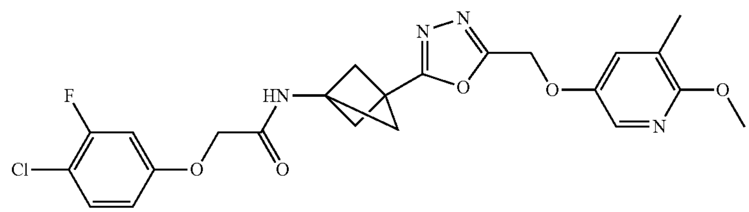 [SMILES: COc1ncc(OCc2nnc(C34CC(NC(=O)COc5ccc(Cl)c(F)c5)(C3)C4)o2)cc1C] |
| 156 | 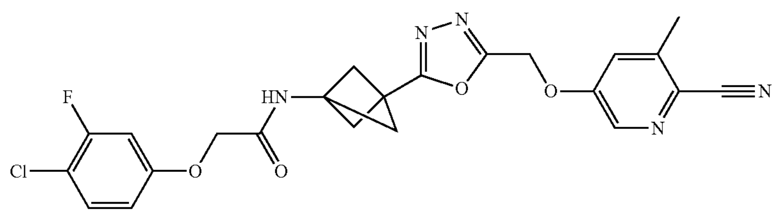 [SMILES: Cc1cc(OCc2nnc(C34CC(NC(=O)COc5ccc(Cl)c(F)c5)(C3)C4)o2)cnc1C#N] |
| 157 | 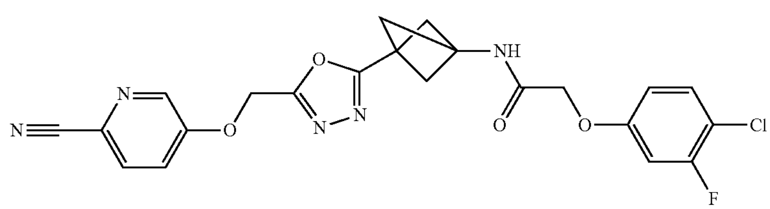 [SMILES: N#Cc1ccc(OCc2nnc(C34CC(NC(=O)COc5ccc(Cl)c(F)c5)(C3)C4)o2)cn1] |
| 158 | 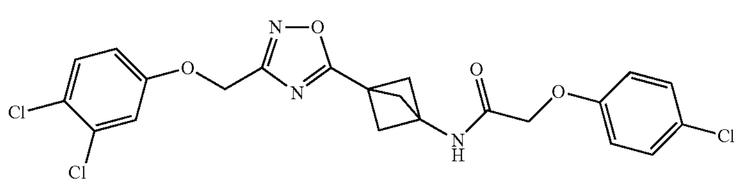 [SMILES: O=C(COc1ccc(Cl)cc1)NC12CC(c3nc(COc4ccc(Cl)c(Cl)c4)no3)(C1)C2] |
| 159 | 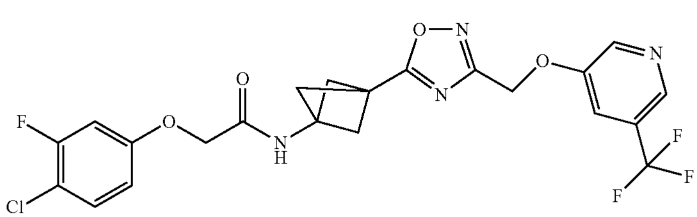 [SMILES: O=C(COc1ccc(Cl)c(F)c1)NC12CC(c3nc(COc4cncc(C(F)(F)F)c4)no3)(C1)C2] |

TABLE 1-continued

Exemplary compounds of the invention

| Compound No. | Structure |
|---|---|
| 160 | 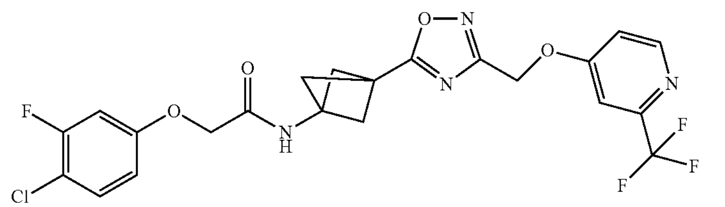 [SMILES: O=C(COc1ccc(Cl)c(F)c1)NC12CC(c3nc(COc4ccnc(C(F)(F)F)c4)no3)(C1)C2] |
| 161 | 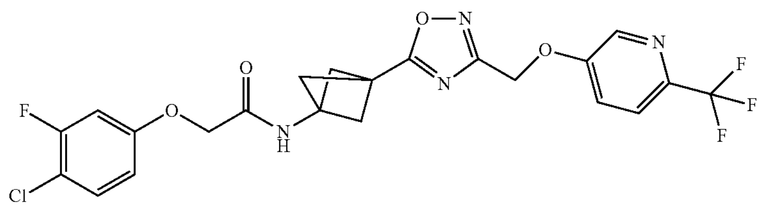 [SMILES: O=C(COc1ccc(Cl)c(F)c1)NC12CC(c3nc(COc4ccc(C(F)(F)F)nc4)no3)(C1)C2] |
| 162 | 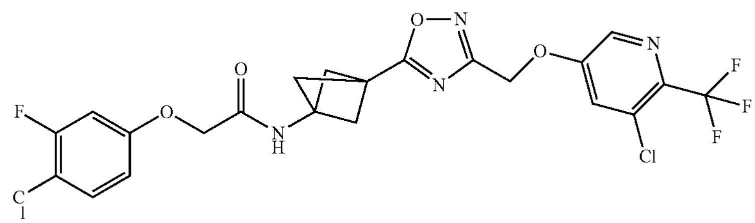 [SMILES: O=C(COc1ccc(Cl)c(F)c1)NC12CC(c3nc(COc4cnc(C(F)(F)F)c(Cl)c4)no3)(C1)C2] |
| 163 | 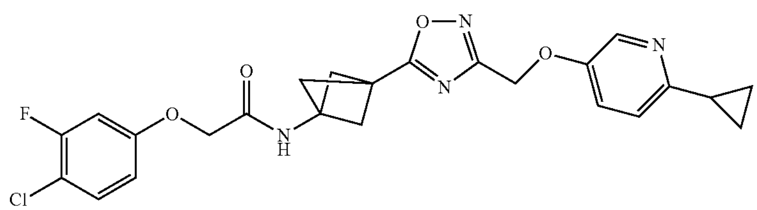 [SMILES: O=C(COc1ccc(Cl)c(F)c1)NC12CC(c3nc(COc4ccc(C5CC5)nc4)no3)(C1)C2] |
| 164 | 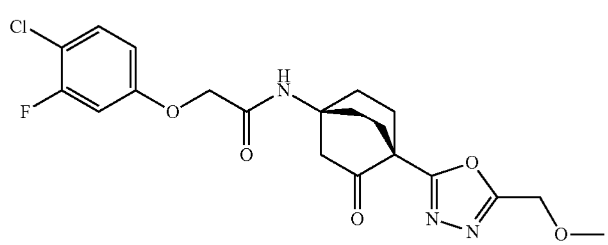 [SMILES: COCc1nnc([C@]23CC[C@](NC(=O)COc4ccc(Cl)c(F)c4)(CC2)CC3=O)o1] |
| 165 | 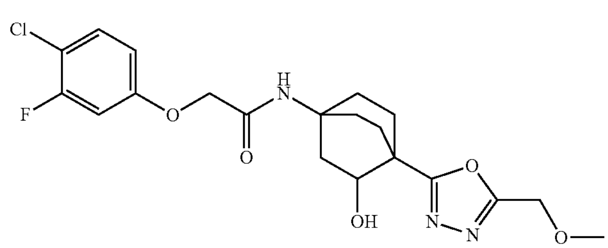 [SMILES: COCc1nnc(C23CCC(NC(=O)COc4ccc(Cl)c(F)c4)(CC2)CC3O)o1] |

TABLE 1-continued

Exemplary compounds of the invention

| Compound No. | Structure |
|---|---|
| 166 | 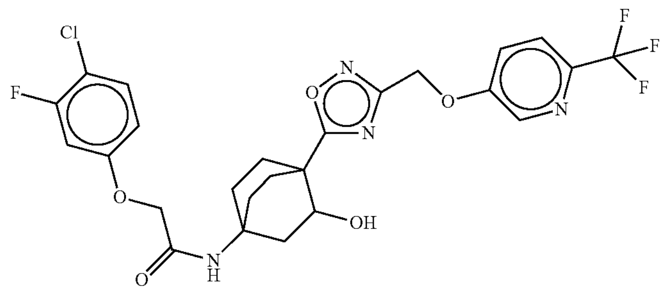 |
| 167 | 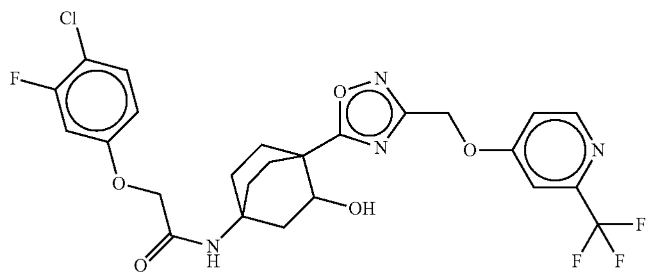 |
| 168 | 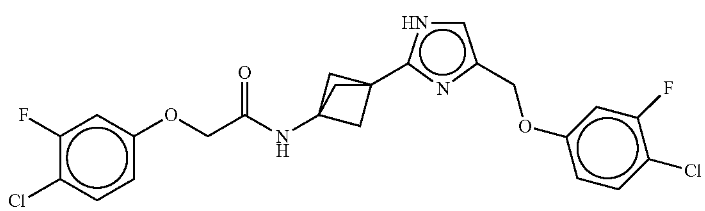 |
| 169 | 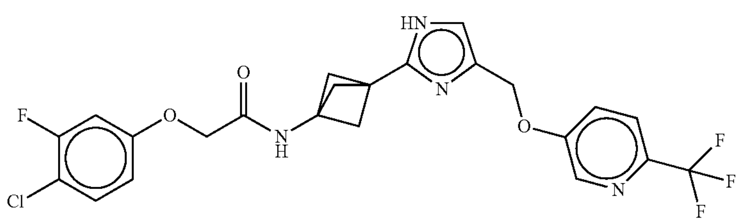 |
| 170 | 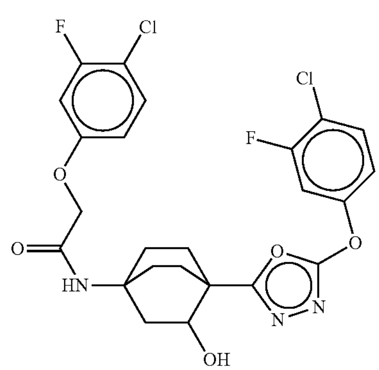 |

Methods of Making Exemplary Compounds

The compounds of the invention may be better understood in connection with the following synthetic schemes and methods which illustrate a means by which the compounds can be prepared. The compounds of this invention can be prepared by a variety of synthetic procedures. Representative synthetic procedures are shown in, but not limited to, Schemes 1-12. The variables A, D, Z, $L^1$, $L^2$, and $R^1$ are defined as detailed herein, e.g., in the Summary.

Scheme 1
Representative scheme for synthesis of exemplary compounds of the invention

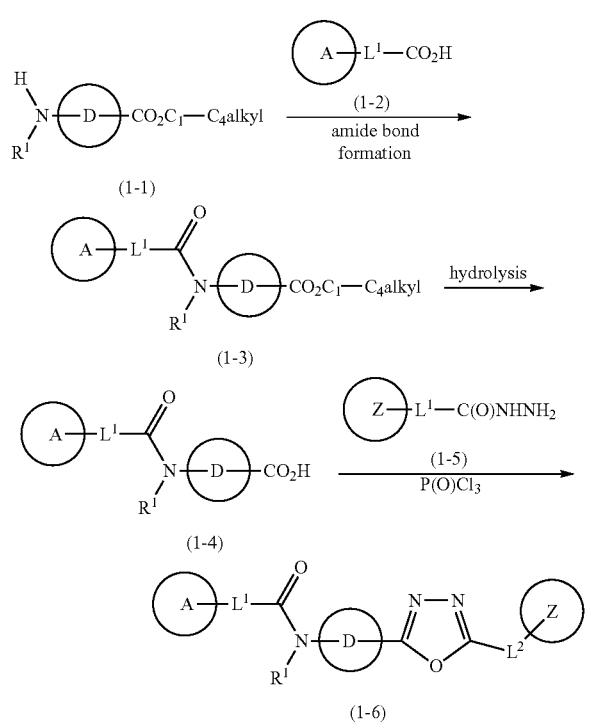

As shown in Scheme 1, compounds of formula (1-1) can be converted to compounds of formula (1-6). Amines of formula (1-1) can be coupled with carboxylic acids of formula (1-2) under amide bond forming conditions to give amides of formula (1-3). Examples of conditions known to generate amides from a mixture of a carboxylic acid and an amine include but are not limited to adding a coupling reagent such as N-(3-dimethylaminopropyl)-N-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate or 2-(3H-[1,2,3]triazolo[4,5-b]pyridin-3-yl)-1,1,3,3-tetramethylisouronium hexafluorophosphate(V) or 2-(7-aza-1H-benzotriazole-1-yl)-1,1,3,3-tetramethyluronium hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), 2,4,6-tripropyl-1,3,5,2,4,6-trioxatriphosphinane 2,4,6-trioxide (T3P®), (1-cyano-2-ethoxy-2-oxoethylidenaminooxy)-dimethylamino-morpholino-carbenium hexafluorophosphate (COMU®), and fluoro-N,N,N',N'-tetramethylformamidinium hexafluorophosphate. The coupling reagents may be added as a solid, a solution, or as the reagent bound to a solid support resin.

In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, and ethyl acetate.

Alternatively, carboxylic acids of formula (1-2) can be converted to the corresponding acid chlorides by reaction with thionyl chloride, $PCl_3$, $PCl_5$, cyanuric chloride, or oxalyl chloride. The reactions with thionyl chloride and oxalyl chloride can be catalyzed with N,N-dimethylformamide at ambient temperature in a solvent such as dichloromethane. The resultant acid chlorides can then reacted with amines of formula (1-1) optionally in the presence of a base such as a tertiary amine base such as but not limited to triethylamine or diisopropylethylamine or an aromatic base such as pyridine, at room temperature in a solvent such as dichloromethane to give amides of formula (1-3). The esters in compounds of formula (1-3) can be hydrolyzed to compounds of formula (1-4). For example, esters of formula (1-3) can be treated with a base such as lithium hydroxide, sodium hydroxide, or potassium hydroxide in a solvent such as methanol, ethanol, tetrahydrofuran or a with a mixture of tetrahydrofuran and water at ambient temperature or heated from 0.5 to 16 hours to give compounds of formula (1-4). Compounds of formula (1-4) can be reacted with compounds of formula (1-5) in heated phosphorus oxychloride to give compound of formula (1-6). Alternatively, compounds of formula (1-4) can also be reacted with compounds of formula (1-5) under the amide bond coupling conditions described to make compounds of formula (1-3). Following the coupling, the intermediate can be cyclized and dehydrated using 4-methylbenzene-1-sulfonyl chloride in the presence of a tertiary amine base such as N,N-diisopropylethylamine in heated acetonitrile to give compounds of formula (1-6). Compounds of formula (1-6) are representative of compounds of formula (I).

Scheme 2
Representative scheme for synthesis of exemplary compounds of the invention

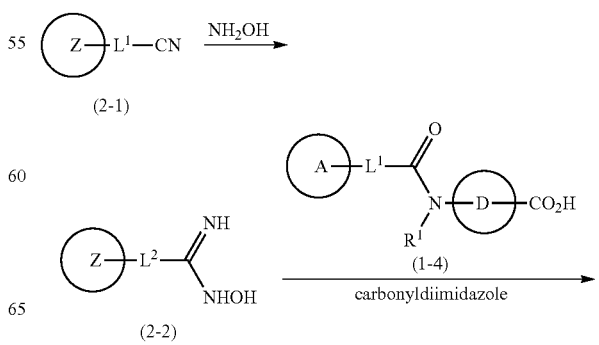

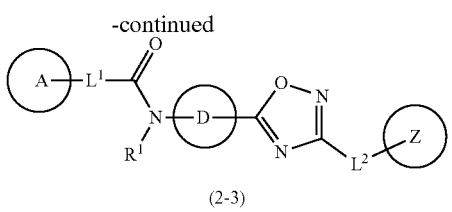

(2-3)

As depicted in Scheme 2, compounds of formula (2-1) can be transformed to compounds of formula (2-3). Compounds of formula (2-1) can be treated with hydroxylamine hydrochloride in the presence of a base such as but not limited to N,N-diisopropylethylamine in a solvent such as heated ethanol to give compounds of formula (2-2). Compounds of formula (1-4) can be treated with carbonyldiimidazole in a solvent such as but not limited to N,N-dimethylformamide at or near ambient temperature. Subsequently, compounds of (2-2) can be added, and the resultant mixture can be heated to 70-100° C. for 2-24 hours to give compounds of formula (2-3). Compounds of formula (2-3) are representative of compounds of formula (I).

Compounds of formula (3-2) can also be prepared by reacting compounds of formula (3-1) with carbonyldiimidazole in a solvent such as N,N-dimethylformamide at or near ambient temperature and then with a compound of formula (2-2). Compounds of formula (3-2) can be heated (80-130° C.) in a solvent such as but not limited to N,N-dimethylformamide to give compounds of formula (3-3). The protecting group can then be removed from compounds of formula (3-3) under conditions known to one of skill in the art and dependent on the particular protecting group. Subsequently, the exposed amine can be coupled with carboxylic acids of formula (1-2) using the coupling conditions described in Scheme 1 to give compounds of formula (2-3). Compounds of formula (2-3) are representative of compounds of formula (I).

Scheme 3
Representative scheme for synthesis of exemplary compounds of the invention.

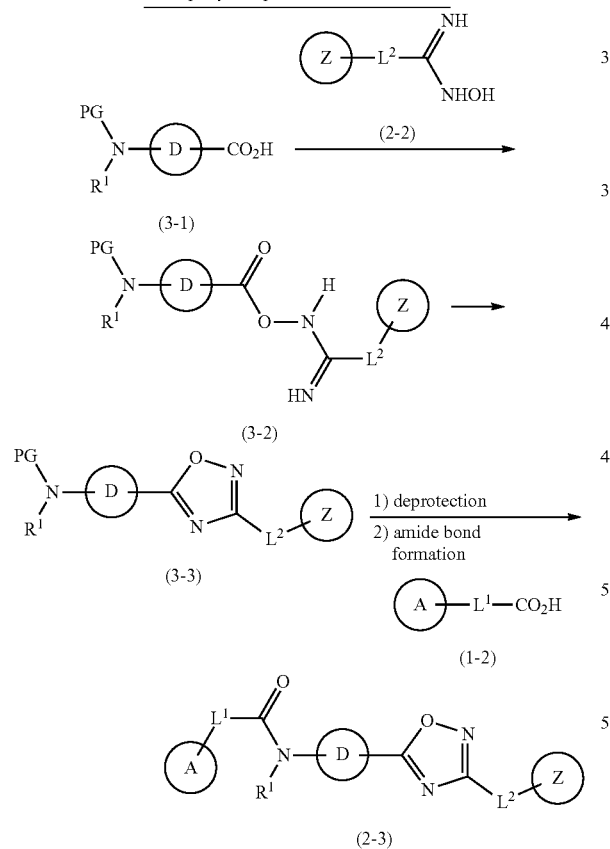

As shown in Scheme 3, compounds of formula (2-3) can also be derived from compounds of formula (3-1). Compounds of formula (3-1), wherein in PG is a protecting group known to one of skill in the art, can be coupled with compounds of formula (2-2) using the coupling conditions described in Scheme 1 to give compounds of formula (3-2).

Scheme 4
Representative scheme for synthesis of exemplary compounds of the invention.

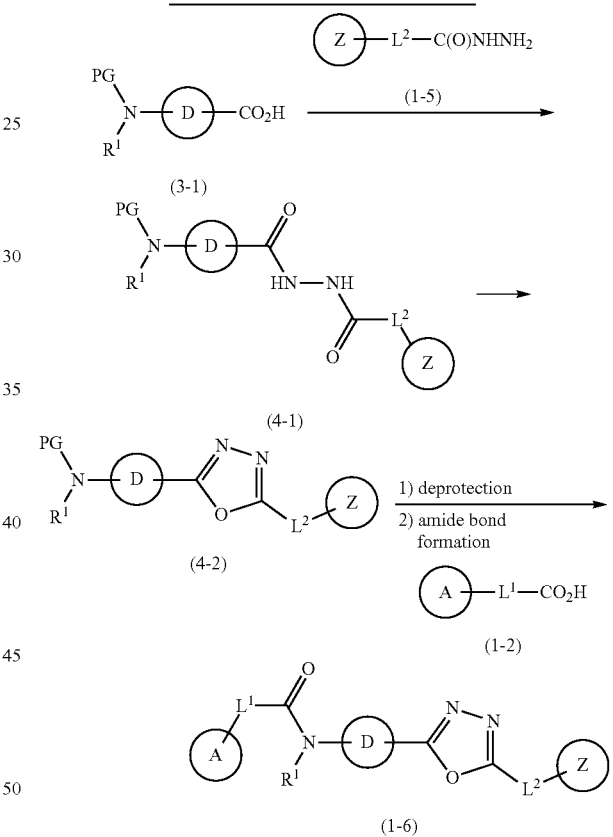

As shown in Scheme 4, compounds of formula (3-1) can also be converted to compounds of formula (1-6). Compounds of formula (3-1), wherein PG is an amine protecting group, can be coupled with compounds of formula (1-5) using the coupling conditions described in Scheme 1 to give compounds of formula (4-1). Compounds of formula (4-1) can be treated with 2,4,6-tripropyl-1,3,5,2,4,6-trioxatriphosphinane 2,4,6-trioxide and trimethylamine in a heated solvent such as but not limited to ethyl acetate to give compounds of formula (4-2). The protecting group can then be removed from compounds of formula (4-2) under conditions known to one of skill in the art and dependent on the particular protecting group. Subsequently, the exposed amine can be coupled with carboxylic acids of formula (1-2)

using the coupling conditions described in Scheme 1 to give compounds of formula (1-6). Compounds of formula (1-6) are representative of compounds of formula (I).

Scheme 5
Representative scheme for synthesis of exemplary compounds of the invention.

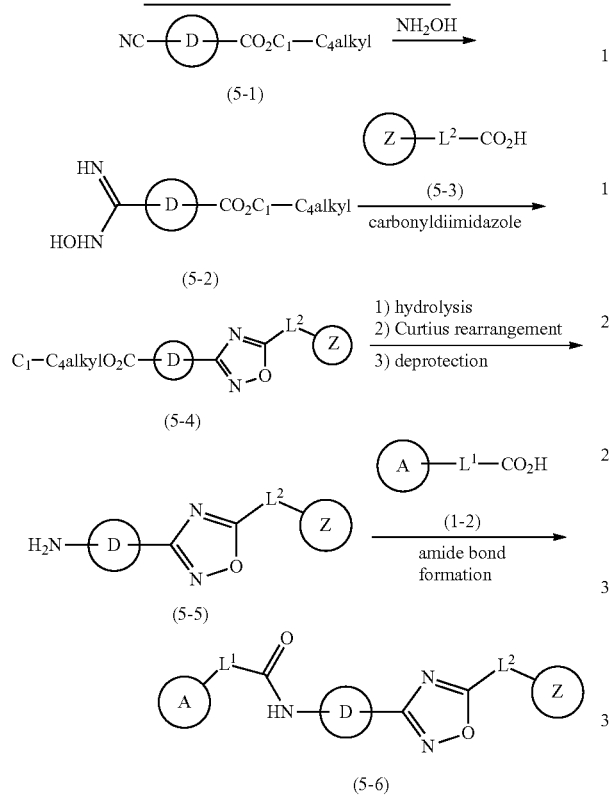

As shown in Scheme 5, compounds of formula (5-6) can be derived from compounds of formula (5-1). Compounds of formula (5-1) can be treated with aqueous hydroxylamine heated in a solvent such as but not limited to ethanol to give compounds of formula (5-2). Compounds of formula (5-3) can be treated with carbonyldiimidazole in a solvent such as but not limited to N,N-dimethylformamide. Subsequently, compounds of formula (5-2) can be added and the mixture heated to give compounds of formula (5-4). Compounds of formula (5-4) can be converted to compounds of formula (5-5) in a three-step process. In the first step, esters of formula (5-4) can be hydrolyzed to the corresponding carboxylic acid. For example, esters of formula (5-4) can be treated with a base such as lithium hydroxide, sodium hydroxide, or potassium hydroxide in a solvent such as methanol, ethanol, tetrahydrofuran or a with a mixture of tetrahydrofuran and water at ambient temperature or heated from 0.5 to 16 hours to give the corresponding carboxylic acids. The carboxylic acid can then be reacted under Curtius rearrangement reaction conditions to give a protected amine. In the third step, the protecting group can be removed under conditions known to one of skill in the art dependent on the protecting group to give compounds of formula (5-5). Compounds of formula (5-5) can be coupled with compounds of formula (1-2) under the amide bond forming conditions described in Scheme 1 to give compounds of formula (5-6). Compound of formula (5-6) are representative of compounds of formula (I).

Scheme 6
Representative scheme for synthesis of exemplary compounds of the invention.

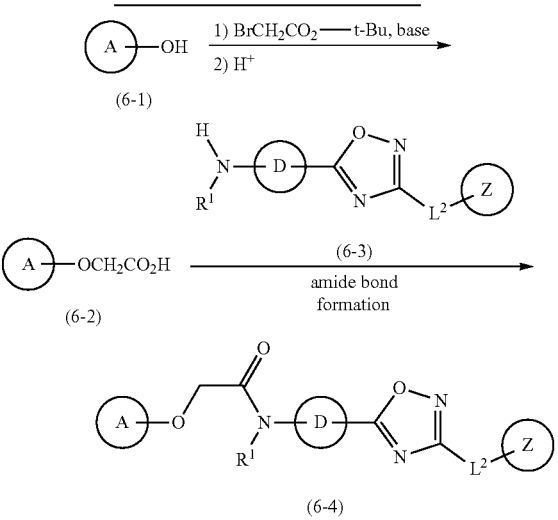

As shown in Scheme 6, compounds of formula (6-1) can be converted to compounds of formula (6-4). Compounds of formula (6-1) can be treated with tert-butyl 2-bromoacetate in the presence of a base such as but not limited to potassium carbonate in a solvent such as but not limited to optionally heated N,N-dimethylformamide. Subsequent treatment with an acid, e.g. hydrochloric acid in dioxane or trifluoroacetic acid in dichloromethane gives compounds of formula (6-2). Compounds of formula (6-2) can be coupled with compounds of formula (6-3) under the amide bond forming reaction conditions described in Scheme 1 to give compounds of formula (6-4). Compounds of formula (6-3) are obtained as shown in Scheme 3 with the deprotection of compounds of formula (3-3). Compounds of formula (6-4) are representative of compounds of formula (I).

Scheme 7
Representative scheme for synthesis of exemplary compounds of the invention.

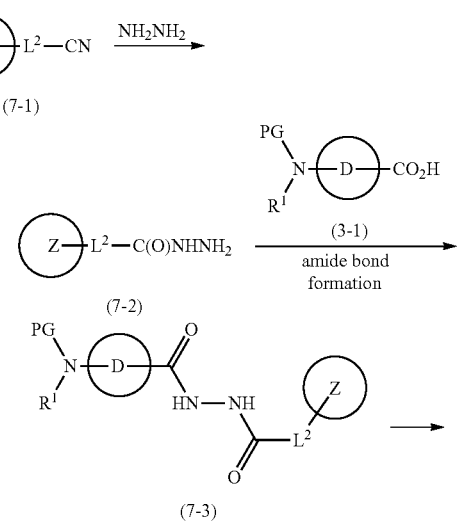

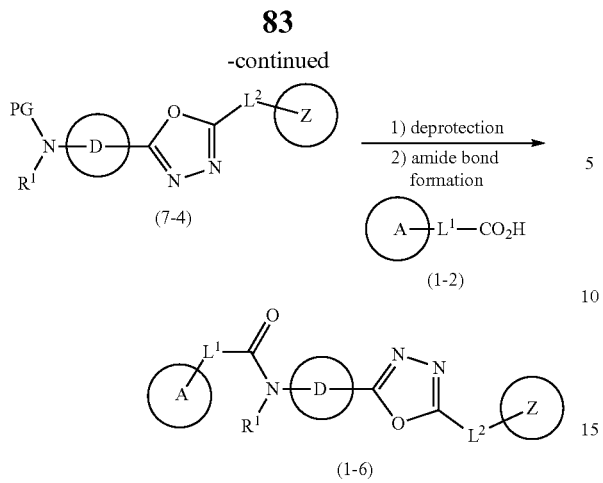

As shown in Scheme 7, compounds of formula (7-1) can be converted to compounds of formula (1-6). Compounds of formula (7-1) can be treated with hydrazine hydrate in heated ethanol to give compounds of formula (7-2). Compounds of formula (7-2) can be coupled with carboxylic acids of formula (3-1), wherein PG is an amine protecting group, under the coupling conditions described in Scheme 1 to give compounds of formula (7-3). Compounds of formula (7-3) can be reacted with 4-methylbenzene-1-sulfonyl chloride in the presence of a base such as but not limited to N,N-diisopropylethylamine in a solvent such as but not limited to acetonitrile to provide compounds of formula (7-4). The protecting group can then be removed from compounds of formula (7-4) under conditions known to one of skill in the art and dependent on the particular protecting group. Subsequently, the exposed amine can be coupled with carboxylic acids of formula (1-2) using the coupling conditions described in Scheme 1 to give compounds of formula (1-6). Compounds of formula (1-6) are representative of compounds of formula (I).

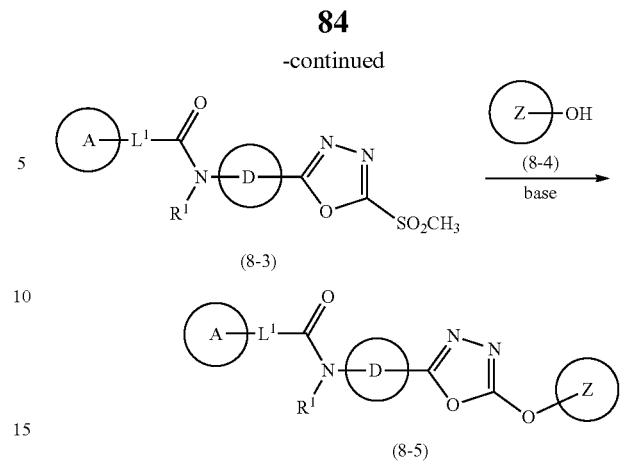

As shown in Scheme 8, compounds of formula (8-5) can be derived from compounds of formula (1-3). Compounds of formula (1-3) can be treated with hydrazine hydrate in a solvent such as but not limited to heated ethanol to give compounds of formula (8-1). Compounds of formula (8-1) can be treated with carbon disulfide in the presence of a base such as potassium hydroxide in a solvent such as but not limited to heated methanol to give compounds of formula (8-2). Compounds of formula (8-2) can be alkylated with methyl iodide in the presence of a base such as potassium carbonate in a solvent such as but not limited to N,N-dimethylformamide. Subsequent treatment with potassium permanganate in a mixture of water and acetic acid at or near 0° C. gives compounds of formula (8-3). Compounds of formula (8-3) can be reacted with compounds of formula (8-4) in the presence of a base such as potassium carbonate in a heated solvent such as but not limited to N,N-dimethylformamide to give compounds of formula (8-5). Compounds of formula (8-5) are representative of compounds of formula (I).

Scheme 8
Representative scheme for synthesis of exemplary compounds of the invention.

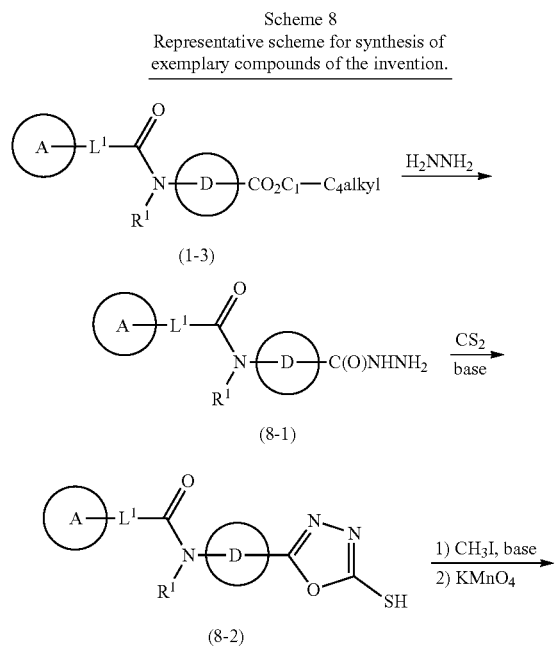

Scheme 9
Representative scheme for synthesis of exemplary compounds of the invention.

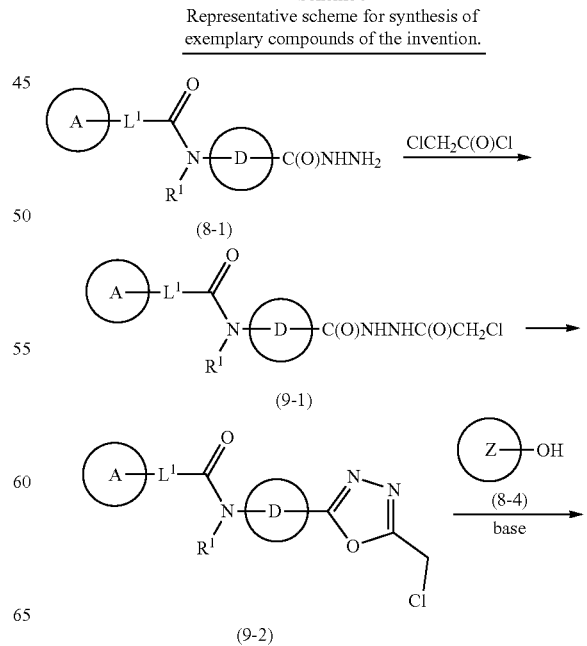

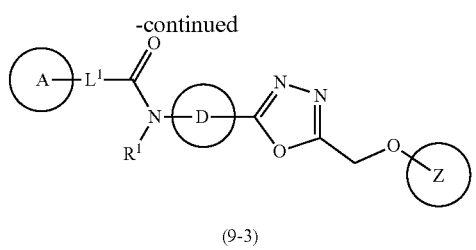

(9-3)

As shown in Scheme 9, compounds of formula (9-3) can be derived from compounds of formula (8-1). Compounds of formula (8-1) can by reacted with 2-chloroacetyl chloride in the presence of a base such as triethylamine in a solvent such as but not limited to tetrahydrofuran to give compounds of formula (9-1). Compounds of formula (9-1) can be reacted with 4-methylbenzene-1-sulfonyl chloride in the presence of a base such as N,N-diisopropylethylamine in a solvent such as but not limited to acetonitrile to give compounds of formula (9-2). Compounds of formula (9-2) can be reacted with compounds of formula (8-4) in the presence of a base such as potassium carbonate in a heated solvent such as but not limited to N,N-dimethylformamide to give compounds of formula (9-3). Compounds of formula (9-3) are representative of compounds of formula (I).

Scheme 10
Representative scheme for synthesis of exemplary compounds of the invention.

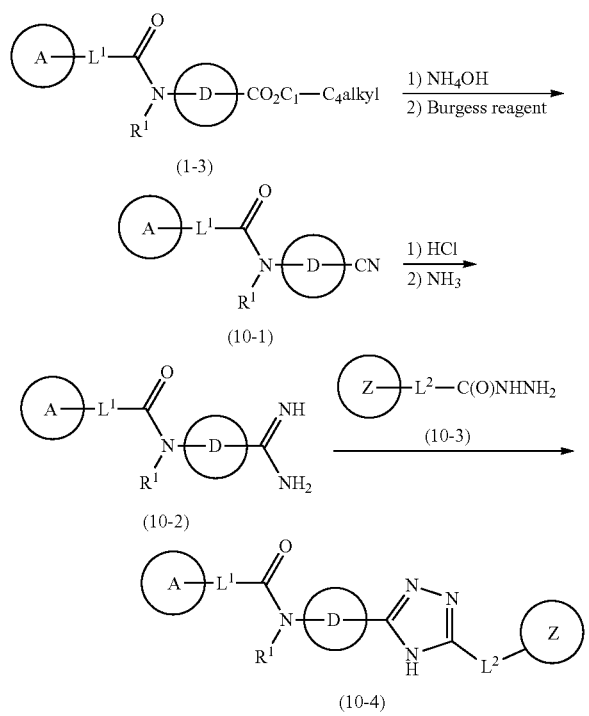

As shown in Scheme 10, compound of formula (10-4) can be derived from compounds of formula (1-3). Compounds of (1-3) can be converted in two steps to compounds of formula (10-1). Compounds of formula (1-3) can be treated with ammonium hydroxide in a solvent such as but not limited to methanol to give an intermediate primary amide. The intermediate primary amide can then be reacted with Burgess reagent in a solvent such as tetrahydrofuran to give compounds of formula (10-1). Compounds of formula (10-1) can be treated with hydrochloric acid in dioxane in a solvent such as ethanol followed by ammonia in methanol to deliver compounds of formula (10-2). Compounds of formula (10-2) can be reacted with compounds of formula (10-3) in a solvent such as but not limited to methanol heated to 60-90° C. in a sealed tube to give compounds of formula (10-4). Compounds of formula (10-4) are representative of compounds of formula (I).

Scheme 11
Representative scheme for synthesis of exemplary compounds of the invention.

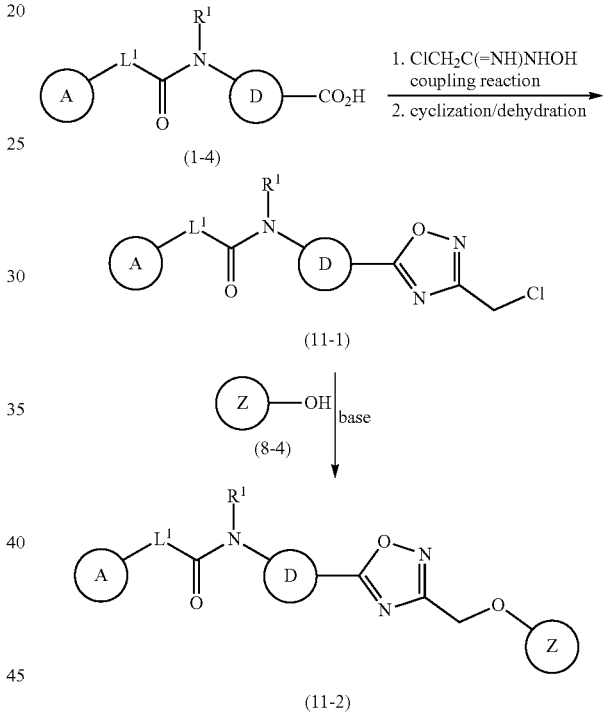

As shown in Scheme 11, compounds of formula (11-2) can be derived from compounds of formula (1-4). Compounds of formula (1-4) can be coupled with 2-chloro-N-hydroxyacetimidamide using reagents such as but not limited to 1H-benzo[d][1,2,3]triazol-1-ol hydrate, N-ethyl-N-isopropylpropan-2-amine and 2-(3H-[1,2,3]triazolo[4,5-b]pyridin-3-yl)-1,1,3,3-tetramethylisouronium tetrafluoroborate in a solvent such as N,N-dimethylformamide. The coupling product can then be cyclized and dehydrated in refluxing toluene using a Dean-Stark apparatus to supply compounds of formula (11-1). Compounds of formula (11-1) can be reacted with alcohols of formula (8-4) in the presence of a base such as potassium carbonate and optional potassium iodide in heated acetone to give compounds of formula (11-2). The heating may be achieved conventionally or with microwave irradiation. Compounds of formula (11-2) are representative of compounds of formula (I).

Scheme 12
Representative scheme for synthesis of exemplary compounds of the invention.

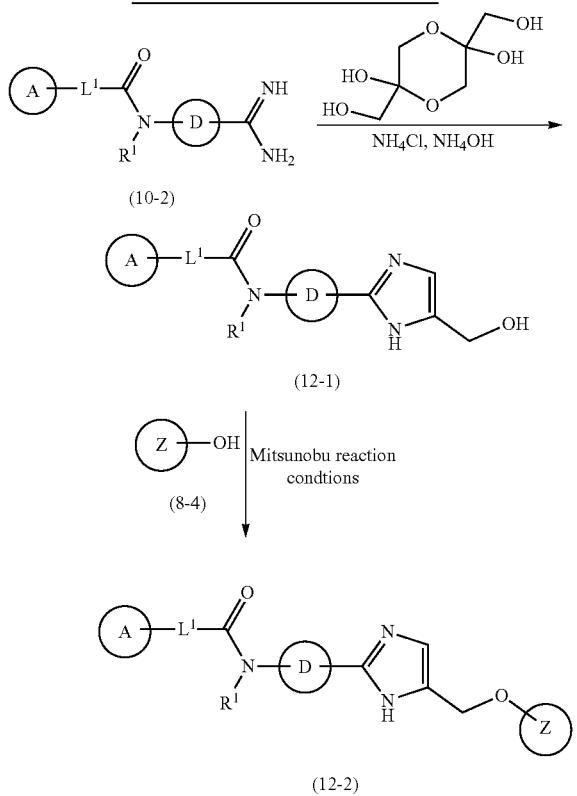

As shown in Scheme 12, compounds of formula (10-2) can be transformed to compounds of formula (12-2). Accordingly, compounds of formula (10-2) can be reacted with 1,3-dihydroxyacetone dimer in the presence of ammonium chloride in heated aqueous ammonium hydroxide to give compounds of formula (12-1). Compounds of formula (12-1) can be reacted with compounds of formula (8-4) under Mitsunobu reaction conditions to give compounds of formula (12-2). Compounds of formula (12-2) are representative of compounds of formula (I).

Pharmaceutical Compositions

The present invention features pharmaceutical compositions comprising a compound of Formula (I) or a pharmaceutically acceptable salt, solvate, hydrate, tautomer, or stereoisomer thereof. In some embodiments, the pharmaceutical composition further comprises a pharmaceutically acceptable excipient. In some embodiments, the compound of Formula (I) or a pharmaceutically acceptable salt, solvate, hydrate, tautomer, stereoisomer thereof is provided in an effective amount in the pharmaceutical composition. In some embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of a compound of Formula (I), the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of a compound of Formula (I).

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound of Formula (I) may also be in micro-encapsulated form.

The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212, 162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. *Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, J. *Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, *Curr. Opin. Biotechnol.* 6:698-708, 1995; Ostro, J. *Hosp. Pharm.* 46: 1576-1587, 1989). The compositions of the present invention can also be delivered as nanoparticles.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

In some embodiments, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein, e.g., a compound of Formula (I) or a pharmaceutically acceptable salt, solvate, hydrate, tautomer, or stereoisomer thereof are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound of Formula (I) or a pharmaceutically acceptable salt, solvate, hydrate, tautomer, or stereoisomer thereof for administration one or more times a day may comprise about 0.0001 mg to about 5000 mg, e.g., from about 0.0001 mg to about 4000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound of Formula (I) or a pharmaceutically acceptable salt, solvate, hydrate, tautomer, or stereoisomer thereof may be at dosage levels sufficient to deliver from about 0.001 mg/kg to about 1000 mg/kg, e.g., about 0.001 mg/kg to about 500 mg/kg, about 0.01 mg/kg to about 250 mg/kg, about 0.1 mg/kg to about 100 mg/kg, about 0.1 mg/kg to about 50 mg/kg, about 0.1 mg/kg to about 40 mg/kg, about 0.1 mg/kg to about 25 mg/kg, about 0.01 mg/kg to about 10 mg/kg, about 0.1 mg/kg to about 10 mg/kg, or about 1 mg/kg to about 50 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, e.g., a compound of Formula (I) or a pharmaceutically acceptable salt, solvate, hydrate, tautomer, or stereoisomer thereof as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Pharmaceutical compositions provided by the present invention include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. eIF2B, eIF2 or component of eIF2α signal transduction pathway or component of phosphorylated eIF2α pathway or the ISR pathway), and/or reducing, eliminating, or slowing the progression of disease symptoms (e.g. symptoms of cancer a neurodegenerative disease, a leukodystrophy, an inflammatory disease, a musculoskeletal disease, a metabolic disease, or a disease or disorder associated with impaired function of eIF2B, eIF2α or a component of the eIF2 pathway or ISR pathway). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. a symptom of cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Also encompassed by the invention are kits (e.g., pharmaceutical packs). The inventive kits may be useful for preventing and/or treating a disease (e.g., cancer, a neurodegenerative disease, a leukodystrophy, an inflammatory disease, a musculoskeletal disease, a metabolic disease, or other disease or condition described herein).

The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound of Formula (I) or a pharmaceutically acceptable salt, solvate, hydrate, tautomer, or stereoisomer thereof, or a pharmaceutical composition thereof. In certain embodiments, the kits are useful in preventing and/or treating a proliferative disease in a subject. In certain embodiments, the kits further include instructions for administering a compound of Formula (I) or a pharmaceutically acceptable salt, solvate, hydrate, tautomer, or stereoisomer thereof, or a pharmaceutical composition thereof, to a subject to prevent and/or treat a disease described herein.

Methods of Treatment

The present invention features compounds, compositions, and methods comprising a compound of Formula (I) or a pharmaceutically acceptable salt, solvate, hydrate, tautomer, or stereoisomer thereof. In some embodiments, the compounds, compositions, and methods are used in the prevention or treatment of a disease, disorder, or condition. Exemplary diseases, disorders, or conditions include, but are not limited to a neurodegenerative disease, a leukodystrophy, cancer, an inflammatory disease, a musculoskeletal disease, or a metabolic disease.

In some embodiments, the disease, disorder, or condition is related to (e.g. caused by) modulation of (e.g., a decrease in) eIF2B activity or level, eIF2α activity or level, or a component of the eIF2 pathway or ISR pathway. In some embodiments, the disease, disorder, or condition is related to modulation of a signaling pathway related to a component of the eIF2 pathway or ISR pathway (e.g., phosphorylation of a component of the eIF2 pathway or ISR pathway). In some embodiments, the disease, disorder, or condition is related to (e.g. caused by) neurodegeneration. In some embodiments, the disease, disorder, or condition is related to (e.g. caused by) neural cell death or dysfunction. In some embodiments, the disease, disorder, or condition is related to (e.g. caused by) glial cell death or dysfunction. In some embodiments, the disease, disorder, or condition is related to (e.g. caused by) an increase in the level or activity of eIF2B, eIF2α, or a component of the eIF2 pathway or ISR pathway. In some embodiments, the disease, disorder, or condition is related to (e.g. caused by) a decrease in the level or activity of eIF2B, eIF2α, or a component of the eIF2 pathway or ISR pathway In some embodiments, the disease may be caused by a mutation to a gene or protein sequence related to a member of the eIF2 pathway (e.g., eIF2B, eIF2α, or other component). Exemplary mutations include an amino acid mutation in the eIF2B1, eIF2B2, eIF2B3, eIF2B4, eIF2B5 subunits. In some embodiments, an amino acid mutation (e.g., an amino acid substitution, addition, or deletion) in a particular protein that may result in a structural change, e.g., a conformational or steric change, that affects the function of the protein. For example, in some embodiments, amino acids in and around the active site or close to a binding site (e.g., a phosphorylation site, small molecule binding site, or protein-binding site) may be mutated such that the activity of the protein is impacted. In some instances, the amino acid mutation (e.g., an amino acid substitution, addition, or deletion) may be conservative and may not substantially impact the structure or function of a protein. For example, in certain cases, the substitution of a serine residue with a threonine residue may not significantly impact the function of a protein. In other cases, the amino acid mutation may be more dramatic, such as the substitution of a charged amino acid (e.g., aspartic acid or lysine) with a large, nonpolar amino acid (e.g., phenylalanine or tryptophan) and therefore may have a substantial impact on protein function. The nature of the mutations that affect the structure of function of a gene or protein may be readily identified using standard sequencing techniques, e.g., deep sequencing techniques that are well known in the art. In some embodiments, a mutation in a member of the eIF2 pathway may affect binding or activity of to a compound of Formula (I) or a pharmaceutically acceptable salt, solvate, hydrate, tautomer, or stereoisomer thereof and thereby modulate treatment of a particular disease, disorder, or condition, or a symptom thereof.

In some embodiments, an eIF2 protein may comprise an amino acid mutation (e.g., an amino acid substitution, addition, or deletion) at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid substitution at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid addition at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue. In some embodiments, an eIF2 protein may comprise an amino acid deletion at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue.

In some embodiments, the eIF2 protein may comprise an amino acid mutation (e.g., an amino acid substitution, addition, or deletion) at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid substitution at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid addition at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. In some embodiments, the eIF2 protein may comprise an amino acid deletion at an alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine residue in the eIF2B1, eIF2B2, eIF2B3, eIF2B4, eIF2B5 subunits. Exemplary mutations include V183F (eIF2B1 subunit), H341Q (eIF2B3), I346T (eIF2B3), R483W (eIF2B4), R113H (eIF2B5), and R195H (eIF2B5).

In some embodiments, an amino acid mutation (e.g., an amino acid substitution, addition, or deletion) in a member of the eIF2 pathway (e.g., an eIF2B protein subunit) may affect binding or activity of a compound of Formula (I) or a pharmaceutically acceptable salt, solvate, hydrate, tautomer, or stereoisomer thereof and thereby modulate treatment of a particular disease, disorder, or condition, or a symptom thereof.

Neurodegenerative Disease

In some embodiments, the compound of Formula (I) or a pharmaceutically acceptable salt, solvate, hydrate, tautomer, or stereoisomer thereof is used to treat a neurodegenerative disease. As used herein, the term "neurodegenerative disease" refers to a disease or condition in which the function of a subject's nervous system becomes impaired. Examples of a neurodegenerative disease that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Frontotemporal dementia, Gerstmann-Straussler-Scheinker syndrome, Huntington's disease, HIV-associated dementia, Kennedy's disease, Krabbe's disease, Kuru, Lewy body dementia, Machado-Joseph disease (Spinocerebellar ataxia type 3), Multiple system atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

In some embodiments, the neurodegenerative disease comprises vanishing white matter disease, childhood ataxia with CNS hypo-myelination, a leukodystrophy, a leukoencephalopathy, a hypomyelinating or demyelinating disease, an intellectual disability syndrome, Alzheimer's disease, amyotrophic lateral sclerosis, Creutzfeldt-Jakob disease, Frontotemporal dementia, Gerstmann-Straussler-Scheinker disease, Huntington's disease, dementia (e.g., HIV-associated dementia or Lewy body dementia), Kuru, multiple sclerosis, Parkinson's disease, or a prion disease.

In some embodiments, the neurodegenerative disease comprises vanishing white matter disease, childhood ataxia with CNS hypo-myelination, a leukodystrophy, a leukoencephalopathy, a hypomyelinating or demyelinating disease, or an intellectual disability syndrome.

In some embodiments, the neurodegenerative disease comprises a psychiatric disease such as agoraphobia, Alzheimer's disease, anorexia nervosa, amnesia, anxiety disorder, attention deficit disorder, bipolar disorder, body dysmorphic disorder, bulimia nervosa, claustrophobia, depression, delusions, Diogenes syndrome, dyspraxia, insomnia, Munchausen's syndrome, narcolepsy, narcissistic personality disorder, obsessive-compulsive disorder, psychosis, phobic disorder, schizophrenia, seasonal affective disorder, schizoid personality disorder, sleepwalking, social phobia, substance abuse, tardive dyskinesia, Tourette syndrome, or trichotillomania.

In some embodiments, the compound of Formula (I) or a pharmaceutically acceptable salt, solvate, hydrate, tautomer, or stereoisomer thereof is used to treat vanishing white matter disease. Exemplary methods of treating vanishing white matter disease include, but are not limited to, reducing or eliminating a symptom of vanishing white matter disease, reducing the loss of white matter, reducing the loss of myelin, increasing the amount of myelin, or increasing the amount of white matter in a subject.

In some embodiments, the compound of Formula (I) or a pharmaceutically acceptable salt, solvate, hydrate, tautomer, or stereoisomer thereof is used to treat childhood ataxia with CNS hypo-myelination. Exemplary methods of treating childhood ataxia with CNS hypo-myelination include, but are not limited to, reducing or eliminating a symptom of childhood ataxia with CNS hypo-myelination, increasing the level of myelin, or decreasing the loss of myelin in a subject.

In some embodiments, the compound of Formula (I) or a pharmaceutically acceptable salt, solvate, hydrate, tautomer, or stereoisomer thereof is used to treat an intellectual disability syndrome. Exemplary methods of treating an intellectual disability syndrome include, but are not limited to, reducing or eliminating a symptom of an intellectual disability syndrome.

In some embodiments, the compound of Formula (I) or a pharmaceutically acceptable salt, solvate, hydrate, tautomer, or stereoisomer thereof is used to treat neurodegeneration. Exemplary methods of treating neurodegeneration include, but are not limited to, improvement of mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival.

In some embodiments, the compound of Formula (I) or a pharmaceutically acceptable salt, solvate, hydrate, tautomer, or stereoisomer thereof is used to treat a leukoencephalopathy or demyelinating disease. Exemplary leukoencephalopathies include, but are not limited to, progressive multifocal leukoencephalopathy, toxic leukoencephalopathy, leukoencephalopathy with vanishing white matter, leukoencephalopathy with neuroaxonal spheroids, reversible posterior leukoencephalopathy syndrome, hypertensive leukoencephalopathy, megalencephalic leukoencephalopathy with subcortical cysts, Charcot-Marie-Tooth disorder, and Devic's disease. A leukoencephalopathy may comprise a demyelinating disease, which may be inherited or acquired. In some embodiments, an acquired demyelinating disease may be an inflammatory demyelinating disease (e.g., an infectious inflammatory demyelinating disease or a non-infectious inflammatory demyelinating disease), a toxic demyelinating disease, a metabolic demyelinating disease, a hypoxic demyelinating disease, a traumatic demyelinating disease, or an ischemic demyelinating disease (e.g., Binswanger's disease). Exemplary methods of treating a leukoencephalopathy or demyelinating disease include, but are not limited to, reducing or eliminating a symptom of a leukoencephalopathy or demyelinating disease, reducing the loss of myelin, increasing the amount of myelin, reducing the loss of white matter in a subject, or increasing the amount of white matter in a subject.

In some embodiments, the compound of Formula (I) or a pharmaceutically acceptable salt, solvate, hydrate, tautomer, or stereoisomer thereof is used to treat a traumatic injury or a toxin-induced injury to the nervous system (e.g., the brain). Exemplary traumatic brain injuries include, but are not limited to, a brain abscess, concussion, ischemia, brain bleeding, cranial fracture, diffuse axonal injury, locked-in syndrome, or injury relating to a traumatic force or blow to the nervous system or brain that causes damage to an organ or tissue. Exemplary toxin-induced brain injuries include, but are not limited to, toxic encephalopathy, meningitis (e.g. bacterial meningitis or viral meningitis), meningoencephalitis, encephalitis (e.g., Japanese encephalitis, eastern equine encephalitis, West Nile encephalitis), Guillan-Barre syndrome, Sydenham's chorea, rabies, leprosy, neurosyphilis, a prion disease, or exposure to a chemical (e.g., arsenic, lead, toluene, ethanol, manganese, fluoride, dichlorodiphenyl-trichloroethane (DDT), dichlorodiphenyldichloroethylene (DDE), tetrachloroethylene, a polybrominated diphenyl ether, a pesticide, a sodium channel inhibitor, a potassium channel inhibitor, a chloride channel inhibitor, a calcium channel inhibitor, or a blood brain barrier inhibitor).

In other embodiments, the compound of Formula (I) or a pharmaceutically acceptable salt, solvate, hydrate, tautomer, or stereoisomer thereof is used to improve memory in a subject. Induction of memory has been shown to be facilitated by decreased and impaired by increased eIF2α phosphorylation. Regulators of translation, such as compounds disclosed herein (e.g. a compound of Formula (I)), could serve as therapeutic agents that improve memory in human disorders associated with memory loss such as Alzheimer's disease and in other neurological disorders that activate the UPR or ISR in neurons and thus could have negative effects on memory consolidation such as Parkinson's disease, schizophrenia, amyotrophic lateral sclerosis and prion diseases. In addition, a mutation in eIF2γ that disrupts complex integrity linked intellectual disability (intellectual disability syndrome or ID) to impaired translation initiation in humans. Hence, two diseases with impaired eIF2 function, ID and VWMD, display distinct phenotypes but both affect mainly the brain and impair learning. In some embodiments, the disease or condition is unsatisfactory memory (e.g., working memory, long term memory, short term memory, or memory consolidation)

In still other embodiments, the compound of Formula (I) or a pharmaceutically acceptable salt, solvate, hydrate, tautomer, or stereoisomer thereof aspect is used in a method to improve memory in a subject (e.g., working memory, long term memory, short term memory, or memory consolidation). In some embodiments, the subject is human. In some embodiments, the subject is a non-human mammal. In some embodiments, the subject is a domesticated animal. In some embodiments, the subject is a dog. In some embodiments, the subject is a bird. In some embodiments, the subject is a horse. In embodiments, the patient is a bovine. In some embodiments, the subject is a primate.

Cancer

In some embodiments, the compound of Formula (I) or a pharmaceutically acceptable salt, solvate, hydrate, tautomer, or stereoisomer thereof is used to treat cancer. As used herein, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In some embodiments, the compound of Formula (I) or a pharmaceutically acceptable salt, solvate, hydrate, tautomer, or stereoisomer thereof is used to treat pancreatic cancer, breast cancer, multiple myeloma, cancers of secretory cells. For example certain methods herein treat cancer by decreasing or reducing or preventing the occurrence, growth, metastasis, or progression of cancer. In some embodiments, the methods described herein may be used to treat cancer by decreasing or eliminating a symptom of cancer. In some embodiments, the compound of Formula (I) or a pharmaceutically acceptable salt, solvate, hydrate, tautomer, or stereoisomer thereof may be used as a single agent in a composition or in combination with another agent in a composition to treat a cancer described herein (e.g., pancreatic cancer, breast cancer, multiple myeloma, cancers of secretory cells).

Inflammatory Disease

In some embodiments, the compound of Formula (I) or a pharmaceutically acceptable salt, solvate, hydrate, tautomer, or stereoisomer thereof is used to treat an inflammatory disease. As used herein, the term "inflammatory disease" refers to a disease or condition characterized by aberrant inflammation (e.g. an increased level of inflammation compared to a control such as a healthy person not suffering from a disease). Examples of inflammatory diseases include postoperative cognitive dysfunction, arthritis (e.g., rheumatoid arthritis, psoriatic arthritis, juvenile idiopathic arthritis), systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, Vitiligo, asthma (e.g., allergic asthma), acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. Proteins associated with inflammation and inflammatory diseases (e.g. aberrant expression being a symptom or cause or marker of the disease) include interleukin-6 (IL-6), interleukin-8 (IL-8), interleukin-18 (IL-18), TNF-α (tumor necrosis factor-alpha), and C-reactive protein (CRP).

In some embodiments, the inflammatory disease comprises postoperative cognitive dysfunction, arthritis (e.g., rheumatoid arthritis, psoriatic arthritis, or juvenile idiopathic arthritis), systemic lupus erythematosus (SLE), myasthenia gravis, diabetes (e.g., juvenile onset diabetes or diabetes mellitus type 1), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (e.g., allergic asthma), acne vulgaris, celiac disease, chronic prostatitis, pelvic inflammatory disease, reperfusion injury, sarcoidosis, transplant rejection, interstitial cystitis, atherosclerosis, or atopic dermatitis.

In some embodiments, the inflammatory disease comprises postoperative cognitive dysfunction, which refers to a decline in cognitive function (e.g. memory or executive function (e.g. working memory, reasoning, task flexibility, speed of processing, or problem solving)) following surgery.

In other embodiments, the method of treatment is a method of prevention. For example, a method of treating postsurgical cognitive dysfunction may include preventing postsurgical cognitive dysfunction or a symptom of postsurgical cognitive dysfunction or reducing the severity of a symptom of postsurgical cognitive dysfunction by administering a compound described herein prior to surgery.

In some embodiments, the compound of Formula (I) or a pharmaceutically acceptable salt, solvate, hydrate, tautomer, or stereoisomer thereof is used to treat an inflammatory disease (e.g., an inflammatory disease described herein) by decreasing or eliminating a symptom of the disease. In some embodiments, the compound of Formula (I) or a pharmaceutically acceptable salt, solvate, hydrate, tautomer, or stereoisomer thereof may be used as a single agent in a composition or in combination with another agent in a composition to treat an inflammatory disease (e.g., an inflammatory disease described herein).

Musculoskeletal Diseases

In some embodiments, the compound of Formula (I) or a pharmaceutically acceptable salt, solvate, hydrate, tautomer, or stereoisomer thereof is used to treat a musculoskeletal disease. As used herein, the term "musculoskeletal disease" refers to a disease or condition in which the function of a subject's musculoskeletal system (e.g., muscles, ligaments, tendons, cartilage, or bones) becomes impaired. Exemplary musculoskeletal diseases that may be treated with a compound of Formula (I) or a pharmaceutically acceptable salt, solvate, hydrate, tautomer, or stereoisomer thereof include muscular dystrophy (e.g., Duchenne muscular dystrophy, Becker muscular dystrophy, distal muscular dystrophy, congenital muscular dystrophy, Emery-Dreifuss muscular dystrophy, facioscapulohumeral muscular dystrophy, or myotonic muscular dystrophy), multiple sclerosis, amyotropic lateral sclerosis, primary lateral sclerosis, progressive muscular atrophy, progressive bulbar palsy, pseudobulbar palsy, spinal muscular atrophy, progressive spinobulbar muscular atrophy, spinal cord spasticity, spinal muscle atrophy, myasthenia gravis, neuralgia, fibromyalgia, Machado-Joseph disease, cramp fasciculation syndrome, Freidrich's ataxia, a muscle wasting disorder (e.g., muscle atrophy, sarcopenia, cachexia), an inclusion body myopathy, motor neuron disease, or paralysis.

In some embodiments, the compound of Formula (I) or a pharmaceutically acceptable salt, solvate, hydrate, tautomer, or stereoisomer thereof is used to treat a musculoskeletal disease (e.g., a musculoskeletal disease described herein) by decreasing or eliminating a symptom of the disease. In some embodiments, the method of treatment comprises treatment of muscle pain or muscle stiffness associated with a musculoskeletal disease. In some embodiments, the compound of Formula (I) or a pharmaceutically acceptable salt, solvate, hydrate, tautomer, or stereoisomer thereof may be used as a single agent in a composition or in combination with another agent in a composition to treat a musculoskeletal disease (e.g., a musculoskeletal disease described herein).

Metabolic Diseases

In some embodiments, the compound of Formula (I) or a pharmaceutically acceptable salt, solvate, hydrate, tautomer, or stereoisomer thereof is used to treat metabolic disease. As used herein, the term "metabolic disease" refers to a disease or condition affecting a metabolic process in a subject. Exemplary metabolic diseases that may be treated with a compound of Formula (I) or a pharmaceutically acceptable salt, solvate, hydrate, tautomer, or stereoisomer thereof include non-alcoholic steatohepatitis (NASH), non-alcoholic fatty liver disease (NAFLD), liver fibrosis, obesity, heart disease, atherosclerosis, arthritis, cystinosis, diabetes (e.g., Type I diabetes, Type II diabetes, or gestational diabetes), phenylketonuria, proliferative retinopathy, or Kearns-Sayre disease.

In some embodiments, the compound of Formula (I) or a pharmaceutically acceptable salt, solvate, hydrate, tautomer, or stereoisomer thereof is used to treat a metabolic disease (e.g., a metabolic disease described herein) by decreasing or eliminating a symptom of the disease. In some embodiments, the method of treatment comprises decreasing or eliminating a symptom comprising elevated blood pressure, elevated blood sugar level, weight gain, fatigue, blurred vision, abdominal pain, flatulence, constipation, diarrhea, jaundice, and the like. In some embodiments, the compound of Formula (I) or a pharmaceutically acceptable salt, solvate, hydrate, tautomer, or stereoisomer thereof may be used as a single agent in a composition or in combination with another agent in a composition to treat a metabolic disease (e.g., a musculoskeletal disease described herein).

Methods of Increasing Protein Production

In another aspect, the compound of Formula (I) or a pharmaceutically acceptable salt, solvate, hydrate, tautomer, or stereoisomer thereof may be useful in applications where increasing protein production output is desirable, such as in vitro cell free systems for protein production.

In some embodiments, the present invention features a method of increasing protein expression of a cell or in vitro expression system, the method including administering an effective amount of a compound to the cell or expression system, wherein the compound is a the compound of Formula (I) or a pharmaceutically acceptable salt, solvate, hydrate, tautomer, or stereoisomer thereof. In some embodiments, the method is a method of increasing protein expression by a cell and includes administering an effective amount of a compound described herein (e.g. the compound of Formula (I) or a pharmaceutically acceptable salt, solvate, hydrate, tautomer, or stereoisomer thereof) to the cell. In other embodiments, the method is a method of increasing protein expression by an in vitro protein expression system and includes administering an effective amount of a compound described herein (e.g. the compound of Formula (I) or a pharmaceutically acceptable salt, solvate, hydrate, tautomer, or stereoisomer thereof) to the in vitro (e.g. cell free) protein expression system.

In some embodiments, the present invention features a method of increasing protein expression in a disease, disorder, or condition characterized by aberrant or lowered levels of protein production (e.g., a leukodystrophy, a leukoencephalopathy, a hypomyelinating or demyelinating disease, muscle-wasting disease, or sarcopenia).

In some embodiments, the compounds set forth herein are provided as pharmaceutical compositions including a compound of Formula (I) or a pharmaceutically acceptable salt, solvate, hydrate, tautomer, or stereoisomer thereof and a pharmaceutically acceptable excipient. In embodiments of the method, a compound of Formula (I) or a pharmaceutically acceptable salt, solvate, hydrate, tautomer, or stereoisomer thereof, is co-administered with a second agent (e.g. therapeutic agent). In other embodiments of the method, a compound of Formula (I) or a pharmaceutically acceptable salt, solvate, hydrate, tautomer, or stereoisomer thereof, is co-administered with a second agent (e.g. therapeutic agent), which is administered in a therapeutically effective amount. In embodiments, the second agent is an agent for improving memory.

Combination Therapy

In one aspect, the present invention features a pharmaceutical composition comprising a compound of Formula (I) or a pharmaceutically acceptable salt, solvate, hydrate, tautomer, or stereoisomer thereof as well as a second agent (e.g. a second therapeutic agent). In some embodiments, the pharmaceutical composition includes a second agent (e.g. a second therapeutic agent) in a therapeutically effective amount. In some embodiments, the second agent is an agent for treating cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway.

The compounds described herein can be used in combination with one another, with other active agents known to be useful in treating cancer, a neurodegenerative disease, an inflammatory disease, a musculoskeletal disease, a metabolic disease, or a disease or disorder associated with impaired function of eIF2B, eIF2α, or a component of the eIF2 pathway or ISR pathway or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for a cancer, a neurodegenerative disease, a leukodystrophy, an inflammatory disease, a musculoskeletal disease, a metabolic disease, or a disease or disorder associated with impaired function of eIF2B, eIF2α, or a component of the eIF2 pathway or ISR pathway.

In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating a leukodystrophy. In embodiments, the second agent is an agent for treating vanishing white matter disease. In embodiments, the second agent is an agent for treating childhood ataxia with CNS hypo-myelination. In embodiments, the second agent is an agent for treating an intellectual disability syndrome. In embodiments, the second agent is an agent for treating pancreatic cancer. In embodiments, the second agent is an agent for treating breast cancer. In embodiments, the second agent is an agent for treating multiple myeloma. In embodiments, the second agent is an agent for treating myeloma. In embodiments, the second agent is an agent for treating a cancer of a secretory cell. In embodiments, the second agent is an agent for reducing eIF2α phosphorylation. In embodiments, the second agent is an agent for inhibiting a pathway activated by eIF2α phosphorylation. In embodiments, the second agent is an agent for inhibiting a pathway activated by eIF2α. In embodiments, the second agent is an agent for inhibiting the integrated stress response. In embodiments, the second agent is an anti-inflammatory agent. In embodiments, the second agent is an agent for treating postsurgical cognitive dysfunction. In embodiments, the second agent is an agent for treating traumatic brain injury. In embodiments, the second agent is an agent for treating a musculoskeletal disease. In embodiments, the second agent is an agent for treating a metabolic disease. In embodiments, the second agent is an anti-diabetic agent.

Anti-Cancer Agents

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anticancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl;

safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol, i.e. paclitaxel), Taxotere, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and SC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-1 12378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HC1), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A 1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tularik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-25041 1 (Sanofi), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{m}$Ag, $^{m}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Additional Agents

In some embodiments, the second agent for use in combination with a compound (e.g., a compound of Formula (I)) or composition thereof described herein is an agent for use in treating a neurodegenerative disease, a leukodystrophy, an inflammatory disease, a musculoskeletal disease, or a metabolic disease. In some embodiments, a second agent for use in combination with a compound (e.g., a compound of Formula (I)) or composition thereof described herein is an agent approved by the FDA or similar regulatory agency of a country other than the USA, for treating a disease, disorder, or condition described herein.

In some embodiments, a second agent for use in treating a neurodegenerative disease, a leukodystrophy, an inflammatory disease, a musculoskeletal disease, or a metabolic disease includes, but is not limited to, an anti-psychotic drug, anti-depressive drug, anti-anxiety drug, analgesic, a stimulant, a sedative, a pain reliever, an anti-inflammatory agent, a benzodiazepine, a cholinesterase inhibitor, a non-steroidal anti-inflammatory drug (NSAID), a corticosteroid, a MAO inhibitor, a beta-blocker, a calcium channel blocker, an antacid, or other agent. Exemplary second agents may include donepezil, galantamine, rivastigmine, memantine, levodopa, dopamine, pramipexole, ropinirole, rotigotine, doxapram, oxazepam, quetiapine, selegiline, rasagiline, entacapone, benztropine, trihexyphenidyl, riluzole, diazepam, chlorodiazepoxide, lorazepam, alprazolam, buspirone, gepirone, ispapirone, hydroxyzine, propranolol, hydroxyzine, midazolam, trifluoperazine, methylphenidate, atomoxetine, methylphenidate, pemoline, perphenazine, divalproex, valproic acid, sertraline, fluoxetine, citalopram, escitalopram, paroxetine, fluvoxamine, trazodone, desvenlafaxine, duloxetine, venlafaxine, amitriptyline, amoxapine, clomipramine, desipramine, imipramine, nortriptyline, protriptyline, trimipramine, maprotiline, bupropion, nefazodone, vortioxetine, lithium, clozapine, fluphenazine, haloperidol, paliperidone, loxapine, thiothixene, pimozide, thioridazine, risperidone, aspirin, ibuprofen, naproxen, acetaminophen, azathioprine, methotrexate, mycophenolic acid, leflunomide, dibenzoylmethane, cilostazol, pentoxifylline, duloxetine, a cannabinoid (e.g, nabilone), simethicone, magaldrate, aluminum salts, calcium salts, sodium salts, magnesium salts, alginic acid, acarbose, albiglutide, alogliptin, metformin, insulin, lisinopril, atenolol, atorvastatin, fluvastatin, lovastatin, pitavastatin, simvastatin, rosuvastatin, and the like.

Naturally derived agents or supplements may also be used in conjunction with a compound of Formula (I) or a composition thereof to treat a neurodegenerative disease, an inflammatory disease, a musculoskeletal disease, or a metabolic disease. Exemplary naturally derived agents or supplements include omega-3 fatty acids, carnitine, citicoline, curcumin, gingko, vitamin E, vitamin B (e.g., vitamin B5, vitamin B6, or vitamin B12), huperzine A, phosphatidylserine, rosemary, caffeine, melatonin, chamomile, St. John's wort, tryptophan, and the like.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthetic Protocols

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures. General scheme relating to methods of making exemplary compounds of the invention are additionally described in the section entitled Methods of Making Compounds.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Abbreviations

APCI for atmospheric pressure chemical ionization; DMSO for dimethyl sulfoxide; HPLC for high performance liquid chromatography; MS for mass spectrum; and NMR for nuclear magnetic resonance.

Example 1: 2-(4-chlorophenoxy)-N-(3-{5-[(4-chlorophenoxy)methyl]-1,3,4-oxadiazol-2-yl}bicyclo[1.1.1]pentan-1-yl)acetamide (Compound 100)

Example 1A: Methyl 3-(2-(4-chlorophenoxy)acetamido)bicyclo[1.1.1]pentane-1-carboxylate To a solution of 2-(4-chlorophenoxy)acetic acid (10.88 g, 58.5 mmol) in N,N-dimethylformamide (150 mL) were added methyl 3-aminobicyclo[1.1.1]pentane-1-carboxylate (Pharmablock, 10.5 g, 53.2 mmol), N,N-diisopropylethylamine (27.5 g, 213 mmol) and 2-(3H-[1,2,3]triazolo[4,5-b]pyridin-3-yl)-1,1,3,3-tetramethylisouronium hexafluorophosphate(V) (30.3 g, 80 mmol). The reaction mixture was stirred at ambient temperature for 3 hours, and then partitioned between ethyl acetate (250 mL) and water (250 mL). The aqueous layer was extracted with ethyl acetate (3×200 mL). The combined organic layer was washed with brine (5×300 mL), dried ($Na_2SO_4$), filtered and concentrated under reduced pressure. The crude product was purified by flash chromatography (silica gel, 10-20% ethyl acetate/heptane) to provide 15.4 g (94%) of the title compound as light yellow solid. MS (APCI) m/z 310 (M+H)+.

Example 1B: 3-(2-(4-chlorophenoxy)acetamido)bicyclo[1.1.1]pentane-1-carboxylic acid A solution of Example 1A (0.52 g, 0.169 mmol) in tetrahydrofuran (3 mL) was treated with 1 N LiOH solution (3.34 mL) and stirred at ambient temperature for 0.5 hour. The reaction mixture was concentrated and neutralized with 6 N HCl. The resultant precipitate was collected by filtration, washed with water, and dried in a vacuum oven to provide the title compound. MS (APCI) m/z 296 (M+H)+.

Example 1C: 2-(4-chlorophenoxy)-N-(3-{5-[(4-chlorophenoxy)methyl]-1,3,4-oxadiazol-2-yl}bicyclo[1.1.1]pentan-1-yl)acetamide A solution of Example 1B (0.050 g, 0.169 mmol) and 2-(4-chlorophenoxy)acetohydrazide (0.034 g, 0169 mmol) in phosphorus oxychloride (Aldrich, 0.5 mL) was heated at 90° C. for 6 hours. The mixture was cooled to about 25° C. and concentrated. The residue was poured onto ice, which was then diluted with saturated aqueous $NaHCO_3$ and extracted with dichloromethane. The organic extract was dried ($Na_2SO_4$), filtered, and concentrated. The residue was purified by HPLC (Phenomenex® Luna® C18(2) 5 μm 100 Å AXIA™ column 250 mm×21.2 mm, flow rate 25 mL/minute, 10-80% gradient of acetonitrile in buffer (0.1% trifluoroacetic acid in water)). $^1$H NMR (500 MHz, DMSO-$d_6$) δ ppm 8.91 (s, 1H), 7.44-7.29 (m, 4H), 7.16-7.05 (m, 2H), 7.05-6.93 (m, 2H), 5.38 (s, 2H), 4.46 (s, 2H), 2.20 (s, 6H). MS (APCI) m/z 461 (M+H)$^+$.

Example 2: 2-(4-chlorophenoxy)-N-(3-{3-[(4-chlorophenoxy)methyl]-1,2,4-oxadiazol-5-yl}bicyclo[1.1.1]pentan-1-yl)acetamide (Compound 101)

Example 2A: 2-(4-chlorophenoxy)-N-hydroxyacetimidamide

To a stirred solution of hydroxylamine hydrochloride (12.44 g, 179 mmol) in ethanol (600 mL) was added N,N-diisopropylethylamine (31.3 mL, 179 mmol) at ambient temperature. After 10 minutes 2-(4-chlorophenoxy)acetonitrile (30 g, 179 mmol) was added to the mixture. The reaction mixture was stirred at 80° C. for 12 hours. The mixture was concentrated under reduced pressure to provide 30 g (84%) of the title compound as a white solid. MS (APCI) m/z 201 (M+H)$^+$.

Example 2B: 2-(4-chlorophenoxy)-N-(3-[3-[(4-chlorophenoxy)methyl]-1,2,4-oxadiazol-5-yl]bicyclo[1.1.1]pentan-1-yl)acetamide A solution of Example 1B (0.050 g, 0.169 mmol) and carbonyldiimidazole (0.030 g, 0.186 mmol) in N,N-dimethylformamide (1 mL) was stirred at ambient temperature for 3 hours. A solution of Example 2A (0.034 g, 0.169 mmol) in N,N-dimethylformamide (0.5 mL) was added, and the reaction was heated at 90° C. for 16 hours. The reaction mixture was concentrated and purified by HPLC (Phenomenex® Luna® C18(2) 5 μm 100 Å AXIA™ column 250 mm×21.2 mm, flow rate 25 mL/minute, 10-80% gradient of acetonitrile in buffer (0.1% trifluoroacetic acid in water)). $^1$H NMR (501 MHz, DMSO-$d_6$) δ ppm 8.90 (s, 1H), 7.34 (dd, J=9.0, 5.5 Hz, 4H), 7.05 (d, J=9.0 Hz, 2H), 6.97 (d, J=9.0 Hz, 2H), 5.25 (s, 2H), 4.45 (s, 2H), 2.51 (s, 6H). MS (APCI) m/z 461 (M+H)$^+$.

Example 3 N-(3-{3-[(4-chlorophenoxy)methyl]-1,2,4-oxadiazol-5-yl}bicyclo[1.1.1]pentan-1-yl)-2-(3-methylphenoxy)acetamide (Compound 102)

Example 3A: tert-butyl (3-(((2-(4-chlorophenoxy)acetimidamido)oxy)-carbonyl)bicyclo[1.1.1]pentan-1-yl)carbamate To a solution of Example 2A (6 g, 25.9 mmol) in N,N-dimethylformamide (120 mL) were added N-ethyl-N- isopropylpropan-2-amine (13.56 mL, 78 mmol), 2-(3H-[1,2,3]triazolo[4,5-b]pyridin-3-yl)-1,1,3,3-tetramethylisouronium tetrafluoroborate (10.00 g, 31.0 mmol) and 1H-benzo[d][1,2,3]triazol-1-ol hydrate (0.792 g, 5.17 mmol) at ambient temperature. Then 3-((tert-butoxycarbonyl)amino)bicyclo[1.1.1]pentane-1-carboxylic acid (Pharmablock, 12.98 g, 25.9 mmol) was added to this mixture at 0° C. The mixture was stirred at ambient for 2 hours, then diluted with water (1000 mL), and the resulting mixture was extracted with ethyl acetate (3×350 mL). The combined organic layers were washed with brine (3×200 mL), dried ($Na_2SO_4$) and concentrated under reduced pressure to provide 13 g (98%) of the title compound as a white solid. MS (APCI) m/z 410 $(M+H)^+$.

Example 3B: tert-butyl (3-(3-((4-chlorophenoxy)methyl)-1,2,4-oxadiazol-5-yl)bicyclo[1.1.1]pentan-1-yl)carbamate A solution of Example 3A (13 g, 25.4 mmol) in N,N-dimethylformamide (200 mL) was stirred for 2 hours at 120° C. Then the mixture was diluted with water (1000 mL), and the resulting mixture was extracted with ethyl acetate (3×300 mL). The combined organic layer was washed with HCl (350 mL, 1 N) and brine (3×250 mL), dried ($Na_2SO_4$) and concentrated under reduced pressure to provide 15 g (94%) of the title compound as a brown solid. MS (APCI) m/z 392 $(M+H)^+$.

Example 3C: 3-(3-((4-chlorophenoxy)methyl)-1,2,4-oxadiazol-5-yl)bicyclo[1.1.1]pentan-1-amine To a solution of Example 3B (14 g, 26.8 mmol) in dichloromethane (200 mL) was added trifluoroacetic acid (40 mL, 519 mmol) dropwise at 0° C. Then the mixture was stirred at 25° C. for 2 hours. Then the mixture was concentrated under reduced pressure. The residue was diluted with water (500 mL), and the mixture was washed with dichloromethane (2×300 mL). Then the aqueous phase was adjusted with saturated $NaHCO_3$ to pH=8 and extracted with ethyl acetate (4×300 mL). The combined organic layer was washed with brine (300 mL), dried ($Na_2SO_4$) and concentrated under reduced pressure to provide 7.9 g (95%) of the title compound as an off white solid. MS (APCI) m/z 292 (M+H Example 3D: N-(3-[3-[(4-chlorophenoxy)methyl]-1,2,4-oxadiazol-5-yl]bicyclo[0.1.1.]pentan-1-yl)-2-(3-methylphenoxy)acetamide To a solution of 2-(m-tolyloxy)acetic acid (16.7 mg, 0.101 mmol) in N,N-dimethylacetamide (0.5 mL) was added N,N-diisopropylethylamine (0.064 mL, 0.366 mmol), 1-[bis(dimethylamino)methylene]-1H-1,2,3-triazolo[4,5-b]pyridinium 3-oxid hexafluorophosphate (104 mg, 0.274 mmol) and Example 3C (30.1 mg, 0.091 mmol). The reaction was stirred at room temperature for 18 hours. The crude reaction was purified by HPLC (2-coupled C8 5 µm 100 Å columns 30 mm×75 mm each, flow rate of 50 mL/minute, 5-90% gradient of acetonitrile in buffer (0.1% trifluoroacetic acid in water)). $^1$H NMR (400 MHz, DMSO-d$_6$) δ ppm 8.94 (s, 1H), 7.39-7.30 (m, 2H), 7.17 (t, J=8.0 Hz, 1H), 7.10-7.01 (m, 2H), 6.83-6.70 (m, 3H), 5.23 (s, 2H), 4.41 (s, 2H), 2.53 (s, 6H), 2.27 (s, 3H). MS (APCI) m/z 440.300 $(M+H)^+$.

Example 4 N-(3-{3-[(4-chlorophenoxy)methyl]-1,2,4-oxadiazol-5-yl}bicyclo[1.1.1]pentan-1-yl)-2-(4-methylphenoxy)acetamide (Compound 103)

The title compound was prepared using the method described in Example 3D by replacing 2-(m-tolyloxy)acetic acid with 2-(p-tolyloxy)acetic acid (16.7 mg, 0.101 mmol). $^1$H NMR (400 MHz, DMSO-d6) δ ppm 7.39-7.30 (m, 2H), 7.14-7.01 (m, 4H), 6.90-6.80 (m, 2H), 5.23 (s, 2H), 4.39 (s, 2H), 2.53 (s, 6H), 2.22 (s, 3H). MS (APCI) m/z 440.310 $(M+H)^+$.

Example 5 2-(4-chloro-3-methylphenoxy)-N-(3-{3-[(4-chlorophenoxy)methyl]-1,2,4-oxadiazol-5-yl}bicyclo[1.1.1]pentan-1-yl)acetamide (Compound 104)

The title compound was prepared using the method described in Example 3D by replacing 2-(m-tolyloxy)acetic acid with 2-(4-chloro-3-methylphenoxy)acetic acid (20.2 mg, 0.101 mmol). $^1$H NMR (400 MHz, DMSO-d$_6$) δ ppm 7.40-7.25 (m, 3H), 7.10-7.02 (m, 2H), 6.97 (d, J=3.0 Hz, 1H), 6.82 (dd, J=8.8, 3.1 Hz, 1H), 5.23 (s, 2H), 4.43 (s, 2H), 2.53 (s, 6H), 2.28 (s, 3H). MS (APCI) m/z 474.270 $(M+H)^+$.

Example 6 N-(3-{3-[(4-chlorophenoxy)methyl]-1,2,4-oxadiazol-5-yl}bicyclo[1.1.1]pentan-1-yl)-2-(3,4-dichlorophenoxy)acetamide (Compound 105)

The title compound was prepared using the method described in Example 3D by replacing 2-(m-tolyloxy)acetic acid with 2-(3,4-dichlorophenoxy)acetic acid (22.2 mg, 0.101 mmol). $^1$H NMR (400 MHz, DMSO-d$_6$) δ ppm 7.53 (d, J=8.9 Hz, 1H), 7.40-7.31 (m, 2H), 7.26 (d, J=2.9 Hz, 1H), 7.09-7.03 (m, 2H), 6.99 (dd, J=8.9, 3.0 Hz, 1H), 5.23 (s, 2H), 4.50 (s, 2H), 2.53 (s, 6H). MS (APCI) m/z 496.210 $(M+H)^+$.

Example 7 2-(3-chlorophenoxy)-N-(3-{3-[(4-chlorophenoxy)methyl]-1,2,4-oxadiazol-5-yl}bicyclo[1.1.1]pentan-1-yl)acetamide (Compound 106)

The title compound was prepared using the method described in Example 3D by replacing 2-(m-tolyloxy)acetic acid with 2-(3-chlorophenoxy)acetic acid (18.8 mg, 0.101 mmol). $^1$H NMR (400 MHz, DMSO-d$_6$) δ ppm 7.39-7.28 (m, 3H), 7.09-7.00 (m, 4H), 6.94 (ddd, J=8.4, 2.4, 0.9 Hz, 1H), 5.23 (s, 2H), 4.48 (s, 2H), 3.16 (s, 2H), 2.53 (s, 6H). MS (APCI) m/z 460.260 $(M+H)^+$.

Example 8 N-(3-{3-[(4-chlorophenoxy)methyl]-1,2,4-oxadiazol-5-yl}bicyclo[1.1.1]pentan-1-yl)-2-(3-fluorophenoxy)acetamide (Compound 107)

The title compound was prepared using the method described in Example 3D by replacing 2-(m-tolyloxy)acetic acid with 2-(3-fluorophenoxy)acetic acid (17.1 mg, 0.101 mmol). $^1$H NMR (400 MHz, DMSO-d$_6$) δ ppm 8.99 (s, 1H), 7.41-7.25 (m, 3H), 7.12-6.97 (m, 2H), 6.89-6.72 (m, 3H), 5.23 (s, 2H), 4.47 (s, 2H), 2.53 (s, 6H). MS (APCI) m/z 444.280 $(M+H)^+$.

Example 9 N-(3-{3-[(4-chlorophenoxy)methyl]-1,2,4-oxadiazol-5-yl}bicyclo[1.1.1]pentan-1-yl)-2-(4-fluorophenoxy)acetamide (Compound 108)

The title compound was prepared using the method described in Example 3D by replacing 2-(m-tolyloxy)acetic acid with 2-(4-fluorophenoxy)acetic acid (17.1 mg, 0.101 mmol). $^1$H NMR (400 MHz, DMSO-d$_6$) δ ppm 8.96 (s, 1H), 7.39-7.31 (m, 2H), 7.19-7.03 (m, 4H), 7.02-6.93 (m, 2H), 5.23 (s, 2H), 4.42 (s, 2H), 2.53 (s, 6H). MS (APCI) m/z 444.280 (M+H)$^+$.

Example 10 N-(3-{5-[(4-chlorophenoxy)methyl]-1, 3,4-oxadiazol-2-yl}bicyclo[1.1.1]pentan-1-yl)-2-(3, 4-dichlorophenoxy)acetamide (Compound 109)

Example 10A tert-butyl (3-(2-(2-(4-chlorophenoxy) acetyl)hydrazine-1-carbonyl)bicyclo[1.1.1]pentan-1-yl)carbamate To a solution of 3-((tert-butoxycarbonyl)amino)bicyclo [1.1.1]pentane-1-carboxylic acid (Pharmablock, 0.844 g, 3.71 mmol) in N,N-dimethylformamide (10 mL) was added N,N-diisopropylethylamine (1.3 mL, 7.43 mmol), 1-[bis (dimethylamino)methylene]-1H-1,2,3-triazolo[4,5-b]pyridinium 3-oxid hexafluorophosphate (1.55 g, 4.09 mmol) and 2-(4-chlorophenoxy)acetohydrazide (0.82 g, 4.09 mmol). The reaction was stirred at room temperature for 18 hours and poured into water (200 mL). The precipitate was collected by filtration, washed with water and dried in a vacuum oven to provide 1.491 g (98%) of the title compound. MS (APCI) m/z 410 (M+H)$^+$.

Example 10B: tert-butyl (3-(5-((4-chlorophenoxy) methyl)-1,3,4-oxadiazol-2-yl)bicyclo[1.1.1]pentan-1-yl)carbamate A solution of Example 73A (0.45 g, 1.1 mmol) in ethyl acetate (3 mL) was treated with 2,4,6-tripropyl-1,3,5,2,4,6-trioxatriphosphinane 2,4,6-trioxide (Sigma-Aldrich, 2.10 g, 3.29 mmol) and trimethylamine (0.6 mL, 3.9 mmol) and heated at 85° C. for 24 hours. The reaction was quenched with water, and the mixture was extracted with ethyl acetate twice. Combined organic extracts were dried (Na$_2$SO$_4$), filtered and concentrated. The residue was purified on silica gel eluted with 0-15% of methanol in dichloromethane to provide 0.13 g (30%) of the title compound. MS (APCI) m/z 392 (M+H)$^+$.

Example 10C: 3-(5-((4-chlorophenoxy)methyl)-1,3, 4-oxadiazol-2-yl)bicyclo[1.1.1]pentan-1-amine To a solution of Example 10B (0.13 g, 0.33 mmol) in dioxane (1 mL) was added 4 N HCl in dioxane (0.8 mL, 3.3 mmol). The mixture was stirred at 25° C. for 2 hours and concentrated under reduced pressure to provide the title compound as a hydrochloride salt (0.096 g, 99%). MS (APCI) m/z 292 (M+H)$^+$.

Example 10D: N-(3-{5-[(4-chlorophenoxy)methyl]-1,3,4-oxadiazol-2-yl}bicyclo[1.1.1]pentan-1-yl)-2-(3,4-dichlorophenoxy)acetamide To a solution of 2-(3,4-dichlorophenoxy)acetic acid (0.036 g, 0.161 mmol) in N,N-dimethylformamide (1 mL) was added N,N-diisopropylethylamine (0.064 mL, 0.366 mmol), 1-[bis(dimethylamino)methylene]-1H-1,2,3-triazolo [4,5-b]pyridinium 3-oxid hexafluorophosphate (0.061 g, 0.161 mmol) and Example 10C (0.048 g, 0.146 mmol). The reaction was stirred at room temperature for 18 hours and concentrated. HPLC purification (Phenomenex® Luna® C18(2) 5 μm 100 Å AXIA™ column 250 mm×21.2 mm, flow rate 25 mL/minute, 10-80% gradient of acetonitrile in buffer (0.1% trifluoroacetic acid in water)) afforded the title compound. $^1$H NMR (400 MHz, DMSO-d$_6$) δ ppm 8.92 (s, 1H), 7.54 (s, 1H), 7.38 (d, J=8.9 Hz, 2H), 7.28 (d, J=2.8 Hz, 1H), 7.10 (d, J=9.0 Hz, 2H), 7.01 (s, 1H), 5.38 (s, 2H), 4.52 (s, 2H), 2.48 (s, 6H). MS (APCI) m/z 496 (M+H)$^+$.

Example 11 2-(4-chloro-3-fluorophenoxy)-N-(3-{3-[(4-chlorophenoxy)methyl]-1,2,4-oxadiazol-5-yl}bicyclo[1.1.1]pentan-1-yl)acetamide (Compound 110)

The title compound was prepared using the method described in Example 3D by replacing 2-(m-tolyloxy)acetic acid with 2-(4-chloro-3-fluorophenoxy)acetic acid (17.1 mg, 0.101 mmol). $^1$H NMR (501 MHz, DMSO-d$_6$) δ ppm 8.94 (s, 1H), 7.50 (t, J=8.9 Hz, 1H), 7.44-7.31 (m, 2H), 7.19-7.01 (m, 3H), 6.87 (ddd, J=9.0, 2.9, 1.2 Hz, 1H), 5.26 (s, 2H), 4.51 (s, 2H), 2.54 (s, 6H). MS (APCI) m/z 479 (M+H)$^+$.

Example 12 2-(4-chloro-2-fluorophenoxy)-N-(3-{3-[(4-chlorophenoxy)methyl]-1,2,4-oxadiazol-5-yl}bicyclo[1.1.1]pentan-1-yl)acetamide (Compound 111)

The title compound was prepared using the method described in Example 3D by replacing 2-(m-tolyloxy)acetic acid with 2-(4-chloro-2-fluorophenoxy)acetic acid (17.1 mg, 0.101 mmol). $^1$H NMR (400 MHz, DMSO-d$_6$) δ ppm 8.93 (s, 1H), 7.46 (dd, J=11.2, 2.5 Hz, 1H), 7.40-7.33 (m, 2H), 7.24-7.18 (m, 1H), 7.11 (d, J=9.0 Hz, 1H), 7.09-7.04 (m, 2H), 5.26 (s, 2H), 4.58 (s, 2H), 2.52 (s, 6H). MS (APCI) m/z 479 (M+H)$^+$.

Example 13 N-(3-{3-[(4-chlorophenoxy)methyl]-1, 2,4-oxadiazol-5-yl}bicyclo[1.1.1]pentan-1-yl)-2-[(5-methyl-1,2-oxazol-3-yl)methoxy]acetamide (Compound 112)

The title compound was prepared using the method described in Example 3D by replacing 2-(m-tolyloxy)acetic acid with 2-((5-methylisoxazol-3-yl)methoxy)acetic acid (11.78 mg, 0.07 mmol). $^1$H NMR (501 MHz, DMSO-d$_6$) δ ppm 7.41-7.33 (m, 2H), 7.10-7.05 (m, 2H), 6.32 (d, J=1.0 Hz, 1H), 5.25 (s, 2H), 4.57 (s, 2H), 3.91 (s, 2H), 2.52 (s, 6H), 2.41 (d, J=0.9 Hz, 3H). MS (APCI+) m/z 445.3 (M+H)$^+$.

Example 14 2-(4-chloro-3-fluorophenoxy)-N-(3-{5-[(4-chlorophenoxy)methyl]-1,2,4-oxadiazol-3-yl}bicyclo[1.1.1]pentan-1-yl)acetamide (Compound 113)

Example 14A: methyl 3-(N-hydroxycarbamimidoyl) bicyclo[1.1.1]pentane-1-carboxylate A solution of methyl 3-cyanobicyclo[1.1.1]pentane-1-carboxylate (0.5 g, 3.31 mmol) in ethanol (10 mL) was treated with 50% aqueous hydroxylamine (0.66 mL, 9.92 mmol) heated at 70° C. for 1 hour. The reaction mixture was concentrated to provide the title compound (0.6 g, 98%).

Example 14B: methyl 3-(5-((4-chlorophenoxy) methyl)-1,2,4-oxadiazol-3-yl)bicyclo[1.1.1]pentane-1-carboxylate 2-(4-Chlorophenoxy)acetic acid (0.61 g, 3.26 mmol) and carbonyldiimidazole (0.58 g, 3.58 mmol) in N,N-dimethylformamide (6 mL) were stirred at 25° C. for 1 hour, then a solution of Example 14A in N,N-dimethylformamide (4 mL) was added, and the reaction mixture was heated at 90° C. for 3 hours. The reaction mixture was cooled, poured into ice and extracted with ethyl acetate twice. The combined organic layer was washed with brine (300 mL), dried ($Na_2SO_4$) and concentrated under reduced pressure to provide the title compound (0.7 g, 64.2%) as an off white solid.

Example 14C: 3-(5-((4-chlorophenoxy)methyl)-1,2,4-oxadiazol-3-yl)bicyclo[1.1.1]pentane-1-carboxylic acid A solution of Example 14B (0.70 g, 2.09 mmol) in tetrahydrofuran (10 mL) was treated with 1 N LiOH solution (10.46 mL) stirred at 25° C. for 0.5 hour. The reaction mixture was concentrated and neutralized with 6 N HCl. The precipitate was collected by filtration, washed with water, and dried in a vacuum oven to provide the title compound.

Example 14D: tert-butyl (3-(5-((4-chlorophenoxy)methyl)-1,2,4-oxadiazol-3-yl)bicyclo[1.1.1]pentan-1-yl)carbamate A solution of Example 14C (0.2 g, 0.624 mmol) in tert-butanol (3 mL) was treated with diphenyl phosphorazidate (0.189 g, 0.686 mmol) and trimethylamine (0.113 mL, 0.811 mmol) and heated at 60° C. for 18 hours. The reaction mixture was filtered, and the filtrate concentrated. The residue was purified by flash chromatography (silica gel, 0-10% methanol/dichloromethane) to provide 0.027 g (11%) of the title compound.

Example 14E: 3-(5-((4-chlorophenoxy)methyl)-1,2,4-oxadiazol-3-yl)bicyclo[1.1.1]pentan-1-amine A solution of Example 14D (0.027 g, 0.069 mmol) in dioxane (0.2 mL) was treated with 4 N HCl in dioxane (0.2 mL) and stirred at ambient temperature for 4 hours. The reaction mixture was concentrated to provide 0.022 g (97%) the title compound Example 14F: 2-(4-chloro-3-fluorophenoxy)-N-(3-{5-[(4-chlorophenoxy)methyl]-1,2,4-oxadiazol-3-yl}bicyclo[1.1.1]pentan-1-yl)acetamide To solution of Example 14E (0.022 g, 0.069 mmol) and 2-(4-chloro-3-fluorophenoxy)acetic acid (0.015 g, 0.076 mmol) in N,N-dimethylformamide (0.5 mL) was added N,N-diisopropylethylamine (0.03 mL, 0.173 mmol) and 2-(7-aza-1H-benzotriazole-1-yl)-1,1,3,3-tetramethyluronium hexafluorophosphate (0.029 g, 0.076 mmol) under nitrogen. The resulting mixture was stirred at ambient temperature for 18 hours and concentrated. The residue was purified on HPLC (Phenomenex® Luna® C18(2) 5 m 100 Å AXIA™ column 250 mm×21.2 mm, flow rate 25 mL/minute, 10-80% gradient of acetonitrile in buffer (0.1% trifluoroacetic acid in water)) to provide 0.028 g (85%) of the title compound as a white solid. $^1$H NMR (400 MHz, DMSO-$d_6$) δ ppm 8.89 (s, 1H), 7.50 (t, J=8.9 Hz, 1H), 7.43-7.35 (m, 2H), 7.08 (dd, J=8.9, 2.5 Hz, 2H), 6.92-6.82 (m, 2H), 5.49 (s, 2H), 4.50 (s, 2H), 2.42 (s, 6H). MS (APCI) m/z 479 (M+H)$^+$.

Example 15 N-(3-{3-[(4-chlorophenoxy)methyl]-1,2,4-oxadiazol-5-yl}bicyclo[1.1.1]pentan-1-yl)-2-{[6-(trifluoromethyl)pyridin-3-yl]oxy}acetamide (Compound 114)

Example 15A: tert-butyl 2-((6-(trifluoromethyl)pyridin-3-yl)oxy)acetate A solution of 6-(trifluoromethyl)pyridine-3-ol (0.8 g, 4.91 mmol) in N,N-dimethylformamide (10 mL) was treated with tert-butyl 2-bromoacetate (0.797 mL, 5.40 mmol) and potassium carbonate (1.356 g, 9.81 mmol) and heated at 65° C. for 2 hours. The reaction mixture was diluted with ethyl acetate and washed with water twice. The organic fraction was dried ($Na_2SO_4$), filtered and concentrated to provide 1.32 g (97%) of the title compound. MS (APCI) m/z 278 (M+H)$^+$.

Example 15B: 2-((6-(trifluoromethyl)pyridin-3-yl)oxy)acetic acid

A solution of Example 15A (1.32 g, 4.76 mmol) in dioxane (6 mL) was treated with 4 N HCl in dioxane (6 mL) and stirred at 25° C. for 4 hours. The reaction mixture was concentrated to provide the title compound (1.05 g, 100%). MS (APCI) m/z 222 (M+H)$^+$.

Example 15C: N-(3-{3-[(4-chlorophenoxy)methyl]-1,2,4-oxadiazol-5-yl}bicyclo[1.1.1]pentan-1-yl)-2-{[6-(trifluoromethyl)pyridin-3-yl]oxy}acetamide The title compound was prepared using the method described in Example 3D by replacing 2-(m-tolyloxy)acetic acid with Example 15B (20 mg, 0.091 mmol). $^1$H NMR (400 MHz, DMSO-$d_6$) δ ppm 9.03 (s, 1H), 8.48 (d, J=2.8 Hz, 1H), 7.87 (d, J=8.8 Hz, 1H), 7.59 (dd, J=8.8, 2.9 Hz, 1H), 7.42-7.33 (m, 2H), 7.13-7.03 (m, 2H), 5.27 (s, 2H), 4.70 (s, 2H), 2.54 (s, 6H). MS (APCI) m/z 496 (M+H)$^+$.

Example 16 2-(4-chloro-3-fluorophenoxy)-N-(3-{5-[(4-chloro-3-fluorophenoxy)methyl]-1,3,4-oxadiazol-2-yl}bicyclo[1.1.1]pentan-1-yl)acetamide (Compound 115)

Example 16A: 2-(4-chloro-3-fluorophenoxy)acetohydrazide

To a solution of ethyl 2-(4-chloro-3-fluorophenoxy)acetate (38 g, 155 mmol) in ethanol (200 mL) was added hydrazine hydrate (29.3 g, 776 mmol) under $N_2$. The reaction mixture was stirred at 80° C. for 1 hour. After cooling to ambient temperature, the white precipitate was filtered, and the cake was treated with cold ethanol (80 mL) and dried under high vacuum to provide 31.7 g, (93%) of the title compound as white solid. MS (APCI) m/z 219 (M+H)$^+$.

Example 16B: tert-butyl (3-(2-(2-(4-chloro-3-fluorophenoxy)acetyl)hydrazine-1-carbonyl)bicyclo[1.1.1]pentan-1-yl)carbamate To a solution of 3-((tert-butoxycarbonyl)amino)bicyclo[1.1.1]pentane-1-carboxylic acid (Pharmablock, 2.5 g, 11.00 mmol) and Example 16A (2.66 g, 11.55 mmol) in N,N-dimethylformamide (50 mL) was added N,N-diisopropylethylamine (4.27 g, 33.0 mmol) and 2-(7-aza-1H-benzotriazole-1-yl)-1,1,3,3-tetramethyluronium hexafluorophosphate (6.27 g, 16.50 mmol) at 0° C., and the resulting mixture was stirred for 2 hours at ambient temperature. The mixture was diluted with water (250 mL), and the resulting mixture was extracted with ethyl acetate (3×200 mL). The combined organic layer was washed with brine (3×100 mL), dried ($Na_2SO_4$) and concentrated under reduced pressure to provide 6 g, (89%) of the title compound as brown oil. MS (APCI) m/z 428 (M+H)$^+$.

Example 16C: tert-butyl (3-(5-((4-chloro-3-fluorophenoxy)methyl)-1,3,4-oxadiazol-2-yl)bicyclo[1.1.1]pentan-1-yl)carbamate To a suspension of Example 16B (6 g, 9.79 mmol) in acetonitrile (100 mL) was added N,N-diisopropylethylamine (7.61 g, 58.9 mmol) and 4-methylbenzene-1-sulfonyl chloride (7.49 g, 39.3 mmol) at 0° C. The reaction mixture was stirred for 12 hours at ambient temperature and then diluted with ethyl acetate (300 mL). The resulting mixture was washed with saturated aqueous NaHCO$_3$ (2×50 mL), water (50 mL) and brine (50 mL). The organic phase was dried (Na$_2$SO$_4$) and concentrated under reduced pressure. The residue was purified by column chromatography on silica gel (petroleum ether: ethyl acetate=5:1) to provide 3.2 g (73.9%) of the title compound as a white solid. MS (APCI) m/z 410 (M+H)$^+$.

Example 16D: 3-(5-((4-chloro-3-fluorophenoxy)methyl)-1,3,4-oxadiazol-2-yl)bicyclo[1.1.1]pentan-1-amine To a suspension of Example 16C (3.2 g, 6.64 mmol) in dichloromethane (50 mL) was added trifluoroacetic acid (15 mL, 195 mmol) dropwise at 0° C. Then the mixture was stirred for 2 hours at ambient temperature and concentrated. The residue was diluted with water (300 mL), and the aqueous mixture was washed with dichloromethane (2×150 mL). The pH of the aqueous layer was adjusted to 8 with saturated aqueous NaHCO$_3$, and then the aqueous mixture was extracted with ethyl acetate (3×200 mL). The combined organic layer was washed with brine (150 mL), dried (Na$_2$SO$_4$) and concentrated under reduced pressure. The residue was treated with 2-methoxy-2-methylpropane (20 mL), and the resultant solid was collected by filtration and dried under high vacuum to provide 2 g (76%) of the title compound as off white solid. MS (APCI) m/z 310 (M+H)$^+$.

Example 16E: 2-(4-chloro-3-fluorophenoxy)-N-(3-{5-[(4-chloro-3-fluorophenoxy)methyl]-1,3,4-oxadiazol-2-yl}bicyclo[1.1.1]pentan-1-yl)acetamide The title compound was prepared according to the method described in Example 14F replacing Example 14E with Example 16D (0.03 g, 0.097 mmol). $^1$H NMR (501 MHz, DMSO-d$_6$) δ ppm 8.93 (s, 1H), 7.52 (dt, J=13.6, 8.8 Hz, 2H), 7.25 (dd, J=11.3, 2.9 Hz, 1H), 7.09 (dd, J=11.4, 2.9 Hz, 1H), 6.97 (ddd, J=9.0, 2.9, 1.2 Hz, 1H), 6.87 (ddd, J=8.9, 2.9, 1.2 Hz, 1H), 5.43 (s, 2H), 4.51 (s, 2H), 2.50 (s, 6H). MS (APCI) m/z 497 (M+H)$^+$.

Example 17 2-(4-chloro-3-fluorophenoxy)-N-[3-(5-{[6-(trifluoromethyl)pyridin-3-yl]oxy}-1,3,4-oxadiazol-2-yl)bicyclo[1.1.1]pentan-1-yl]acetamide (Compound 116)

Example 17A: methyl 3-(2-(4-chloro-3-fluorophenoxy)acetamido)bicyclo[1.1.1]pentane-1-carboxylate To solution of 2-(4-chloro-3-fluorophenoxy)acetic acid (18 g, 88 mmol) and methyl 3-aminobicyclo[1.1.1]pentane-1-carboxylate (15.63 g, 88 mmol) in N,N-dimethylformamide (300 mL) was added N,N-diisopropylethylamine (77 mL, 440 mmol) and 2-(3H-[1,2,3]triazolo[4,5-b]pyridin-3-yl)-1,1,3,3-tetramethylisouronium hexafluorophosphate (V) (50.2 g, 132 mmol) in portions. The reaction mixture was stirred at ambient temperature for 1 hour. The mixture was diluted with water (1200 mL) and extracted with ethyl acetate (3×500 mL). The combined organic layer was washed with brine (3×300 mL), dried (Na$_2$SO$_4$), and concentrated under reduced pressure. The residue was purified by column chromatography on silica gel (petroleum ether/ethyl acetate 5/1) to provide 28 g (87%) of the title compound as a yellow solid.

Example 17B: 2-(4-chloro-3-fluorophenoxy)-N-(3-(hydrazinecarbonyl)bicyclo[1.1.1]pentan-1-yl)acetamide To a solution of Example 17A (10.5 g, 30.4 mmol) in ethanol (100 mL) was added hydrazine hydrate (7.77 g, 152 mmol) under N$_2$. Then the mixture was stirred at 80° C. for 1 hour. After cooling to 25° C., the mixture was concentrated under reduced pressure, and the resulting white precipitate was collected by filtration. The cake was treated with cold ethanol (50 mL), collected by filtration, and dried under high vacuum to provide the title compound (10.2 g yield 97%) as a white solid.

Example 17C: 2-(4-chloro-3-fluorophenoxy)-N-(3-(5-mercapto-1,3,4-oxadiazol-2-yl)bicyclo[1.1.1]pentan-1-yl)acetamide To solution of Example 17B (9.2 g, 26.7 mmol) in methanol (200 mL) was added potassium hydroxide (2.112 g, 32.0 mmol) at 20° C. under N$_2$. After 30 minutes, carbon disulfide (4.06 g, 53.3 mmol) was added to the mixture. The mixture was stirred for 12 hours in an 80° C. bath. Then the mixture was concentrated under reduced pressure, and the residue was diluted with water (150 mL). The mixture was acidified to pH=3 with HCl (1 N), and the resulting precipitate was collected by filtration and dried under high vacuum to provide the title compound (10 g, yield 91%) as a white solid.

Example 17D: 2-(4-chloro-3-fluorophenoxy)-N-(3-(5-(methylthio)-1,3,4-oxadiazol-2-yl)bicyclo[1.1.1]pentan-1-yl)acetamide To a solution of Example 17C (11 g, 26.8 mmol) in N,N-dimethylformamide (200 mL) was added K$_2$CO$_3$ (7.40 g, 53.5 mmol) and methyl iodide (3.35 mL, 53.5 mmol) at 20° C. under N$_2$. The mixture was stirred for 12 hours at 20° C. Then the mixture was diluted with water (1000 mL) and extracted with ethyl acetate (3×500 mL). The combined organic layer was washed with brine (3×250 mL), dried (Na$_2$SO$_4$) and concentrated under reduced pressure to provide the title compound (10.4 g, yield 96%) as white solid.

Example 17E: 2-(4-chloro-3-fluorophenoxy)-N-{3-[5-(methanesulfonyl)-1,3,4-oxadiazol-2-yl]bicyclo[1.1.1]pentan-1-yl}acetamide To a solution of Example 17D (3.5 g, 8.66 mmol) in acetic acid (60 mL) and water (20 mL) was added a solution of KMnO$_4$ (1.780 g, 11.26 mmol) in water (40 mL) dropwise at 0° C. under N$_2$, and the mixture was stirred for 2 hours at 0° C. Then sodium sulfite was added until the color of the reaction mixture became white from purple The mixture was concentrated. The residue was treated with water (100 mL), filtered and washed with dichloromethane:methanol (3:1, 50 mL). The cake was dried under high vacuum to provide the title compound (5.4 g, yield 82%) as white solid.

Example 17F: 2-(4-chloro-3-fluorophenoxy)-N-[3-(5-{[6-(trifluoromethyl)pyridin-3-yl]oxy}-1,3,4-oxadiazol-2-yl)bicyclo[1.1.1]pentan-1-yl]acetamide A solution of 6-(trifluoromethyl)pyridin-3-ol (42.4 mg, 0.260 mmol) in N,N-dimethylformamide (1 mL) was treated with potassium carbonate (69.1 mg, 0.500 mmol) and Example 17E (83 mg, 0.2 mmol). The reaction mixture was left stirring at 40° C. for 2 hours, concentrated and purified on HPLC (Phenomenex® Luna® C18(2) 5 μm 100 Å AXIA™ column 250 mm×21.2 mm, flow rate 25 mL/minute, 10-80% gradient of acetonitrile in buffer (0.1% trifluoroacetic acid in water)) to provide the title compound (50 mg, 50%). $^1$H NMR (500 MHz, DMSO-$d_6$) δ ppm 8.98 (d, J=2.7 Hz, 1H), 8.92 (s, 1H), 8.35 (dd, J=8.7, 2.6 Hz, 1H), 8.13 (dd, J=8.8, 0.6 Hz, 1H), 7.51 (t, J=8.9 Hz, 1H), 7.09 (dd, J=11.3, 2.8 Hz, 1H), 6.87 (ddd, J=8.9, 2.8, 1.2 Hz, 1H), 4.52 (s, 2H), 2.49 (s, 6H). MS (APCI) m/z 500 (M+H)$^+$.

Example 18 2-(4-chloro-3-fluorophenoxy)-N-[3-(5-{[5-(trifluoromethyl)pyridin-3-yl]oxy}-1,3,4-oxadiazol-2-yl)bicyclo[1.1.1]pentan-1-yl]acetamide (Compound 117)

The title compound was prepared using the method described in Example 17F by replacing 6-(trifluoromethyl)pyridin-3-ol with 5-(trifluoromethyl)pyridin-3-ol (0.021 g, 0.130 mmol) (0.027 g, 54%). $^1$H NMR (400 MHz, DMSO-$d_6$) δ ppm 9.11 (d, J=2.5 Hz, 1H), 9.01 (d, J=1.7 Hz, 1H), 8.93 (s, 1H), 8.59 (t, J=2.3 Hz, 1H), 7.51 (t, J=8.9 Hz, 1H), 7.09 (dd, J=11.4, 2.8 Hz, 1H), 6.87 (ddd, J=8.9, 3.0, 1.2 Hz, 1H), 4.52 (s, 2H), 2.49 (s, 6H). MS (APCI) m/z 500 (M+H)$^+$.

Example 19 2-(4-chloro-3-fluorophenoxy)-N-(3-{5-[(6-cyano-5-methylpyridin-3-yl)oxy]-1,3,4-oxadiazol-2-yl}bicyclo[1.1.1]pentan-1-yl)acetamide (Compound 118)

The title compound was prepared using the method described in Example 17F by replacing 6-(trifluoromethyl)pyridin-3-ol with 5-hydroxy-3-methylpicolinonitrile (0.017 g, 0.130 mmol) (0.030 g, 62%). $^1$H NMR (400 MHz, DMSO-$d_6$) δ ppm 8.92 (s, 1H), 8.81 (d, J=2.6 Hz, 1H), 8.22 (d, J=2.6 Hz, 1H), 7.51 (t, J=8.9 Hz, 1H), 7.09 (dd, J=11.4, 2.9 Hz, 1H), 6.87 (ddd, J=8.9, 2.8, 1.2 Hz, 1H), 4.51 (s, 2H), 2.56 (s, 3H), 2.49 (s, 6H). MS (APCI) m/z 471 (M+H)$^+$.

Example 20 2-(4-chloro-3-fluorophenoxy)-N-(3-{5-[(6-cyanopyridin-3-yl)oxy]-1,3,4-oxadiazol-2-yl}bicyclo[1.1.1]pentan-1-yl)acetamide (Compound 119)

The title compound was prepared using the method described in Example 17F by replacing 6-(trifluoromethyl)pyridin-3-ol with 5-hydroxypicolinonitrile (0.016 g, 0.130 mmol) (0.009 g, 20%). $^1$H NMR (400 MHz, DMSO-$d_6$) δ ppm 8.98 (d, J=2.8 Hz, 1H), 8.92 (s, 1H), 8.33 (dd, J=8.7, 2.7 Hz, 1H), 8.25 (d, J=8.7 Hz, 1H), 7.51 (t, J=8.9 Hz, 1H), 7.09 (dd, J=11.4, 2.9 Hz, 1H), 6.92-6.85 (m, 1H), 4.51 (s, 2H), 2.49 (s, 6H). MS (APCI) m/z 457 (M+H)$^+$.

Example 21 2-(4-chloro-3-fluorophenoxy)-N-(3-{5-[(6-methoxypyridin-3-yl)oxy]-1,3,4-oxadiazol-2-yl}bicyclo[1.1.1]pentan-1-yl)acetamide (Compound 120)

The title compound was prepared using the method described in Example 17F by replacing 6-(trifluoromethyl)pyridin-3-ol with 6-methoxypyridin-3-ol (0.016 g, 0.130 mmol) (0.026 g, 56%). $^1$H NMR (400 MHz, DMSO-$d_6$) δ ppm 8.91 (s, 1H), 8.33 (d, J=3.0 Hz, 1H), 7.91 (dd, J=9.1, 3.0 Hz, 1H), 7.51 (t, J=8.9 Hz, 1H), 7.09 (dd, J=11.4, 2.8 Hz, 1H), 6.95 (d, J=9.0 Hz, 1H), 6.87 (ddd, J=9.0, 2.9, 1.2 Hz, 1H), 4.51 (s, 2H), 3.88 (s, 3H), 2.47 (s, 6H). MS (APCI) m/z 462 (M+H)$^+$.

Example 22 2-(4-chloro-3-fluorophenoxy)-N-(3-{5-[(6-cyclopropylpyridin-3-yl)oxy]-1,3,4-oxadiazol-2-yl}bicyclo[1.1.1]pentan-1-yl)acetamide (Compound 121)

The title compound was prepared using the method described in Example 17F by replacing 6-(trifluoromethyl)pyridin-3-ol with 6-cyclopropylpyridin-3-ol (0.018 g, 0.130 mmol) (0.027 g, 56%). $^1$H NMR (400 MHz, DMSO-$d_6$) δ ppm 8.91 (s, 1H), 8.54 (d, J=2.9 Hz, 1H), 7.83 (dd, J=8.6, 2.9 Hz, 1H), 7.51 (t, J=8.8 Hz, 1H), 7.44 (d, J=8.6 Hz, 1H), 7.09 (dd, J=11.4, 2.9 Hz, 1H), 6.87 (dd, J=9.1, 2.8 Hz, 1H), 4.51 (s, 2H), 2.47 (s, 6H), 2.17 (ddd, J=12.7, 8.2, 4.8 Hz, 1H), 0.98 (dt, J=8.1, 2.8 Hz, 2H), 0.92 (dt, J=5.0, 2.7 Hz, 2H). MS (APCI) m/z 472 (M+H)$^+$.

Example 23 2-(4-chloro-3-fluorophenoxy)-N-{3-[5-({[5-(trifluoromethyl)pyridin-3-yl]oxy}methyl)-1,3,4-oxadiazol-2-yl]bicyclo[1.1.1]pentan-1-yl}acetamide (Compound 122)

Example 23A: 2-(4-chloro-3-fluorophenoxy)-N-(3-(2-(2-chloroacetyl)hydrazine-1-carbonyl)bicyclo[1.1.1]pentan-1-yl)acetamide To a solution of Example 17B (4 g, 11.59 mmol) and triethylamine (3.23 mL, 23.19 mmol) in tetrahydrofuran (100 mL) was added 2-chloroacetyl chloride (1.571 g, 13.91 mmol) dropwise at 0° C. under N$_2$. The mixture was stirred at ambient temperature for 1 hour, diluted with water (500 mL) and extracted with ethyl acetate (3×300 mL). The combined organic layer was washed with saturated NaHCO$_3$ (250 mL) and brine (200 mL), dried (Na$_2$SO$_4$), and concentrated under reduced pressure to provide 5.67 g (97%) of the title compound as earth yellow solid.

Example 23B: 2-(4-chloro-3-fluorophenoxy)-N-(3-(5-(chloromethyl)-1,3,4-oxadiazol-2-yl)bicyclo[1.1.1]pentan-1-yl)acetamide To a solution of Example 23A (6.5 g, 12.86 mmol) in acetonitrile (150 mL) was added N,N-diisopropylethylamine (6.12 mL, 38.6 mmol) and 4-methylbenzene-1-sulfonyl chloride (4.91 g, 25.7 mmol) in portions at 0° C. under N$_2$. The reaction mixture was stirred at ambient temperature for 12 hours and concentrated under reduced pressure at 30° C. The residue was purified by column chromatography on silica gel (petroleum ether/ethyl acetate 5/1) to give crude product. The residue was treated with methyl tert-butyl ether (20 mL), and the solid was collected and dried under high vacuum to provide 4.05 g (78%) of the title compound as earth yellow solid.

Example 23C: 2-(4-chloro-3-fluorophenoxy)-N-{3-[5-({[5-(trifluoromethyl)pyridin-3-yl]oxy}methyl)-1,3,4-oxadiazol-2-yl]bicyclo[1.1.1]pentan-1-yl}acetamide A solution of Example 23B (50 mg, 0.13 mmol) in N,N-dimethylformamide (0.25 mL) was treated with a solution of 5-(trifluoromethyl)pyridin-3-ol (29.3 mg, 0.26 mmol) in N,N-dimethylformamide (0.15 mL) and ground potassium carbonate (53.68 mg, 0.39 mmol). The reaction mixture was stirred at 40° C. for 18 hours and concentrated. HPLC purification (2-coupled C8 5 μm 100 Å columns 30 mm×75 mm each, flow rate of 50 mL/minute, 5-100% gradient of acetonitrile in buffer (10 mM ammonium acetate in water)) provided 29.1 mg (43.8%) of the title compound. $^1$H NMR (400 MHz, DMSO-$d_6$) δ ppm 8.89 (s, 1H), 8.67 (d, J=2.8 Hz, 1H), 8.61-8.59 (m, 1H), 7.97-7.95 (m, 1H), 7.47 (t, J=8.9 Hz, 1H), 7.05 (dd, J=11.4, 2.8 Hz, 1H), 6.83 (ddd, J=8.9, 2.9, 1.2 Hz, 1H), 5.59 (s, 2H), 4.48 (s, 2H), 2.46 (s, 6H). MS (APCI+) m/z 513.3 (M+H)$^+$.

Example 24 2-(4-chloro-3-fluorophenoxy)-N-{3-[5-(4-methylphenoxy)-1,3,4-oxadiazol-2-yl]bicyclo[1.1.1]pentan-1-yl}acetamide (Compound 123)

A solution of Example 17E (25 mg, 0.06 mmol) in N,N-dimethylformamide (0.25 mL) was treated with a solution of p-cresol (9.75 mg, 0.09 mmol) in N,N-dimethylformamide (0.15 mL) and ground potassium carbonate (24.9 mg, 0.18 mmol). The reaction mixture was stirred at 40° C. for 18 hours and concentrated. HPLC purification (2-coupled C8 5 μm 100 Å columns 30 mm×75 mm each, flow rate of 50 mL/minute, 5-100% gradient of acetonitrile in buffer (10 mM ammonium acetate in water)) provided 17.4 mg (65.2%) of the title compound. $^1$H NMR (501 MHz, DMSO-$d_6$) δ ppm 7.50 (t, J=8.8 Hz, 1H), 7.34-7.28 (m, 4H), 7.07 (dd, J=11.3, 2.8 Hz, 1H), 6.88 (ddd, J=8.9, 2.9, 1.2 Hz, 1H), 4.50 (s, 2H), 2.47 (s, 6H), 2.33 (s, 3H). MS (APCI+) m/z 444.2 (M+H)$^+$.

Example 25 2-(4-chloro-3-fluorophenoxy)-N-{3-[5-(2-methoxyphenoxy)-1,3,4-oxadiazol-2-yl]bicyclo[1.1.1]pentan-1-yl}acetamide (Compound 124)

The title compound was prepared using the method described in Example 24 by replacing p-cresol with 2-methoxyphenol (11.20 mg, 0.09 mmol). $^1$H NMR (501 MHz, DMSO-$d_6$) δ ppm 7.52-7.47 (m, 1H), 7.42 (dd, J=8.0, 1.6 Hz, 1H), 7.38-7.34 (m, 1H), 7.24 (dd, J=8.3, 1.4 Hz, 1H), 7.10-7.02 (m, 3H), 6.88 (ddd, J=9.0, 2.9, 1.2 Hz, 1H), 4.50 (s, 2H), 3.79 (s, 3H), 2.48 (s, 6H). MS (APCI+) m/z 460.1 (M+H)$^+$.

Example 26 2-(4-chloro-3-fluorophenoxy)-N-{3-[5-(4-methoxyphenoxy)-1,3,4-oxadiazol-2-yl]bicyclo[1.1.1]pentan-1-yl}acetamide (Compound 125)

The title compound was prepared using the method described in Example 24 by replacing p-cresol with 4-methoxyphenol (11.20 mg, 0.09 mmol). H NMR (501 MHz, DMSO-$d_6$) δ ppm 7.50 (t, J=8.9 Hz, 1H), 7.41-7.35 (m, 2H), 7.08 (dd, J=11.3, 2.9 Hz, 1H), 7.05-7.00 (m, 2H), 6.88 (ddd, J=9.0, 2.9, 1.2 Hz, 1H), 4.50 (s, 2H), 3.78 (s, 3H), 2.47 (s, 6H). MS (APCI+) m/z 460.2 (M+H)$^+$.

Example 27 2-(4-chloro-3-fluorophenoxy)-N-{3-[5-(4-fluorophenoxy)-1,3,4-oxadiazol-2-yl]bicyclo[1.1.1]pentan-1-yl}acetamide (Compound 126)

The title compound was prepared using the method described in Example 24 by replacing p-cresol with 4-fluorophenol (10.11 mg, 0.09 mmol). $^1$H NMR (501 MHz, DMSO-$d_6$) δ ppm 7.53-7.47 (m, 3H), 7.36-7.31 (m, 2H), 7.08 (dd, J=11.3, 2.9 Hz, 1H), 6.90-6.87 (m, 1H), 4.50 (s, 2H), 2.48 (s, 6H). MS (APCI+) m/z 448.1 (M+H)$^+$.

Example 28 2-(4-chloro-3-fluorophenoxy)-N-{3-[5-(2-chlorophenoxy)-1,3,4-oxadiazol-2-yl]bicyclo[1.1.1]pentan-1-yl}acetamide (Compound 127)

The title compound was prepared using the method described in Example 24 by replacing p-cresol with 2-chlorophenol (59 mg, 0.09 mmol). $^1$H NMR (501 MHz, DMSO-$d_6$) δ ppm 7.68 (ddd, J=7.8, 1.6, 0.8 Hz, 2H), 7.53-7.47 (m, 2H), 7.46-7.41 (m, 1H), 7.08 (dd, J=11.3, 2.9 Hz, 1H), 6.88 (ddd, J=9.0, 2.9, 1.2 Hz, 1H), 4.51 (s, 2H), 2.50 (s, 6H). MS (APCI+) m/z 464.1 (M+H)$^+$.

Example 29 2-(4-chloro-3-fluorophenoxy)-N-{3-[5-(4-chlorophenoxy)-1,3,4-oxadiazol-2-yl]bicyclo[1.1.1]pentan-1-yl}acetamide (Compound 128)

The title compound was prepared using the method described in Example 24 by replacing p-cresol with 4-chlorophenol (11.59 mg, 0.09 mmol). $^1$H NMR (501 MHz, DMSO-$d_6$) δ ppm 7.58-7.55 (m, 2H), 7.53-7.47 (m, 3H), 7.08 (dd, J=11.3, 2.9 Hz, 1H), 6.88 (ddd, J=9.0, 2.9, 1.2 Hz, 1H), 4.50 (s, 2H), 2.48 (s, 6H). MS (APCI+) m/z 464.1 (M+H)$^+$.

Example 30 2-(4-chloro-3-fluorophenoxy)-N-{3-[5-(3-cyanophenoxy)-1,3,4-oxadiazol-2-yl]bicyclo[1.1.1]pentan-1-yl}acetamide (Compound 129)

The title compound was prepared using the method described in Example 24 by replacing p-cresol with 3-hydroxybenzonitrile (10.74 mg, 0.09 mmol). $^1$H NMR (501 MHz, DMSO-$d_6$) δ ppm 7.88-7.81 (m, 2H), 7.75-7.71 (m, 1H), 7.50 (td, J=8.9, 4.0 Hz, 2H), 7.08 (dt, J=11.7, 4.2 Hz, 1H), 6.88 (ddd, J=9.0, 2.9, 1.2 Hz, 1H), 4.51 (s, 2H), 2.49 (s, 6H). MS (APCI+) m/z 455.1 (M+H)$^+$.

Example 31 2-(4-chloro-3-fluorophenoxy)-N-{3-[5-(3,4-dimethylphenoxy)-1,3,4-oxadiazol-2-yl]bicyclo[1.1.1]pentan-1-yl}acetamide (Compound 130)

The title compound was prepared using the method described in Example 24 by replacing p-cresol with 3,4-dimethylphenol (11.02 mg, 0.09 mmol). $^1$H NMR (501 MHz, DMSO-$d_6$) δ ppm 7.50 (t, J=8.9 Hz, 1H), 7.27-7.17 (m, 2H), 7.14 (dd, J=8.3, 2.8 Hz, 1H), 7.11-7.04 (m, 1H), 6.88 (ddd, J=9.0, 2.9, 1.2 Hz, 1H), 4.50 (s, 2H), 2.47 (s, 6H), 2.25 (t, J=7.5 Hz, 7H). MS (APCI+) m/z 458.2 (M+H)$^+$.

Example 32 2-(4-chloro-3-fluorophenoxy)-N-(3-{5-[4-(trifluoromethyl)phenoxy]-1,3,4-oxadiazol-2-yl}bicyclo[1.1.1]pentan-1-yl)acetamide (Compound 131)

The title compound was prepared using the method described in Example 24 by replacing p-cresol with 4-(trifluoromethyl)phenol (14.62 mg, 0.09 mmol). $^1$H NMR (501 MHz, DMSO-$d_6$) δ ppm 7.93-7.89 (m, 2H), 7.75-7.71 (m, 2H), 7.50 (t, J=8.9 Hz, 1H), 7.08 (dd, J=11.3, 2.9 Hz, 1H), 6.88 (ddd, J=8.9, 2.8, 1.2 Hz, 1H), 4.51 (s, 2H), 2.49 (s, 6H). MS (APCI+) m/z 498.1 (M+H)$^+$.

Example 33 2-(4-chloro-3-fluorophenoxy)-N-(3-{5-[(4-chlorophenoxy)methyl]-4H-1,2,4-triazol-3-yl}bicyclo[1.1.1]pentan-1-yl)acetamide (Compound 132)

Example 33A: 3-(2-(4-chloro-3-fluorophenoxy)acetamido)bicyclo[1.1.1]pentane-1-carboxamide To a solution of Example 17A (9 g, 26.1 mmol) in methanol (200 mL) was added ammonium hydroxide (100 mL, 770 mmol) at ambient temperature under $N_2$. The reaction mixture was stirred for 12 hours and concentrated under reduced pressure. The resulting residue was treated with methyl tertiary butyl ether (30 mL), the solid was collected by filtration, and the cake was dried under high vacuum to provide 7 g (82%) of the title compound as white solid.

Example 33B: 2-(4-chloro-3-fluorophenoxy)-N-(3-cyanobicyclo[1.1.1]pentan-1-yl)acetamide To a solution of Example 33A (7 g, 21.26 mmol) in tetrahydrofuran (200 mL) was added Burgess reagent (10.13 g, 42.5 mmol) at 0° C., and the resulting mixture was stirred at ambient temperature for 12 hours. The reaction mixture was concentrated under reduced pressure, and the residue was purified by column chromatography on silica gel with dichloromethane/methanol 50/1) to provide crude title compound. The crude title compound was treated with water (150 mL), and the solid was collected by filtration and dried under high vacuum to provide 6 g (92%) of the title compound as white solid.

Example 33C: N-(3-carbamimidoylbicyclo[1.1.1]pentan-1-yl)-2-(4-chloro-3-fluorophenoxy)acetamide A suspension of Example 33B (0.1 g, 0.339 mmol) in ethanol (1 mL) was treated with 4 N hydrogen chloride in dioxane (4.07 mL, 16.29 mmol) and stirred at ambient temperature for 30 minutes. The reaction mixture was concentrated, taken into methanol, cooled to 0° C. and treated with 7 N ammonia in methanol (2.91 mL, 20.36 mmol). The reaction mixture was left stirring at ambient temperature for 18 hours and concentrated to provide the crude title compound.

Example 33D: 2-(4-chloro-3-fluorophenoxy)-N-(3-{5-[(4-chlorophenoxy)methyl]-4H-1,2,4-triazol-3-yl}bicyclo[1.1.1]pentan-1-yl)acetamide A suspension of 2-(4-chlorophenoxy)acetohydrazide (63.7 mg, 0.318 mmol) and Example 33C (99 mg, 0.318 mmol) in methanol (1 mL) was stirred at 75° C. in a sealed vial for 72 hours. The reaction mixture was concentrated and purified on HPLC (Phenomenex® Luna® C18(2) 5 µm 100 Å AXIA™ column 250 mm×21.2 mm, flow rate 25 mL/minute, 10-80% gradient of acetonitrile in buffer (0.1% trifluoroacetic acid in water)) to provide 0.042 g (28%) of the title compound. $^1$H NMR (400 MHz, DMSO-$d_6$) δ ppm 8.82 (s, 1H), 7.50 (t, J=8.9 Hz, 1H), 7.42-7.29 (m, 2H), 7.15-7.00 (m, 3H), 6.87 (ddd, J=9.0, 2.9, 1.2 Hz, 1H), 5.03 (s, 2H), 4.50 (s, 2H), 2.38 (s, 6H). MS (APCI) m/z 478.2 (M+H)$^+$.

Example 34 N-(3-{5-[(4-chloro-3-fluorophenoxy)methyl]-1,3,4-oxadiazol-2-yl}bicyclo-[1.1.1]pentan-1-yl)-2-[(2,2-difluoro-2H-1,3-benzodioxol-5-yl)oxy]acetamide (Compound 133)

Example 34A: 2,2-difluorobenzo[d][1,3]dioxol-5-ol

To a cold solution of 5-bromo-2,2-difluorobenzo[d][1,3]dioxole (5.75 mL, 42.2 mmol) in tetrahydrofuran (80 mL) was added a 2.0 M solution of isopropylmagnesium chloride in tetrahydrofuran (28.1 mL, 56.1 mmol) within 5-10 minutes while maintaining the temperature in the range of 10-20° C. The reaction mixture was stirred at the same temperature for another 15 minutes and then allowed to attain room temperature with continued overnight stirring. The reaction mixture was cooled with an ice bath, triisopropyl borate (12.74 mL, 54.9 mmol) was added dropwise over 2 minutes, and stirring at room temperature was continued for 30 minutes. The reaction mixture was cooled to 10° C. and 10% $H_2SO_4$ solution (50 mL) was added slowly which resulted in a slight exotherm to 20° C. After stirring for 15 minutes, the mixture was partitioned between water and ethyl acetate, and the combined organic extracts were washed with saturated $NaHCO_3$ solution. The organic layer was separated, dried over magnesium sulfate, filtered, and concentrated. The residue was dissolved in 100 mL of tert-butyl methyl ether and cooled to 0° C. 30% Hydrogen peroxide solution in water (5.39 mL, 52.7 mmol) was added slowly, followed by water (60 mL), and the mixture was stirred overnight while warming up to ambient temperature. The reaction mixture was diluted with ethyl acetate and washed twice with sodium thiosulfate solution and brine. The organic layer was dried with magnesium sulfate and filtered. The filtrate was concentrated, and the residue was purified on silica gel (0-50% ethyl acetate in heptane) to give 6.43 g of the title compound as an amber oil. $^1$H NMR (400 MHz, DMSO-$d_6$) δ ppm 9.75 (s, 1H), 7.12 (d, J=8.7 Hz, 1H), 6.75 (d, J=2.4 Hz, 1H), 6.52 (dd, J=8.7, 2.5 Hz, 1H). MS (ESI$^-$) m/z 173.1 (M–H)$^-$.

Example 34B: 2-((2,2-difluorobenzo[d][1,3]dioxol-5-yl)oxy)acetic acid

The title compound was prepared in two steps as described in Examples 15A and 15B, except substituting Example 34A for 6-(trifluoromethyl)pyridine-3-ol. $^1$H NMR (400 MHz, DMSO-$d_6$) δ ppm 13.10 (s, 1H), 7.30 (d, J=8.9 Hz, 1H), 7.13 (d, J=2.6 Hz, 1H), 6.73 (dd, J=8.9, 2.6 Hz, 1H), 4.69 (s, 2H).

Example 34C: N-(3-{5-[(4-chloro-3-fluorophenoxy)methyl]-1,3,4-oxadiazol-2-yl}bicyclo[1.1.1]pentan-1-yl)-2-[(2,2-difluoro-2H-1,3-benzodioxol-5-yl)oxy]acetamide To solution of Example 16D (0.04 g, 0.129 mmol) and Example 34B (0.03 g, 0.129 mmol) in N,N-dimethylformamide (1 mL) was added N,N-diisopropylethylamine (0.056 mL, 0.323 mmol) and 2-(7-aza-1H-benzotriazole-1-yl)-1,1,3,3-tetramethyluronium hexafluorophosphate (0.054 g, 0.142 mmol) under nitrogen. The resulting mixture was stirred for 18 hours and concentrated. The residue was purified on HPLC (Phenomenex® Luna® C18(2) 5 m 100 Å AXIA™ column 250 mm×21.2 mm, flow rate 25 mL/minute, 10-80% gradient of acetonitrile in buffer (0.1% trifluoroacetic acid in water)) to provide 0.046 (68%) of the title compound as a white solid. $^1$H NMR (501 MHz, DMSO-$d_6$) δ ppm 8.90 (s, 1H), 7.53 (t, J=8.9 Hz, 1H), 7.33 (d, J=8.9 Hz, 1H), 7.25 (dd, J=11.2, 2.9 Hz, 1H), 7.15 (d, J=2.5 Hz, 1H), 6.97 (ddd, J=9.0, 2.9, 1.2 Hz, 1H), 6.78 (dd, J=8.9, 2.6 Hz, 1H), 5.41 (s, 2H), 4.47 (s, 2H), 2.48 (s, 6H). MS (APCI) m/z 524.3 (M+H)$^+$.

Example 35 2-(4-chloro-3-fluorophenoxy)-N-{3-[5-(2-methylphenoxy)-1,3,4-oxadiazol-2-yl]bicyclo[1.1.1]pentan-1-yl}acetamide (Compound 134)

The title compound was prepared using the method described in Example 24 by replacing p-cresol with o-cresol (9.75 mg, 0.09 mmol). $^1$H NMR (400 MHz, DMSO-$d_6$) δ ppm 7.49 (t, J=8.9 Hz, 1H), 7.38 (td, J=7.7, 7.3, 1.6 Hz, 2H), 7.33-7.24 (m, 2H), 7.06 (dd, J=11.3, 2.8 Hz, 1H), 6.87 (ddd, J=9.0, 2.9, 1.2 Hz, 1H), 4.49 (s, 2H), 2.47 (s, 6H), 2.21 (s, 3H). MS (APCI) m/z 444.3 (M+H)$^+$.

Example 36 2-(4-chloro-3-fluorophenoxy)-N-{3-[5-(3-methylphenoxy)-1,3,4-oxadiazol-2-yl]bicyclo[1.1.1]pentan-1-yl}acetamide (Compound 135)

The title compound was prepared using the method described in Example 24 by replacing p-cresol with m-cresol (9.75 mg, 0.09 mmol). $^1$H NMR (400 MHz, DMSO-$d_6$) δ ppm 7.50 (d, J=8.9 Hz, 1H), 7.38 (d, J=7.9 Hz, 1H), 7.28-7.16 (m, 2H), 7.11-7.05 (m, 1H), 6.87 (ddd, J=9.0, 2.9, 1.2 Hz, 1H), 4.49 (s, 2H), 2.46 (s, 6H), 2.34 (s, 3H). MS (APCI) m/z 444.3 (M+H)$^+$.

Example 37 2-(4-chloro-3-fluorophenoxy)-N-{3-[5-(3-methoxyphenoxy)-1,3,4-oxadiazol-2-yl]bicyclo[1.1.1]pentan-1-yl}acetamide (Compound 136)

The title compound was prepared using the method described in Example 24 by replacing p-cresol with 3-methoxyphenol (11.20 mg, 0.09 mmol). $^1$H NMR (400 MHz, DMSO-$d_6$) δ ppm 7.48 (t, J=8.9 Hz, 1H), 7.40 (t, J=8.3 Hz, 1H), 7.09-7.04 (m, 2H), 7.00 (ddd, J=8.3, 2.4, 0.9 Hz, 1H), 6.92 (ddd, J=8.4, 2.4, 0.9 Hz, 1H), 6.87 (ddd, J=8.9, 2.8, 1.2 Hz, 1H), 4.49 (s, 2H), 3.77 (s, 3H), 2.46 (s, 6H). MS (APCI+) m/z 460.2 (M+H)$^+$.

Example 38 2-(4-chloro-3-fluorophenoxy)-N-{3-[5-(2-fluorophenoxy)-1,3,4-oxadiazol-2-yl]bicyclo[1.1.1]pentan-1-yl}acetamide (Compound 137)

The title compound was prepared using the method described in Example 24 by replacing p-cresol with 2-fluorophenol (10.11 mg, 0.09 mmol). $^1$H NMR (400 MHz, DMSO-$d_6$) δ ppm 7.65 (td, J=8.1, 1.6 Hz, 1H), 7.51-7.39 (m, 3H), 7.33 (ddt, J=8.2, 7.5, 1.3 Hz, 1H), 7.06 (dd, J=11.3, 2.8 Hz, 1H), 6.87 (ddd, J=9.0, 2.9, 1.2 Hz, 1H), 4.49 (s, 2H), 2.48 (s, 6H). MS (APCI+) m/z 448.2 (M+H)$^+$.

Example 39 2-(4-chloro-3-fluorophenoxy)-N-{3-[5-(3-fluorophenoxy)-1,3,4-oxadiazol-2-yl]bicyclo[1.1.1]pentan-1-yl}acetamide (Compound 138)

The title compound was prepared using the method described in Example 24 by replacing p-cresol with 3-fluorophenol (10.11 mg, 0.09 mmol). $^1$H NMR (400 MHz, DMSO-$d_6$) δ ppm 7.65 (td, J=8.1, 1.6 Hz, 1H), 7.51-7.39 (m, 3H), 7.33 (ddt, J=8.2, 7.5, 1.3 Hz, 1H), 7.06 (dd, J=11.3, 2.8 Hz, 1H), 6.87 (ddd, J=9.0, 2.9, 1.2 Hz, 1H), 4.49 (s, 2H), 2.48 (s, 6H). MS (APCI+) m/z 448.2 (M+H)$^+$.

Example 40 2-(4-chloro-3-fluorophenoxy)-N-(3-{5-[3-(trifluoromethyl)phenoxy]-1,3,4-oxadiazol-2-yl}bicyclo[1.1.1]pentan-1-yl)acetamide (Compound 139)

The title compound was prepared using the method described in Example 24 by replacing p-cresol with 3-(trifluoromethyl)phenol (14.62 mg, 0.09 mmol). $^1$H NMR (400 MHz, DMSO-$d_6$) δ ppm 7.95 (s, 1H), 7.82-7.77 (m, 1H), 7.76-7.73 (m, 2H), 7.49 (t, J=8.9 Hz, 1H), 7.07 (dd, J=11.3, 2.9 Hz, 1H), 6.87 (ddd, J=9.0, 2.9, 1.2 Hz, 1H), 4.49 (s, 2H), 2.48 (s, 6H). MS (APCI+) m/z 513.2 (M+H)$^+$.

Example 41 2-(4-chloro-3-fluorophenoxy)-N-[3-(5-{[(5-fluoropyridin-3-yl)oxy]methyl}-1,3,4-oxadiazol-2-yl)bicyclo[1.1.1]pentan-1-yl]acetamide (Compound 140)

The title compound was prepared using the method described in Example 23C by replacing 5-(trifluoromethyl)pyridin-3-ol with 5-fluoropyridin-3-ol (29.28 mg, 0.26 mmol). $^1$H NMR (400 MHz, DMSO-$d_6$) δ ppm 8.29 (dd, J=2.5, 1.2 Hz, 1H), 8.25 (d, J=2.4 Hz, 1H), 7.59 (dt, J=10.8, 2.4 Hz, 1H), 7.48 (t, J=8.9 Hz, 1H), 7.06 (dd, J=11.3, 2.9 Hz, 1H), 6.87 (ddd, J=9.0, 2.9, 1.2 Hz, 1H), 5.49 (s, 2H), 4.49 (s, 2H), 2.50 (s, 6H). MS (APCI+) m/z 463.2 (M+H)$^+$.

Example 42 2-(4-chloro-3-fluorophenoxy)-N-{3-[5-({[6-(trifluoromethyl)pyridin-3-yl]oxy}methyl)-1,3,4-oxadiazol-2-yl]bicyclo[1.1.1]pentan-1-yl}acetamide (Compound 141)

The title compound was prepared using the method described in Example 23C by replacing 5-(trifluoromethyl)pyridin-3-ol with 6-(trifluoromethyl)pyridin-3-ol (42.23 mg, 0.26 mmol). $^1$H NMR (400 MHz, DMSO-$d_6$) δ ppm 8.54 (d, J=2.8 Hz, 1H), 7.89 (d, J=8.7 Hz, 1H), 7.79-7.71 (m, 1H), 7.48 (t, J=8.8 Hz, 1H), 7.06 (dd, J=11.3, 2.9 Hz, 1H), 6.86 (ddd, J=9.0, 2.9, 1.2 Hz, 1H), 5.57 (s, 2H), 4.49 (s, 2H), 2.50 (s, 6H). MS (APCI+) m/z 513.2 (M+H)+.

Example 43 2-(4-chloro-3-fluorophenoxy)-N-[3-(5-{[(6-methoxypyridin-3-yl)oxy]methyl}-1,3,4-oxadiazol-2-yl)bicyclo[1.1.1]pentan-1-yl]acetamide (Compound 142)

The title compound was prepared using the method described in Example 23C by replacing 5-(trifluoromethyl)pyridin-3-ol with 6-methoxypyridin-3-ol (34.20 mg, 0.26 mmol). $^1$H NMR (400 MHz, DMSO-$d_6$) δ ppm 7.94 (dd, J=3.1, 0.6 Hz, 1H), 7.54-7.45 (m, 2H), 7.06 (dd, J=11.3, 2.9 Hz, 1H), 6.87 (ddd, J=9.0, 2.9, 1.2 Hz, 1H), 6.80 (dd, J=9.0, 0.6 Hz, 1H), 5.35 (s, 2H), 4.49 (s, 2H), 3.79 (s, 3H), 2.49 (s, 6H). MS (APCI+) m/z 475.2 (M+H)$^+$.

Example 44 2-(4-chloro-3-fluorophenoxy)-N-[3-(5-{[(5-methylpyridin-3-yl)oxy]methyl}-1,3,4-oxadiazol-2-yl)bicyclo[1.1.1]pentan-1-yl]acetamide (Compound 143)

The title compound was prepared using the method described in Example 23C by replacing 5-(trifluoromethyl)pyridin-3-ol with 5-methylpyridin-3-ol (28.26 mg, 0.26 mmol). $^1$H NMR (400 MHz, DMSO-$d_6$) δ ppm 8.17 (d, J=2.8 Hz, 1H), 8.08 (dd, J=1.7, 0.8 Hz, 1H), 7.48 (t, J=8.9 Hz, 1H), 7.38 (ddd, J=2.6, 1.7, 0.8 Hz, 1H), 7.06 (dd, J=11.3, 2.9 Hz, 1H), 6.87 (ddd, J=9.0, 2.9, 1.2 Hz, 1H), 5.42 (s, 2H), 4.49 (s, 2H), 2.50 (s, 6H), 2.29 (s, 4H). MS (APCI+) m/z 459.2 (M+H)$^+$.

Example 45 2-(4-chloro-3-fluorophenoxy)-N-[3-(5-{[(5-cyanopyridin-3-yl)oxy]methyl}-1,3,4-oxadiazol-2-yl)bicyclo[1.1.1]pentan-1-yl]acetamide (Compound 144)

The title compound was prepared using the method described in Example 23C by replacing 5-(trifluoromethyl)

pyridin-3-ol with 5-hydroxynicotinonitrile (31.10 mg, 0.26 mmol). $^1$H NMR (400 MHz, DMSO-d$_6$) δ ppm 8.67 (d, J=2.9 Hz, 1H), 8.66 (d, J=1.6 Hz, 1H), 8.08 (dd, J=3.0, 1.6 Hz, 1H), 7.48 (t, J=8.9 Hz, 1H), 7.06 (dd, J=11.3, 2.9 Hz, 1H), 6.87 (ddd, J=9.1, 2.9, 1.2 Hz, 1H), 5.53 (s, 2H), 4.49 (s, 2H), 2.50 (s, 6H). MS (APCI+) m/z 470.2 (M+H)$^+$.

Example 46 2-(4-chloro-3-fluorophenoxy)-N-[3-(5-{[(5-chloro-6-methylpyridin-3-yl)oxy]methyl}-1,3,4-oxadiazol-2-yl)bicyclo[1.1.1]pentan-1-yl]acetamide (Compound 145)

The title compound was prepared using the method described in Example 23C by replacing 5-(trifluoromethyl)pyridin-3-ol with 5-chloro-6-methylpyridin-3-ol (31.17 mg, 0.26 mmol). $^1$H NMR (400 MHz, DMSO-d$_6$) δ ppm 8.23 (d, J=2.7 Hz, 1H), 7.71 (d, J=2.6 Hz, 1H), 7.48 (t, J=8.9 Hz, 1H), 7.06 (dd, J=11.3, 2.8 Hz, 1H), 6.86 (ddd, J=9.0, 2.9, 1.2 Hz, 1H), 5.46 (s, 2H), 4.49 (s, 2H), 2.49 (s, 6H), 2.46 (s, 3H). MS (APCI+) m/z 493.1 (M+H)$^+$.

Example 47 2-(4-chloro-3-fluorophenoxy)-N-[3-(5-{[(6-methylpyridin-3-yl)oxy]methyl}-1,3,4-oxadiazol-2-yl)bicyclo[1.1.1]pentan-1-yl]acetamide (Compound 146)

The title compound was prepared using the method described in Example 23C by replacing 5-(trifluoromethyl)pyridin-3-ol with 6-methylpyridin-3-ol (28.26 mg, 0.26 mmol). $^1$H NMR (400 MHz, DMSO-d$_6$) δ ppm 8.21 (d, J=2.9 Hz, 1H), 7.48 (t, J=8.9 Hz, 1H), 7.42 (dd, J=8.6, 3.1 Hz, 1H), 7.23 (d, J=8.6 Hz, 1H), 7.06 (dd, J=11.3, 2.9 Hz, 1H), 6.86 (ddd, J=9.0, 2.9, 1.2 Hz, 1H), 5.40 (s, 2H), 4.49 (s, 2H), 2.49 (s, 6H), 2.40 (s, 3H). MS (APCI+) m/z 459.2 (M+H)$^+$.

Example 48 2-(4-chloro-3-fluorophenoxy)-N-(3-{5-[({6-[(propan-2-yl)oxy]pyridin-3-yl}oxy)methyl]-1,3,4-oxadiazol-2-yl}bicyclo[1.1.1]pentan-1-yl)acetamide (Compound 147)

The title compound was prepared using the method described in Example 23C by replacing 5-(trifluoromethyl)pyridin-3-ol with 6-isopropoxypyridin-3-ol (39.66 mg, 0.26 mmol). $^1$H NMR (400 MHz, DMSO-d$_6$) δ ppm 7.93-7.89 (m, 1H), 7.52-7.45 (m, 2H), 7.06 (dd, J=11.3, 2.8 Hz, 1H), 6.87 (ddd, J=9.0, 2.9, 1.2 Hz, 1H), 6.71 (dd, J=9.0, 0.6 Hz, 1H), 5.33 (s, 2H), 5.10 (hept, J=6.2 Hz, 1H), 4.49 (s, 2H), 2.49 (s, 6H), 1.25 (d, J=6.2 Hz, 6H). MS (APCI+) m/z 503.1 (M+H)$^+$.

Example 49 2-(4-chloro-3-fluorophenoxy)-N-[3-(5-{[(5-chloropyridin-3-yl)oxy]methyl}-1,3,4-oxadiazol-2-yl)bicyclo[1.1.1]pentan-1-yl]acetamide (Compound 148)

The title compound was prepared using the method described in Example 23C by replacing 5-(trifluoromethyl)pyridin-3-ol with 5-chloropyridin-3-ol (33.54 mg, 0.26 mmol). $^1$H NMR (400 MHz, DMSO-d$_6$) δ ppm 8.36 (d, J=2.5 Hz, 1H), 8.29 (d, J=1.9 Hz, 1H), 7.76 (t, J=2.3 Hz, 1H), 7.48 (t, J=8.9 Hz, 1H), 7.06 (dd, J=11.3, 2.9 Hz, 1H), 6.87 (ddd, J=8.9, 2.8, 1.2 Hz, 1H), 5.50 (s, 2H), 4.49 (s, 2H), 2.50 (s, 6H). MS (APCI+) m/z 479.1 (M+H)$^+$.

Example 50 2-(4-chloro-3-fluorophenoxy)-N-[3-(5-{[(1H-pyrrolo[3,2-b]pyridin-6-yl)oxy]methyl}-1,3,4-oxadiazol-2-yl)bicyclo[1.1.1]pentan-1-yl]acetamide (Compound 149)

The title compound was prepared using the method described in Example 23C by replacing 5-(trifluoromethyl)pyridin-3-ol with 1H-pyrrolo[3,2-b]pyridin-6-ol (34.73 mg, 0.26 mmol). $^1$H NMR (400 MHz, DMSO-d$_6$) δ ppm 8.14 (d, J=2.6 Hz, 1H), 7.54 (dd, J=2.6, 0.9 Hz, 1H), 7.52 (d, J=3.3 Hz, 1H), 7.48 (t, J=8.9 Hz, 1H), 7.06 (dd, J=11.3, 2.8 Hz, 1H), 6.86 (ddd, J=9.0, 2.9, 1.2 Hz, 1H), 6.50 (dd, J=3.3, 0.9 Hz, 1H), 5.42 (s, 2H), 4.49 (s, 2H), 2.49 (s, 6H). MS (APCI+) m/z 484.1 (M+H)$^+$.

Example 51 2-(4-chloro-3-fluorophenoxy)-N-[3-(5-{[(6-cyclopropylpyridin-3-yl)oxy]methyl}-1,3,4-oxadiazol-2-yl)bicyclo[1.1.1]pentan-1-yl]acetamide (Compound 150)

The title compound was prepared using the method described in Example 23C by replacing 5-(trifluoromethyl)pyridin-3-ol with 6-cyclopropylpyridin-3-ol (35.0 mg, 0.26 mmol). $^1$H NMR (400 MHz, DMSO-d$_6$) δ ppm 8.17 (d, J=3.0 Hz, 1H), 7.48 (t, J=8.9 Hz, 1H), 7.39 (dd, J=8.6, 3.0 Hz, 1H), 7.23 (dd, J=8.6, 0.7 Hz, 1H), 7.06 (dd, J=11.3, 2.8 Hz, 1H), 6.86 (ddd, J=9.0, 2.9, 1.2 Hz, 1H), 5.38 (s, 2H), 4.49 (s, 2H), 2.49 (s, 6H), 2.08-2.00 (m, 1H), 0.93-0.87 (m, 2H), 0.82-0.77 (m, 2H). MS (APCI+) m/z 485.2 (M+H)$^+$.

Example 52 2-(4-chloro-3-fluorophenoxy)-N-[3-(5-{[(6-methoxy-2-methylpyridin-3-yl)oxy]methyl}-1,3,4-oxadiazol-2-yl)bicyclo[1.1.1]pentan-1-yl]acetamide (Compound 151)

The title compound was prepared using the method described in Example 23C by replacing 5-(trifluoromethyl)pyridin-3-ol with 6-methoxy-2-methylpyridin-3-ol (36.03 mg, 0.26 mmol). $^1$H NMR (400 MHz, DMSO-d$_6$) δ ppm 7.55-7.45 (m, 2H), 7.06 (dd, J=11.3, 2.8 Hz, 1H), 6.87 (ddd, J=9.0, 2.9, 1.2 Hz, 1H), 6.62 (dd, J=8.8, 0.8 Hz, 1H), 5.30 (s, 2H), 4.49 (s, 2H), 3.77 (s, 3H), 2.49 (s, 6H), 2.26 (s, 3H). MS (APCI+) m/z 489.1 (M+H)$^+$.

Example 53 2-(4-chloro-3-fluorophenoxy)-N-[3-(5-{[(furo[3,2-b]pyridin-6-yl)oxy]methyl}-1,3,4-oxadiazol-2-yl)bicyclo[1.1.1]pentan-1-yl]acetamide (Compound 152)

The title compound was prepared using the method described in Example 23C by replacing 5-(trifluoromethyl)pyridin-3-ol with furo[3,2-b]pyridin-6-ol (34.99 mg, 0.26 mmol). $^1$H NMR (400 MHz, DMSO-d$_6$) δ ppm 8.36 (d, J=2.5 Hz, 1H), 8.17 (d, J=2.3 Hz, 1H), 7.91 (dd, J=2.6, 1.0 Hz, 1H), 7.48 (t, J=8.9 Hz, 1H), 7.06 (dd, J=6.2, 5.4, 2.9 Hz, 2H), 6.86 (ddd, J=9.0, 2.8, 1.2 Hz, 1H), 5.49 (s, 2H), 4.49 (s, 2H), 2.50 (s, 6H). MS (APCI+) m/z 485.1 (M+H)$^+$.

Example 54 2-(4-chloro-3-fluorophenoxy)-N-[3-(5-{[(2-ethyl-6-methylpyridin-3-yl)oxy]methyl}-1,3,4-oxadiazol-2-yl)bicyclo[1.1.1]pentan-1-yl]acetamide (Compound 153)

The title compound was prepared using the method described in Example 23C by replacing 5-(trifluoromethyl)pyridin-3-ol with 2-ethyl-6-methylpyridin-3-ol hydrochloride (44.96 mg, 0.26 mmol). $^1$H NMR (400 MHz, DMSO-d$_6$) δ ppm 7.48 (t, J=8.9 Hz, 1H), 7.42 (d, J=8.4 Hz, 1H), 7.09-7.04 (m, 2H), 6.86 (ddd, J=8.9, 2.8, 1.2 Hz, 1H), 5.38 (s, 2H), 4.49 (s, 2H), 2.67 (q, J=7.5 Hz, 2H), 2.48 (s, 6H), 2.36 (s, 3H), 1.10 (t, J=7.5 Hz, 3H). MS (APCI+) m/z 487.2 (M+H)$^+$.

Example 55 2-(4-chloro-3-fluorophenoxy)-N-{3-[5-({[6-(propan-2-yl)pyridin-3-yl]oxy}methyl)-1,3,4-oxadiazol-2-yl]bicyclo[1.1.1]pentan-1-yl}acetamide (Compound 154)

The title compound was prepared using the method described in Example 23C by replacing 5-(trifluoromethyl)pyridin-3-ol with 6-isopropylpyridin-3-ol (35.52 mg, 0.26 mmol). $^1$H NMR (400 MHz, DMSO-d$_6$) δ ppm 8.27-8.23 (m, 1H), 7.52-7.42 (m, 2H), 7.25 (d, J=8.6 Hz, 1H), 7.06 (dd, J=11.3, 2.9 Hz, 1H), 6.86 (ddd, J=9.0, 2.9, 1.2 Hz, 1H), 5.40 (s, 2H), 4.49 (s, 2H), 2.97 (hept, J=6.9 Hz, 1H), 2.49 (s, 6H), 1.19 (d, J=6.9 Hz, 6H). MS (APCI+) m/z 487.2 (M+H)$^+$.

Example 56 2-(4-chloro-3-fluorophenoxy)-N-[3-(5-{[(6-methoxy-5-methylpyridin-3-yl)oxy]methyl}-1,3,4-oxadiazol-2-yl)bicyclo[1.1.1]pentan-1-yl]acetamide (Compound 155)

The title compound was prepared using the method described in Example 23C by replacing 5-(trifluoromethyl)pyridin-3-ol with 6-methoxy-5-methylpyridin-3-ol (36.03 mg, 0.26 mmol). $^1$H NMR (400 MHz, DMSO-d$_6$) δ ppm 7.75 (dd, J=2.9, 0.8 Hz, 1H), 7.48 (t, J=8.9 Hz, 1H), 7.38 (dd, J=3.1, 1.1 Hz, 1H), 7.06 (dd, J=11.3, 2.8 Hz, 1H), 6.87 (ddd, J=8.9, 2.8, 1.2 Hz, 1H), 5.32 (s, 2H), 4.49 (s, 2H), 3.81 (s, 3H), 2.49 (s, 6H), 2.12 (d, J=0.8 Hz, 3H). MS (APCI+) m/z 489.1 (M+H)$^+$.

Example 57 2-(4-chloro-3-fluorophenoxy)-N-[3-(5-{[(6-cyano-5-methylpyridin-3-yl)oxy]methyl}-1,3,4-oxadiazol-2-yl)bicyclo[1.1.1]pentan-1-yl]acetamide (Compound 156)

The title compound was prepared using the method described in Example 23C by replacing 5-(trifluoromethyl)pyridin-3-ol with 5-hydroxy-3-methylpicolinonitrile (34.73 mg, 0.26 mmol). $^1$H NMR (400 MHz, DMSO-d$_6$) δ ppm 8.36 (d, J=2.8 Hz, 1H), 7.65 (dd, J=2.9, 0.8 Hz, 1H), 7.48 (t, J=8.8 Hz, 1H), 7.06 (dd, J=11.3, 2.9 Hz, 1H), 6.87 (ddd, J=9.0, 2.9, 1.2 Hz, 1H), 5.54 (s, 2H), 4.49 (s, 2H), 2.50 (s, 6H), 2.48 (s, 3H). MS (APCI+) m/z 484.1 (M+H)$^+$.

Example 58 2-(4-chloro-3-fluorophenoxy)-N-[3-(5-{[(6-cyanopyridin-3-yl)oxy]methyl}-1,3,4-oxadiazol-2-yl)bicyclo[1.1.1]pentan-1-yl]acetamide (Compound 157)

The title compound was prepared using the method described in Example 23C by replacing 5-(trifluoromethyl)pyridin-3-ol with 5-hydroxypicolinonitrile (31.10 mg, 0.26 mmol). $^1$H NMR (400 MHz, DMSO-d$_6$) δ ppm 8.54 (dd, J=3.0, 0.6 Hz, 1H), 8.02 (dd, J=8.7, 0.6 Hz, 1H), 7.72 (dd, J=8.8, 3.0 Hz, 1H), 7.48 (t, J=8.9 Hz, 1H), 7.06 (dd, J=11.3, 2.9 Hz, 1H), 6.86 (ddd, J=9.0, 2.9, 1.2 Hz, 1H), 5.58 (s, 2H), 4.49 (s, 2H), 2.50 (s, 6H). MS (APCI+) m/z 470.1 (M+H)$^+$.

Example 59 2-(4-chlorophenoxy)-N-(3-{3-[(3,4-dichlorophenoxy)methyl]-1,2,4-oxadiazol-5-yl}bicyclo[1.1.1]pentan-1-yl)acetamide (Compound 158)

Example 59A: 2-(3,4-dichlorophenoxy)acetonitrile

To a mixture of 3,4-dichlorophenol (3.26 g, 20 mmol) and potassium carbonate (1.94 g, 14 mmol) in acetone (10 mL) was added bromoacetonitrile (3.12 g, 26 mmol). The mixture was stirred at reflux for 3 hours and then at room temperature overnight. Water (10 mL) was added. The mixture was stirred for 1 hour and then concentrated. The resulting solid was collected, washed with water (30 mL×3), and then dried to give 4.06 g of the title compound as a white solid. $^1$H NMR (400 MHz, CDCl$_3$) δ ppm 7.42 (d, J=8, 1H), 7.11 (d, J=2, 1H), 6.86 (dd, J=8, 2, 1H), 4.76 (s, 2H). MS (ESI+) m/z 203 (M+H)$^+$.

Example 59B: 2-(3,4-dichlorophenoxy)-N-hydroxyacetimidamide

A mixture of 2-(3,4-dichlorophenoxy)acetonitrile (1.455 g, 7.2 mmol, Example 59A) and hydroxylamine (7.13 g, 50%, 108 mmol) in ethanol (10 mL) was heated up at reflux for 1.5 hours. The mixture was then concentrated to give 1.7 g of the title compound. LC/MS (ESI+) m/z 235 (M+H)$^+$.

Example 59C: tert-butyl (3-(3-((3,4-dichlorophenoxy)methyl)-1,2,4-oxadiazol-5-yl)bicyclo[1.1.1]pentan-1-yl)carbamate A mixture of 3-((tert-butoxycarbonyl)amino)bicyclo[1.1.1]pentane-1-carboxylic acid (1.557 g, 6.85 mmol), and 1,1'-carbonyldiimidazole (1.21 g, 7.47 mol) in N,N-dimethylformamide (8 mL) was stirred at room temperature for 1 hour, and then 2-(3,4-dichlorophenoxy)-N-hydroxyacetimidamide (1.69 g, 7.19 mmol, Example 59B) in N,N-dimethylformamide (4 mL) was added. The mixture was stirred at 90° C. overnight. Then the N,N-dimethylformamide was removed under vacuum and ethyl acetate (100 mL) was added. The organic phase was washed with water (100 mL×3), dried over Na$_2$SO$_4$, filtered and concentrated to give 3 g of solid. The solid was dissolved in ethyl acetate (8 mL) and purified by flash column chromatography on silica gel (80 g) eluted with ethyl acetate to give 1.99 g of the title compound (68% yield) as a white solid. $^1$H NMR (400 MHz, DMSO-d$_6$) δ ppm 7.80 (brs, 1H), 7.56 (d, J=8, 1H), 7.39 (d, J=2, 1H), 7.07 (dd, J=8, 2, 1H), 5.32 (s, 2H), 2.41 (s, 6H), 1.40 (s, 9H). MS (ESI$^-$) m/z 424 (M–H)$^-$.

Example 59D: 3-(3-((3,4-dichlorophenoxy)methyl)-1,2,4-oxadiazol-5-yl)bicyclo[1.1.1]pentan-1-amine hydrochloride To tert-butyl (3-(3-((3,4-dichlorophenoxy)methyl)-1,2,4-oxadiazol-5-yl)bicyclo[1.1.1]pentan-1-yl)carbamate (0.98 g, 2.3 mmol, Example 59C) in dichloromethane (3 mL) was added 4 N HCl in dioxane (17.3 mL, 69 mmol). The mixture was stirred at room temperature for 2 hours, and then concentrated to give 0.838 g of the title compound (100% yield) as a white solid. $^1$H NMR (400 MHz, DMSO-d$_6$) δ ppm 9.08 (br s, 3H), 7.57 (d, J=8, 1H), 7.39 (d, J=2, 1H), 7.07 (dd, J=8, 2, 1H), 5.34 (s, 2H), 2.49 (s, 6H). MS (ESI+) m/z 327 (M+H)$^+$.

Example 59E: 2-(4-chlorophenoxy)-N-(3-{3-[(3,4-dichlorophenoxy)methyl]-1,2,4-oxadiazol-5-yl}bicyclo[1.1.1]pentan-1-yl)acetamide To 3-(3-((3,4-dichlorophenoxy)methyl)-1,2,4-oxadiazol-5-yl)bicyclo[1.1.1]pentan-1-amine hydrochloride (0.138 g, 0.38 mmol, Example 59D) in dichloromethane (4 mL) was added N,N-diisopropylethylamine (0.147 g, 1.14 mmol) followed by 2-(4-chlorophenoxy)acetyl chloride (0.078 g, 0.38 mmol) in dichloromethane (2 mL). The mixture was stirred at room temperature for 30 minutes, and then concentrated to give 0.2 g of solid. The solid was dissolved in ethyl acetate (1 mL) and purified by flash column chromatography on silica gel (40 g) eluted with heptane/ethyl acetate (10 to 50%) to give 0.122 g of the title compound as a white solid. $^1$H NMR (400 MHz, DMSO-d$_6$) δ ppm 8.93 (s, 1H), 7.56 (d, J=8, 1H), 7.39 (d, J=2, 1H), 7.35 (d, J=8, 2H), 7.07 (dd, J=8, 2, 1H), 6.99 (d, J=8H, 2H), 5.32 (s, 2H), 4.47 (s, 2H), 2.50 (s, 6H). MS (ESI+) m/z 494 (M+H)$^+$.

Example 60 2-(4-chloro-3-fluorophenoxy)-N-{3-[3-({[5-(trifluoromethyl)pyridin-3-yl]oxy}methyl)-1,2,4-oxadiazol-5-yl]bicyclo[1.1.1]pentan-1-yl}acetamide (Compound 159)

Example 60A: 2-chloro-N-hydroxyacetimidamide

Sodium ethanolate (2.94 g, 43.2 mmol) was added to a suspension of hydroxylamine hydrochloride (3.0 g, 43.2 mmol) in ethanol (100 mL) at 0° C. After stirring for 10 minutes, 2-chloroacetonitrile (3.26 g, 43.2 mmol) was added dropwise. The reaction mixture was stirred for 2 hours at 25° C. and was filtered. The filtrate was concentrated under reduced pressure to provide the title compound (3 g, 60.8% yield). $^1$H NMR (400 MHz, DMSO-d$_6$) δ ppm 4.00 (s, 2H), 5.62 (br. s., 2H), 9.43 (s, 1H).

Example 60B: methyl 3-(2-(4-chloro-3-fluorophenoxy)acetamido)bicyclo[0.1.1]pentane-1-carboxylate To solution of 2-(4-chloro-3-fluorophenoxy)acetic acid (18 g, 88 mmol) and methyl 3-aminobicyclo[1.1.1]pentane-1-carboxylate (15.63 g, 88 mmol) in dimethylformamide (300 mL) was added diisopropylethylamine (77 mL, 440 mmol) and 2-(3H-[1,2,3]triazolo[4,5-b]pyridin-3-yl)-1,1,3,3-tetramethylisouronium hexafluorophosphate (V) (50.2 g, 132 mmol) in portions. The mixture was stirred at 25° C. for 1 hour. The mixture was diluted with water (1200 mL), and extracted with ethyl acetate (3×500 mL). The combined organic layers were washed with brine (3×300 mL), dried over anhydrous Na$_2$SO$_4$, and concentrated under reduced pressure. The residue was purified by column chromatography on silica gel (petroleum ether:ethyl acetate=5:1) to provide the title compound (28 g, 87% yield). $^1$H NMR: (400 MHz, CDCl$_3$) C ppm 2.44 (s, 6H), 3.70 (s, 3H), 4.39 (s, 2H), 6.68 (dd, 1H), 6.76 (dd, 1H), 6.87 (br. s., 1H), 7.29-7.37 (m, 1H).

Example 60C: 3-(2-(4-chloro-3-fluorophenoxy)acetamido)bicyclo[1.1.1]pentane-1-carboxylic acid To a solution of the product of Example 60B (5 g, 13.7 mmol) in tetrahydrofuran (50 mL), ethanol (15 mL) and water (15 mL) was added lithium hydroxide hydrate (1.15 g, 27.5 mmol) at 20° C. The mixture was stirred at 20° C. for 12 hours. The resulting solution was concentrated under reduced pressure, and the residue was diluted with water (200 mL). The mixture was adjusted to pH=3 by adding HCl (1 M) and extracted with ethyl acetate (2×300 mL). The combined organic phases were dried with anhydrous Na$_2$SO$_4$ and concentrated under reduced pressure to provide the title compound (4.5 g, 99% yield). $^1$H NMR: (DMSO-d$_6$, 400 MHz) δ ppm 2.18 (s, 6H), 4.44 (s, 2H), 6.81 (dd, J=9.04, 1.98 Hz, 1H), 7.04 (dd, J=11.25, 2.87 Hz, 1H), 7.42-7.50 (m, 1H), 8.75 (s, 1H), 12.44 (br. s., 1H).

Example 60D: 2-(4-chloro-3-fluorophenoxy)-N-(3-(((2-chloroacetimidamido)-oxy)carbonyl)bicyclo[1.1.1]pentan-1-yl)acetamide To a solution of the product of Example 60C (3.0 g, 9.08 mmol) in N,N-dimethylformamide (150 mL) were added 1H-benzo[d][1,2,3]triazol-1-ol hydrate (0.556 g, 3.63 mmol), N-ethyl-N-isopropylpropan-2-amine (4.76 mL, 27.3 mmol) and 2-(3H-[1,2,3]triazolo[4,5-b]pyridin-3-yl)-1,1,3,3-tetramethylisouronium tetrafluoroborate (3.51 g, 10.90 mmol) at 25° C. Example 60A (1.038 g, 9.08 mmol) was added to the above mixture at 0° C. The mixture was stirred at 25° C. for 6 hours, diluted with ethyl acetate (500 mL), and washed with water (3×250 mL). The organic layer was washed with brine (3×250 mL), dried over anhydrous Na$_2$SO$_4$, and concentrated under reduced pressure. The residue was washed with methyl tert-butyl ether to provide the title compound (2.75 g, 70% yield). $^1$H NMR (400 MHz, DMSO-d$_6$) δ ppm 2.33 (s, 3H), 4.08 (s, 1H), 4.48 (s, 1H), 6.70 (br. s., 1H), 6.85 (dd, J=1.8, 8.8 Hz, 1H), 7.07 (dd, J=2.6, 11.5 Hz, 1H), 7.50 (t, J=8.8 Hz, 1H), 8.79 (s, 1H).

Example 60E: 2-(4-chloro-3-fluorophenoxy)-N-(3-(3-(chloromethyl)-1,2,4-oxadiazol-5-yl)bicyclo[1.1.1]pentan-1-yl)acetamide A solution of the product of Example 60D (5.5 g, 12.8 mmol) in toluene (2000 mL) in a flask equipped with a Dean-Stark trap was heated to 110° C. for 48 hours. The solution was concentrated under reduced pressure. The residue was washed with methyl tert-butyl ether and filtered. The filtrate was concentrated under reduced pressure, and the residue was purified by column chromatography on silica gel (petroleum ether/ethyl acetate) to provide the title compound (2.59 g, 52% yield). $^1$H NMR (400 MHz, CDCl$_3$) δ ppm 2.70 (s, 6H), 4.43 (s, 2H), 4.59 (s, 2H), 6.69 (td, J=1.2, 9.0 Hz, 1H), 6.77 (dd, J=3.1, 10.1 Hz, 1H), 6.96 (br. s., 1H), 7.34 (t, J=8.6 Hz, 1H).

Example 60F: 2-(4-chloro-3-fluorophenoxy)-N-{3-[3-({[5-(trifluoromethyl)pyridin-3-yl]oxy}methyl)-1,2,4-oxadiazol-5-yl]bicyclo[1.1.1]pentan-1-yl}acetamide A mixture of the product of Example 60E (60.0 mg, 0.155 mmol), 5-(trifluoromethyl)pyridin-3-ol (38.0 mg, 0.233 mmol), potassium iodide (1.289 mg, 7.77 µmol), and potassium carbonate (42.9 mg, 0.311 mmol) in acetone (2.5 mL) was heated at 140° C. in a Biotage® Initiator microwave reactor for 30 minutes. The reaction mixture was concentrated under reduced pressure, and the residue was treated with brine and extracted with ethyl acetate. The organic layer was concentrated under reduced pressure, and the residue was purified by reverse-phase HPLC performed on a Zorbax Rx-C18 column (250×21.2 mm, 7 µm particle size) using a gradient of 10% to 95% acetonitrile:0.1% aqueous trifluoroacetic acid over 30 minutes at a flow rate of 18 mL/minute to provide the title compound (15.7 mg, 20% yield). $^1$H NMR (400 MHz, DMSO-d$_6$) δ ppm 8.90 (s, 1H), 8.66 (d, J=2.8 Hz, 1H), 8.61-8.54 (m, 1H), 7.92 (t, J=2.2 Hz, 1H), 7.47 (t, J=8.9 Hz, 1H), 7.05 (dd, J=11.3, 2.8 Hz, 1H), 6.83 (ddd, J=9.0, 2.9, 1.2 Hz, 1H), 5.47 (s, 2H), 4.48 (s, 2H), 2.51 (s, 6H); MS (ESI$^+$) m/z 513.0 (M+H)$^+$.

Example 61 2-(4-chloro-3-fluorophenoxy)-N-{3-[3-({[2-(trifluoromethyl)pyridin-4-yl]oxy}methyl)-1,2,4-oxadiazol-5-yl]bicyclo[1.1.1]pentan-1-yl}acetamide (Compound 160)

The reaction described in Example 60F substituting 2-(trifluoromethyl)pyridin-4-ol for 5-(trifluoromethyl)pyridin-3- ol gave the title compound. ¹H NMR (500 MHz, DMSO-d₆) δ ppm 8.94 (s, 1H), 8.61 (d, J=5.8 Hz, 1H), 7.59 (d, J=2.4 Hz, 1H), 7.49 (t, J=8.9 Hz, 1H), 7.38 (dd, J=5.7, 2.5 Hz, 1H), 7.08 (dd, J=11.4, 2.8 Hz, 1H), 6.86 (ddd, J=9.0, 2.9, 1.2 Hz, 1H), 5.52 (s, 2H), 4.50 (s, 2H), 2.53 (s, 6H); MS (ESI⁺) m/z 513.1 (M+H)⁺.

Example 62 2-(4-chloro-3-fluorophenoxy)-N-{3-[3-({[6-(trifluoromethyl)pyridin-3-yl]oxy}methyl)-1,2,4-oxadiazol-5-yl]bicyclo[1.1.1]pentan-1-yl}acetamide (Compound 161)

The reaction described in Example 60F substituting 6-(trifluoromethyl)pyridin-3-ol for 5-(trifluoromethyl)pyridin-3-ol gave the title compound. ¹H NMR (500 MHz, DMSO-d₆) C ppm 8.94 (s, 1H), 8.54 (d, J=2.9 Hz, 1H), 7.89 (d, J=8.7 Hz, 1H), 7.78-7.71 (m, 1H), 7.49 (t, J=8.9 Hz, 1H), 7.08 (dd, J=11.3, 2.8 Hz, 1H), 6.85 (ddd, J=8.9, 2.8, 1.2 Hz, 1H), 5.49 (s, 2H), 4.50 (s, 2H), 2.53 (s, 6H); MS (ESI⁺) m/z 513.1 (M+H)⁺.

Example 63 2-(4-chloro-3-fluorophenoxy)-N-{3-[3-({[5-chloro-6-(trifluoromethyl)pyridin-3-yl]oxy}methyl)-1,2,4-oxadiazol-5-yl]bicyclo[1.1.1]pentan-1-yl}acetamide (Compound 162)

The reaction described in Example 60F substituting 5-chloro-6-(trifluoromethyl)pyridin-3-ol for 5-(trifluoromethyl)pyridin-3-ol gave the titled compound. ¹H NMR (400 MHz, DMSO-d₆) δ ppm 8.90 (s, 1H), 8.46 (d, J=2.5 Hz, 1H), 8.03 (d, J=2.5 Hz, 1H), 7.47 (t, J=8.9 Hz, 1H), 7.05 (dd, J=11.3, 2.8 Hz, 1H), 6.83 (ddd, J=8.9, 2.9, 1.2 Hz, 1H), 5.50 (s, 2H), 4.48 (s, 2H), 2.51 (s, 6H); MS (ESI⁺) m/z 547.1 (M+H)⁺.

Example 64 2-(4-chloro-3-fluorophenoxy)-N-[3-(3-{[(6-cyclopropylpyridin-3-yl)oxy]methyl}-1,2,4-oxadiazol-5-yl)bicyclo[1.1.1]pentan-1-yl]acetamide (Compound 163)

The reaction described in Example 60F substituting 6-cyclopropylpyridin-3-ol for 5-(trifluoromethyl)pyridin-3-ol gave the titled compound. ¹H NMR (400 MHz, DMSO-d₆) δ ppm 8.90 (s, 1H), 8.23 (d, J=3.0 Hz, 1H), 7.55-7.42 (m, 2H), 7.27 (d, J=8.7 Hz, 1H), 7.05 (dd, J=11.3, 2.9 Hz, 1H), 6.83 (ddd, J=8.9, 2.8, 1.2 Hz, 1H), 5.30 (s, 2H), 4.48 (s, 2H), 2.50 (s, 6H), 2.06 (tt, J=8.2, 4.9 Hz, 1H), 0.95-0.81 (m, 4H); MS (APCI⁺) m/z 485.2 (M+H)⁺.

Example 65 2-(4-chloro-3-fluorophenoxy)-N-{4-[5-(methoxymethyl)-1,3,4-oxadiazol-2-yl]-3-oxobicyclo[2.2.2]octan-1-yl}acetamide (Compound 164)

Example 65A: ethyl 1,4-dioxaspiro[4.5]decane-8-carboxylate

A mixture of ethyl 4-oxocyclohexanecarboxylate (11.70 mL, 73.4 mmol), ethane-1,2-diol (12.29 mL, 220 mmol), and p-toluenesulfonic acid monohydrate (1.397 g, 7.34 mmol) in toluene (200 mL) was stirred at 120° C. with a Dean-Stark trap apparatus for 180 minutes. The reaction mixture was neutralized with N-ethyl-N-isopropylpropan-2-amine and then concentrated. The residue was purified on silica gel (0-30% ethyl acetate in heptane) to give 12.77 g of the title compound as a clear oil. ¹H NMR (400 MHz, DMSO-d₆) δ ppm 4.01 (q, J=7.1 Hz, 2H), 3.81 (s, 4H), 2.32 (tt, J=10.4, 3.8 Hz, 1H), 1.83-1.71 (m, 2H), 1.66-1.57 (m, 1H), 1.62-1.38 (m, 5H), 1.13 (t, J=7.1 Hz, 3H).

Example 65B: ethyl 8-acetyl-1,4-dioxaspiro[4.5]decane-8-carboxylate

To a solution of diisopropylamine (5.19 mL, 36.4 mmol) in tetrahydrofuran (25 mL) at 0° C. was added n-butyllithium slowly below 5° C. After stirring for 30 minutes, the solution was cooled to −78° C. under nitrogen, and a solution of Example 65A (6.0 g, 28.0 mmol) in tetrahydrofuran (3 mL) was added slowly, and the resultant mixture was stirred for 30 minutes at the same temperature. Then acetyl chloride (2.59 mL, 36.4 mmol) was added slowly to maintain the temperature below −60° C., and the mixture was stirred at −70° C. for 2 hours. The reaction was quenched with saturated NH₄Cl solution, and the aqueous phase was extracted with ethyl acetate. The organic layer was washed with brine, dried over magnesium sulfate and filtered. The filtrate was concentrated, and the residue was purified on silica gel (0-70% ethyl acetate in heptane) to give 6.78 g of the title compound as a clear oil. ¹H NMR (500 MHz, DMSO-d₆) δ ppm 4.19-4.11 (m, 2H), 3.85 (s, 4H), 2.13 (s, 3H), 2.10-2.01 (m, 2H), 1.90 (ddd, J=13.9, 9.6, 4.6 Hz, 2H), 1.54 (th, J=13.6, 4.7 Hz, 4H), 1.18 (dd, J=7.6, 6.5 Hz, 3H).

Example 65C: ethyl 1-acetyl-4-oxocyclohexane-1-carboxylate

A mixture of Example 65B (6.5 g, 25.4 mmol) and HCl (21.13 mL, 127 mmol) in acetone (60 mL) was stirred at ambient temperature overnight. Volatiles were removed under reduced pressure, and the residue was partitioned between water and dichloromethane. The organic layer was washed with brine, dried over magnesium sulfate and filtered. The filtrate was concentrated to give 5.46 g of the title compound as a clear oil, used without further purification. ¹H NMR (400 MHz, DMSO-d₆) δ ppm 4.16 (q, J=7.1 Hz, 2H), 2.17 (s, 3H), 2.35-2.07 (m, 8H), 1.17 (t, J=7.1 Hz, 3H).

Example 65D: ethyl 4-(benzylamino)-2-oxobicyclo[2.2.2]octane-1-carboxylate

A mixture of Example 65C (9.7 g, 45.7 mmol), benzylamine (14.98 mL, 137 mmol), and p-toluenesulfonic acid monohydrate (0.087 g, 0.457 mmol) in toluene (100 mL) was stirred at 130° C. with Dean-Stark trap apparatus overnight. The mixture was concentrated, and the residue was stirred with a mixture of ethyl acetate (50 mL) and 3 N HCl (100 mL) for 30 minutes. The precipitate was collected by filtration, washed with mixture of ethyl acetate/heptane, and air-dried to give 11.3 g of title compound as a HCl salt. The filtrate was neutralized with 6 N NaOH and extracted with ethyl acetate (100 mL×2). The organic layer was washed with brine, dried over magnesium sulfate and filtered. The residue was purified on silica gel (0-70% ethyl acetate in heptane) to give another 0.77 g of the title compound as yellow solid. ¹H NMR (400 MHz, DMSO-d₆) δ ppm 9.73 (t, J=6.2 Hz, 2H), 7.87-7.12 (m, 5H), 4.09 (m, 4H), 2.88 (s, 2H), 2.08 (dt, J=20.7, 13.4 Hz, 6H), 1.16 (t, J=7.1 Hz, 3H); MS (ESI⁺) m/z 302.1 (M+H)⁺.

Example 65E: ethyl 4-amino-2-oxobicyclo[2.2.2]octane-1-carboxylate, hydrochloric acid To a mixture of Example 65D (11.2 g, 33.2 mmol) in tetrahydrofuran (110 mL) in a 50 mL pressure bottle was added 20% Pd(OH)$_2$/C, wet (2.2 g, 1.598 mmol), and the reaction was shaken at 50° C. under 50 psi of hydrogen for 22 hours. The reaction mixture was cooled to ambient temperature, solids were removed by filtration and washed with methanol (1 L). The filtrate and wash were concentrated to give 7.9 g of the title compound as a light yellow solid. $^1$H NMR (400 MHz, DMSO-d$_6$) δ ppm 8.46 (s, 3H), 4.07 (q, J=7.1 Hz, 2H), 2.62 (s, 2H), 2.17-2.05 (m, 2H), 2.04-1.78 (m, 6H), 1.14 (t, J=7.1 Hz, 3H).

Example 65F: ethyl 4-[2-(4-chloro-3-fluorophenoxy)acetamido]-2-oxobicyclo[2.2.2]octane-1-carboxylate To a suspension of Example 65E (7.8 g, 31.5 mmol), N-ethyl-N-isopropylpropan-2-amine (22.00 mL, 126 mmol) and 2-(4-chloro-3-fluorophenoxy)acetic acid (7.41 g, 36.2 mmol) in N,N-dimethylformamide (200 mL), 2-(3H-[1,2,3]triazolo[4,5-b]pyridin-3-yl)-1,1,3,3-tetramethylisouronium hexafluorophosphate(V) (14.97 g, 39.4 mmol) was added, and the resulting brown solution was stirred at ambient temperature for 16 hours. Water was added, and the mixture was stirred for 15 minutes. The precipitate was collected by filtration, washed with water, and air-dried to give 12.1 g of the title compound as an off-white solid. $^1$H NMR (400 MHz, DMSO-d$_6$) δ ppm 7.87 (s, 1H), 7.45 (t, J=8.9 Hz, 1H), 7.00 (dd, J=11.4, 2.9 Hz, 1H), 6.79 (ddd, J=8.9, 2.9, 1.2 Hz, 1H), 4.45 (s, 2H), 4.06 (q, J=7.1 Hz, 2H), 2.73 (s, 2H), 2.07 (m, 1H), 2.01-1.84 (m, 6H), 1.14 (t, J=7.1 Hz, 3H); MS (ESI$^+$) m/z 398.0 (M+H)$^+$.

Example 65G: 4-[2-(4-chloro-3-fluorophenoxy)acetamido]-2-oxobicyclo[2.2.2]octane-1-carboxylic acid A suspension of Example 65F (11.37 g, 28.6 mmol) and sodium hydroxide (7.15 mL, 57.2 mmol, 8 M solution) in methanol (100 mL) was stirred at ambient temperature for 16 hours. Volatiles were removed, and the residue was acidified with 1 N HCl. The precipitate was collected by filtration and dried in vacuum oven to give 9.9 g of the title compound as a white solid. $^1$H NMR (400 MHz, DMSO-d$_6$) δ ppm 12.49 (s, 1H), 7.86 (s, 1H), 7.45 (t, J=8.9 Hz, 1H), 7.00 (dd, J=11.4, 2.9 Hz, 1H), 6.83-6.74 (m, 1H), 4.45 (s, 2H), 2.71 (s, 2H), 2.01-1.81 (m, 7H); MS (ESI$^-$) m/z 368.1 (M-H)$^-$.

Example 65H: 2-(4-chloro-3-fluorophenoxy)-N-{4-[2-(methoxyacetyl)hydrazinecarbonyl]-3-oxobicyclo[2.2.2]octan-1-yl}acetamide To a mixture of Example 65G (0.25 g, 0.676 mmol), 2-methoxyacetohydrazide (0.077 g, 0.744 mmol), and N-ethyl-N-isopropylpropan-2-amine (0.236 mL, 1.352 mmol) in N,N-dimethylformamide (5.0 mL), 2-(3H-[1,2,3]triazolo[4,5-b]pyridin-3-yl)-1,1,3,3-tetramethylisouronium hexafluorophosphate(V) (0.283 g, 0.744 mmol) was added, and the yellow solution was stirred at ambient temperature overnight. The reaction mixture was partitioned between water and ethyl acetate. The organic layer was dried over magnesium sulfate and filtered. The filtrate was concentrated, and the residue was purified on silica gel (0-10% methanol/dichloromethane) to give 0.25 g of the title compound as a white solid. $^1$H NMR (400 MHz, DMSO-d$_6$) δ ppm 9.76 (d, J=1.7 Hz, 1H), 9.44 (d, J=1.7 Hz, 1H), 7.88 (s, 1H), 7.45 (t, J=8.9 Hz, 1H), 7.01 (dd, J=11.4, 2.9 Hz, 1H), 6.79 (ddd, J=8.9, 2.8, 1.2 Hz, 1H), 4.46 (s, 2H), 3.84 (s, 2H), 3.27 (s, 3H), 2.71 (s, 2H), 1.84-2.12 (m, 6H).

Example 651: 2-(4-chloro-3-fluorophenoxy)-N-{4-[5-(methoxymethyl)-1,3,4-oxadiazol-2-yl]-3-oxobicyclo[2.2.2]octan-1-yl}acetamide To a mixture of Example 65H (0.24 g, 0.526 mmol) and N-ethyl-N-isopropylpropan-2-amine (0.276 mL, 1.579 mmol) in acetonitrile (5.0 mL), 4-methylbenzene-1-sulfonyl chloride (0.201 g, 1.053 mmol) was added at 0° C., and the suspension was heated at 50° C. overnight.

Volatiles were removed, and the residue was purified by HPLC (performed on Phenomenex® Luna® C18(2) 5 μm 100 Å AXIA™ column (250 mm×21.2 mm). A gradient of acetonitrile (A) and 0.1% trifluoroacetic acid in water (B) is used, at a flow rate of 25 mL/minute. A linear gradient was used from about 10% of A to about 95% of A over about 10 minutes. Detection method was UV at a wavelength of 218 nM and 254 nM) to give 135 mg of the title compound as a light yellow solid. $^1$H NMR (400 MHz, DMSO-d$_6$) δ ppm 7.98 (s, 1H), 7.44 (t, J=8.9 Hz, 1H), 6.99 (dd, J=11.4, 2.9 Hz, 1H), 6.79 (ddd, J=9.0, 2.9, 1.2 Hz, 1H), 4.59 (s, 2H), 4.46 (s, 2H), 3.28 (s, 3H), 2.85 (t, J=1.3 Hz, 2H), 2.28 (ddd, J=15.0, 8.2, 3.9 Hz, 2H), 2.21-1.94 (m, 6H); MS (ESI$^+$) m/z 438.1 (M+H)$^+$.

Example 66 2-(4-chloro-3-fluorophenoxy)-N-{3-hydroxy-4-[5-(methoxymethyl)-1,3,4-oxadiazol-2-yl]bicyclo[2.2.2]octan-1-yl}acetamide (Compound 165)

A mixture of Example 65 (0.1 g, 0.228 mmol) and sodium borohydride (0.043 g, 1.142 mmol) in a mixture of methanol/dichloromethane (1:1, 3 mL) was stirred at ambient temperature for 16 hours. Volatiles were removed, and the residue was purified by HPLC (20-95% acetonitrile in 0.1% trifluoroacetic acid/water at flow rate of 25 mL/minute on a Phenomenex® C18 5 μm, 250 mm×21.2 mm, column) to give 78 mg of the title compound as a solid. $^1$H NMR (400 MHz, DMSO-d$_6$) δ ppm 7.57 (s, 1H), 7.45 (t, J=8.9 Hz, 1H), 7.00 (dd, J=11.4, 2.9 Hz, 1H), 6.78 (ddd, J=8.9, 2.9, 1.2 Hz, 1H), 4.55 (s, 2H), 4.43 (s, 2H), 4.06 (dd, J=9.6, 3.2 Hz, 1H), 3.29 (s, 3H), 2.34 (ddd, J=7.5, 5.5, 2.2 Hz, 1H), 1.98-1.68 (m, 9H); MS (ESI$^+$) m/z 440.0 (M+H)$^+$.

Example 67 2-(4-chloro-3-fluorophenoxy)-N-{3-hydroxy-4-[3-({[6-(trifluoromethyl)pyridin-3-yl]oxy}methyl)-1,2,4-oxadiazol-5-yl]bicyclo[2.2.2]octan-1-yl}acetamide (Compound 166)

Example 67A: 2-(4-chloro-3-fluorophenoxy)-N-(4-(((2-chloroacetimidamido)oxy)carbonyl)-3-oxobicyclo[2.2.2]octan-1-yl)acetamide To a solution of the product of Example 65G (1.40 g, 3.79 mmol), 1-hydroxybenzotriazole hydrate (HOBT, 0.232 g, 1.51 mmol), triethylamine (1.58 mL, 11.4 mmol), and 2-(1H-benzo[d][1,2,3]triazol-1-yl)-1,1,3,3-tetramethyluronium tetrafluoroborate (TBTU, 1.46 g, 4.54 mmol) in dimethylformamide (30 mL) was added Example 60A (0.411 g, 3.79 mmol) at 0° C. The reaction mixture was allowed to warm to ambient temperature and was stirred for 16 hours. The reaction was quenched with brine and extracted with ethyl acetate (2×). The combined organic layers were washed with water (2×), dried over anhydrous MgSO$_4$, concentrated under reduced pressure, and purified on an 80 g silica gel column using the Biotage® Isolera™ One flash system eluting with ethyl acetate/heptanes (80-100%) to provide the title compound (1.04 g, 60% yield). MS (ESI$^+$) m/z 460.1 (M+H)$^+$.

Example 67B: 2-(4-chloro-3-fluorophenoxy)-N-(4-(3-(chloromethyl)-1,2,4-oxadiazol-5-yl)-3-oxobicyclo[2.2.2]octan-1-yl)acetamide A mixture of the product of Example 67A (0.345 g, 0.750 mmol) in acetic acid (8 mL) was heated at 115° C. for 3 hours. The reaction mixture was concentrated under reduced pressure. The residue was treated with saturated aqueous NaHCO$_3$ and extracted with ethyl acetate (2×). The combined organic layers were dried over anhydrous MgSO$_4$, filtered, concentrated under reduced pressure until most of the solvent was removed. The suspension was cooled and filtered, and the solids were washed with heptanes/ethyl acetate (1:1). The filtrate was subjected to the above trituration process two more times to provide the title compound (0.191 g, 58% yield). MS (ESI$^+$) m/z 442.0 (M+H)$^+$.

Example 67C: 2-(4-chloro-3-fluorophenoxy)-N-(4-(3-(chloromethyl)-1,2,4-oxadiazol-5-yl)-3-hydroxybicyclo[2.2.2]octan-1-yl)acetamide To a solution of the product of Example 67B (170 mg, 0.384 mmol) in CH$_2$Cl$_2$ (3.5 mL) and methanol (3.5 mL) was added sodium borohydride (18.9 mg, 0.500 mmol). The reaction mixture was stirred for 1.5 hours. The solution was treated with brine and saturated aqueous NaHCO$_3$ and extracted with CH$_2$Cl$_2$. The organic layer was concentrated under reduced pressure, and the residue was purified on a 12 g silica gel column using the Biotage® Isolera™ One flash system eluting with heptanes/ethyl acetate (3:7 to 2:8) to provide the title compound (0.118 g, 69% yield). MS (ESI$^+$) m/z 444.0 (M+H)$^+$.

Example 67D: 2-(4-chloro-3-fluorophenoxy)-N-{3-hydroxy-4-[3-({[6-(trifluoromethyl)pyridin-3-yl]oxy}methyl)-1,2,4-oxadiazol-5-yl]bicyclo[2.2.2]octan-1-yl}acetamide A mixture of the product of Example 67C (13.0 mg, 0.029 mmol), 6-(trifluoromethyl)pyridin-3-ol (7.16 mg, 0.044 mmol), potassium iodide (0.243 mg, 1.463 μmol), and potassium carbonate (8.09 mg, 0.059 mmol) in acetone (2.5 mL) was heated at 140° C. in a Biotage® Initiator microwave reactor for 30 minutes. The reaction mixture was concentrated under reduced pressure, and the residue was purified by reverse-phase HPLC (see protocol in Example 60F) to provide the title compound (9.3 mg, 56% yield). $^1$H NMR (400 MHz, methanol-d$_4$) δ ppm 8.44 (d, J=2.8 Hz, 1H), 7.75 (d, J=8.7 Hz, 1H), 7.66 (dd, J=8.8, 2.8 Hz, 1H), 7.35 (t, J=8.7 Hz, 1H), 6.89 (dd, J=11.0, 2.8 Hz, 1H), 6.78 (ddd, J=9.0, 2.9, 1.3 Hz, 1H), 5.36 (s, 2H), 4.42 (s, 2H), 4.34 (ddd, J=9.5, 3.2, 1.4 Hz, 1H), 2.64-2.46 (m, 2H), 2.15-1.81 (m, 8H); MS (ESI$^+$) m/z 571.2 (M+H)$^+$.

Example 68 2-(4-chloro-3-fluorophenoxy)-N-{3-hydroxy-4-[3-({[2-(trifluoromethyl)pyridin-4-yl]oxy}methyl)-1,2,4-oxadiazol-5-yl]bicyclo[2.2.2]octan-1-yl}acetamide (Compound 167)

The reaction described in Example 67D substituting 2-(trifluoromethyl)pyridin-4-ol for 6-(trifluoromethyl)pyridin-3-ol gave the title compound. $^1$H NMR (501 MHz, DMSO-d$_6$) δ ppm 8.60 (d, J=5.7 Hz, 1H), 7.68-7.55 (m, 2H), 7.46 (t, J=8.9 Hz, 1H), 7.37 (dd, J=5.7, 2.5 Hz, 1H), 7.01 (dd, J=11.4, 2.8 Hz, 1H), 6.80 (ddd, J=9.0, 2.9, 1.2 Hz, 1H), 5.48 (s, 2H), 4.45 (s, 2H), 4.16 (ddd, J=9.4, 3.2, 1.3 Hz, 1H), 2.45-2.28 (m, 2H), 2.01-1.69 (m, 8H); MS (ESI$^+$) m/z 571.1 (M+H)$^+$.

Example 69 2-(4-chloro-3-fluorophenoxy)-N-(3-{4-[(4-chloro-3-fluorophenoxy)methyl]-1H-imidazol-2-yl}bicyclo[1.1.1]pentan-1-yl)acetamide (Compound 168)

Example 69A: 3-(2-(4-chloro-3-fluorophenoxy)acetamido)bicyclo[1.1.1]pentane-1-carboxamide To a solution of the product of Example 60B (9.0 g, 26.1 mmol) in methanol (200 mL) was added ammonium hydroxide solution (100 mL, 770 mmol) at 20° C. under N$_2$. The mixture was stirred at 20° C. for 12 hours and concentrated under reduced pressure. The residue was treated with methyl tert-butyl ether (30 mL) and filtered. The filter cake was dried under high vacuum to provide the title compound (7.0 g, 82% yield). $^1$H NMR (400 MHz, DMSO-d$_6$) δ ppm 2.15 (s, 6H), 4.46 (s, 2H), 6.85 (d, 1H), 6.98 (br. s., 1H), 7.03-7.13 (m, 1H), 7.29 (br. s., 1H), 7.50 (t, 1H), 8.72 (s, 1H).

Example 69B: 2-(4-chloro-3-fluorophenoxy)-N-(3-cyanobicyclo[1.1.1]pentan-1-yl)acetamide To a solution of the product of Example 69A (7.0 g, 21.3 mmol) in tetrahydrofuran (200 mL) was added Burgess reagent (10.1 g, 42.5 mmol) at 0° C., and the resulting mixture was stirred for 12 hours at 20° C. The mixture was concentrated under reduced pressure, and the residue was purified by column chromatography on silica gel (dichloromethane:methanol=50:1) to give the crude title compound. The crude title compound was treated with water (150 mL) and the solids were collected by filtration. The collected solids were dried under high vacuum to provide the title compound (6.0 g, 92% yield). $^1$H NMR (400 MHz, CDCl$_3$) δ ppm 2.64 (s, 6H), 4.40 (s, 2H), 6.67 (dd, 1H), 6.75 (dd, 1H), 6.89 (br. s., 1H), 7.34 (t, 1H).

Example 69C: N-(3-carbamimidoylbicyclo[1.1.1]pentan-1-yl)-2-(4-chloro-3-fluorophenoxy)acetamide A mixture of acetyl chloride (8.44 mL, 119 mmol) in ethanol (20 mL) and chloroform (15 mL) was stirred for 30 minutes at 0° C. A solution of the product of Example 69B (1.00 g, 3.39 mmol) in chloroform (50 mL) was added to the above mixture, and the reaction was warmed to ambient temperature and was stirred for 24 hours. The reaction mixture was concentrated under reduced pressure, and the residue was dissolved in ethanol (25 mL) and treated with 7 N ammonia in methanol (19.39 mL, 136 mmol). The mixture in a capped flask was stirred for 7 hours and then was concentrated under reduced pressure. The concentrate was treated with brine, saturated aqueous NaHCO$_3$ and ethyl acetate. The suspension in the organic layer was collected by filtration, washed with ethyl acetate and water, and vacuum oven-dried to provide the title compound (0.60 g, 57% yield). MS (APCI$^+$) m/z 312.2 (M+H)$^+$.

Example 69D: 2-(4-chloro-3-fluorophenoxy)-N-(3-(4-(hydroxymethyl)-1H-imidazol-2-yl)bicyclo[1.1.1]pentan-1-yl)acetamide A mixture of the product of Example 69C (0.590 g, 1.89 mmol), 1,3-dihydroxyacetone dimer (0.511 g, 2.84 mmol), and ammonium chloride (0.405 g, 7.57 mmol) in aqueous ammonium hydroxide (10 mL, 257 mmol) was heated at 100° C. in a capped vial for 45 minutes. After cooling to ambient temperature, water was added to the mixture. The suspension was stirred for 15 minutes, and the solids were collected by filtration and washed with water. The resulting solids were vacuum oven-dried. The solids contained mostly the titled compound. The solids were suspended in ethyl acetate (10 mL) and stirred at 60° C. for 1 hour. After cooling, the solids were collected by filtration, washed with ethyl acetate, and vacuum oven-dried to provide 0.120 g of the title compound. The filtrate was concentrated, and the residue was purified on a 25 g column using the Biotage® Isolera™ One flash system eluting with methanol/ethyl acetate (1:9) to provide an additional 0.189 g of the title compound (0.309 g, 45% yield). MS (ESI$^+$) m/z 366.1 (M+H)$^+$.

Example 69E: 2-(4-chloro-3-fluorophenoxy)-N-(3-{4-[(4-chloro-3-fluorophenoxy)methyl]-1H-imidazol-2-yl}bicyclo[1.1.1]pentan-1-yl)acetamide A mixture of the product of Example 69D (80.0 mg, 0.219 mmol), 4-chloro-3-fluorophenol (80 mg, 0.547 mmol), di-isopropyl azodicarboxylate (DIAD, 155 mg, 0.765 mmol), and triphenylphosphine on solid support (255 mg, 3 mmol/g, 0.972 mmol) in tetrahydrofuran (7 mL) was stirred for 2 days. The reaction mixture was filtered through diatomaceous earth and washed with ethyl acetate and methanol. The filtrate was concentrated under reduced pressure, and the residue was purified by reverse-phase HPLC (see protocol in Example 60F). The desired fractions were concentrated under reduced pressure and further purified on a 12 g silica gel column using the Biotage® Isolera™ One flash system eluting with ethyl acetate to methanol/ethyl acetate (5:95) to provide the title compound (23.2 mg, 21% yield). $^1$H NMR (400 MHz, DMSO-d$_6$) δ ppm 12.23 (s, 0.25H), 11.97 (s, 0.75H), 8.78 (s, 1H), 7.52-7.43 (m, 2H), 7.26-7.00 (m, 2.85H), 6.89-6.85 (m, 2.15H), 5.00 (s, 0.15H), 4.88 (s, 1.85H), 4.49 (s, 2H), 2.32 (s, 6H); MS (ESI$^+$) m/z 494.1 (M+H)$^+$.

Example 70 2-(4-chloro-3-fluorophenoxy)-N-{3-[4-({[6-(trifluoromethyl)pyridin-3-yl]oxy}methyl)-1H-imidazol-2-yl]bicyclo[1.1.1]pentan-1-yl}acetamide (Compound 169)

A mixture of the product of Example 69D (40.0 mg, 0.109 mmol), 6-(trifluoromethyl)pyridin-3-ol (44.6 mg, 0.273 mmol), di-isopropyl azodicarboxylate (DIAD, 77 mg, 0.383 mmol), and triphenylphosphine on solid support (128 mg, 3 mmol/g, 0.488 mmol) in tetrahydrofuran (3.5 mL) was stirred for 2 days. The reaction mixture was filtered through diatomaceous earth and washed with ethyl acetate and methanol. The filtrate was concentrated under reduced pressure, and purified on a 12 g silica gel column using the Biotage® Isolera™ One flash system eluting with ethyl acetate to methanol/ethyl acetate (5:95) to provide the title compound (2.7 mg, 5% yield). $^1$H NMR (400 MHz, DMSO-d$_6$) δ ppm 12.20 (s, 0.2H), 12.01 (s, 0.8H), 8.78 (s, 1H), 8.48 (d, J=2.7 Hz, 1H), 7.83 (d, J=8.7 Hz, 1H), 7.71 (dd, J=8.8, 2.8 Hz, 1H), 7.50 (t, J=8.9 Hz, 1H), 7.21 (s, 1H), 7.09 (dd, J=11.3, 2.8 Hz, 1H), 6.87 (dd, J=9.1, 2.8 Hz, 1H), 5.06 (s, 2H), 4.49 (s, 2H), 2.33 (s, 6H); MS (ESI$^+$) m/z 511.1 (M+H)$^+$.

Example 71 2-(4-chloro-3-fluorophenoxy)-N-{4-[5-(4-chloro-3-fluorophenoxy)-1,3,4-oxadiazol-2-yl]-3-hydroxybicyclo[2.2.2]octan-1-yl}acetamide (Compound 170)

Example 71A: ethyl 4-[2-(4-chloro-3-fluorophenoxy)acetamido]-2-hydroxybicyclo[2.2.2]octane-1-carboxylate To a solution of Example 65F (7.51 g, 18.87 mmol) in ethanol (800 mL) was added NaBH$_4$ (0.5 g, 13.21 mmol) at 0° C., and the solution was stirred at 0° C. for 3 hours. The reaction mixture was poured into saturated ammonium chloride solution (500 mL), and the precipitate was collected by filtration and dried under high vacuum to give the title compound (6.5 g, yield 73.2%) as a white solid. $^1$H NMR (400 MHz, DMSO-d$_6$) δ ppm 7.55 (s, 1H), 7.48 (t, J=8.77 Hz, 1H), 7.13 (s, 1H), 7.02 (dd, J=11.62, 2.85 Hz, 1H), 6.80 (br d, J=9.21 Hz, 1H), 4.89 (d, J=4.82 Hz, 1H), 4.44 (s, 2H), 3.81-4.16 (m, 3H), 1.46-2.32 (m, 10H), 1.14 (t, J=7.02 Hz, 3H).

Example 71B: 2-(4-chloro-3-fluorophenoxy)-N-[4-(hydrazinecarbonyl)-3-hydroxybicyclo[2.2.2]octan-1-yl]acetamide A solution of Example 71A (4 g, 8.50 mmol) in hydrazine hydrate (100 mL, 1999 mmol) was stirred for 3 hours at 50° C. The solution was cooled to ambient temperature, and the resulting precipitate was collected by filtration and dried under high vacuum to give the title compound (3.5 g, yield 91%) as a white solid. $^1$H NMR (400 MHz, DMSO-d$_6$) δ ppm 8.65 (br s, 1H), 7.61-7.36 (m, 2H), 7.03 (dd, J=11.43, 2.51 Hz, 1H), 6.81 (br d, J=8.80 Hz, 1H), 4.44 (s, 2H), 4.03 (br d, J=8.44 Hz, 1H), 4.09-3.93 (m, 1H), 2.21 (br t, J=10.15 Hz, 1H), 2.11-1.97 (m, 1H), 1.92-1.79 (m, 1H), 1.79-1.45 (m, 8H).

Example 71C: 2-(4-chloro-3-fluorophenoxy)-N-[3-hydroxy-4-(5-sulfanyl-1,3,4-oxadiazol-2-yl)bicyclo[2.2.2]octan-1-yl]acetamide To a solution of Example 71B (5 g, 12.31 mmol) in methanol (200 mL) was added KOH (1.036 g, 18.47 mmol) and CS$_2$ (1.484 mL, 24.62 mmol) sequentially at ambient temperature. Then the resulting mixture was stirred for 12 hours at 80° C. The mixture was concentrated under reduced pressure, and the residue was diluted with water (200 mL). The mixture was acidified to pH=1 with aqueous HCl (1 N) solution, and the precipitate was collected by filtration and dried under high vacuum to give the title compound (4.5 g, yield 77%) as a white solid which was used in the next step without further purification. $^1$H NMR 400 MHz, DMSO-d$_6$) δ ppm 14.27 (br s, 1H), 7.62 (s, 1H), 7.47 (t, J=8.99 Hz, 1H), 7.01 (dd, J=11.62, 2.41 Hz, 1H), 6.85-6.74 (m, 1H), 5.14 (d, J=4.82 Hz, 1H), 4.44 (s, 2H), 4.07-3.94 (m, 1H), 2.48 (s, 1H), 2.36-2.15 (m, 2H), 1.97-1.62 (m, 8H).

Example 71D: 2-(4-chloro-3-fluorophenoxy)-N-[3-hydroxy-4-[5-(methylsulfanyl)-1,3,4-oxadiazol-2-yl]bicyclo[2.2.2]octan-1-yl]acetamide To a solution of Example 71C (5.5 g, 11.83 mmol) in N,N-dimethyl formamide (100 mL) was added potassium carbonate (3.27 g, 23.65 mmol) and iodomethane (1.104 mL, 17.74 mmol) sequentially at ambient temperature, and the mixture was stirred for 12 hours at the same temperature.

The reaction mixture was poured into water (500 mL), and the precipitate was collected by filtration and dried under high vacuum to give the title compound (4.8 g, yield 87%) as a white solid. $^1$H NMR (400 MHz, DMSO-d$_6$) δ ppm 7.65 (s, 1H), 7.49 (br t, J=8.77 Hz, 1H), 7.03 (br d, J=10.96 Hz, 1H), 6.81 (br d, J=8.77 Hz, 1H), 5.06 (br d, J=4.82 Hz, 1H), 4.46 (s, 2H), 4.06 (br s, 1H), 2.66 (s, 3H), 2.25-2.40 (m, 2H), 2.02-1.66 (m, 8H).

Example 71E: 2-(4-chloro-3-fluorophenoxy)-N-[3-hydroxy-4-[5-(methanesulfonyl)-1,3,4-oxadiazol-2-yl]bicyclo[2.2.2]octan-1-yl]acetamide To a solution of Example 71D (0.2 g, 0.416 mmol) in water (5 mL) and acetic acid (10 mL) was added KMnO$_4$ (0.079 g, 0.500 mmol) at 0° C., and the mixture was stirred for 2 hours at 0° C. Then sodium sulfite was added until the color of the reaction mixture turned to colorless from purple. Then the mixture was concentrated under reduced pressure, and the residue was diluted with water (20 mL) and extracted with ethyl acetate (3×30 mL). The combined organic layer was washed with brine (50 mL), dried over Na$_2$SO$_4$ and concentrated under reduced pressure. The residue was purified by preparative HPLC ((25-100% acetonitrile in 0.075% trifluoroacetic acid/water at 25 mL/minute on a Phenomenex® Luna® C18 5 μm column (100 mm×30 mm)) to give the title compound (72 mg, yield 36.5%) as a white solid. $^1$H NMR (400 MHz, DMSO-d$_6$) δ ppm 7.67 (s, 1H) 7.49 (t, J=8.99 Hz, 1H), 7.04 (dd, J=11.40, 2.63 Hz, 1H), 6.82 (dd, J=8.77, 1.75 Hz, 1H), 5.14 (d, J=4.82 Hz, 1H), 4.47 (s, 2H), 4.19-4.07 (m, 1H), 3.63 (s, 3H), 2.45-2.26 (m, 2H), 2.04-1.72 (m, 8H); MS (ESI+) m/z 474.0 (M+H)$^+$.

Example 71F: 2-(4-chloro-3-fluorophenoxy)-N-[4-[5-(4-chloro-3-fluorophenoxy)-1,3,4-oxadiazol-2-yl]-3-hydroxybicyclo[2.2.2]octan-1-yl]acetamide To a solution of 4-chloro-3-fluorophenol (14.07 mg, 0.096 mmol) in N,N-dimethyl formamide (1.0 mL), potassium carbonate (25.5 mg, 0.185 mmol) was added, followed by Example 71E (35 mg, 0.074 mmol) at ambient temperature. The reaction mixture was left stirring at 40° C. for 16 hours. Solvent was removed under high vacuum and the residue was purified by HPLC (30-100% acetonitrile in 0.1% trifluoroacetic acid/water on Phenomenex® C18 10 μm (250 mm×50 mm) column at a flow rate of 50 mL/minute) to give 15 mg of the title compound as a light yellow solid. $^1$H NMR (400 MHz, DMSO-d$_6$) δ ppm 7.80-7.70 (m, 2H), 7.61 (s, 1H), 7.54-7.39 (m, 2H), 7.03 (dd, J=11.4, 2.8 Hz, 1H), 6.82 (ddd, J=9.0, 2.9, 1.2 Hz, 1H), 5.03 (d, J=4.7 Hz, 1H), 4.46 (s, 2H), 4.11-4.02 (m, 1H), 2.32 (qd, J=11.5, 10.3, 2.7 Hz, 2H), 1.99-1.71 (m, 8H); MS (ESI+) m/z 540.1 (M+H)$^+$.

Example 72: Activity of Exemplary Compounds in an In Vitro Model of Vanishing Cell White Matter Disease (VWMD)

In order to test exemplary compounds of the invention in a cellular context, a stable VWMD cell line was first constructed. The ATF4 reporter was prepared by fusing the human full-length ATF4 5'-UTR (NCBI Accession No. BC022088.2) in front of the firefly luciferase (FLuc) coding sequence lacking the initiator methionine as described in Sidrauski et al (eLife 2013). The construct was used to produce recombinant retroviruses using standard methods and the resulting viral supernatant was used to transduce HEK293T cells, which were then subsequently selected with puromycin to generate a stable cell line.

HEK293T cells carrying the ATF4 luciferase reporter were plated on polylysine coated 384-well plates (Greiner Bio-one) at 30,000 cells per well. Cells were treated the next day with 1 μg/mL tunicamycin and 200 nM of a compound of Formula (I) for 7 hours. Luminescence was measured using One Glo (Promega) as specified by the manufacturer. Cells were maintained in DMEM with L-glutamine supplemented with 10% heat-inactivated FBS (Gibco) and Antibiotic-Antimycotic solution (Gibco).

Table 2 below summarizes the EC$_{50}$ data obtained using the ATF4-Luc assay for exemplary compounds of the invention. In this table, "A" represents an EC$_{50}$ of less than 50 nM; "B" an EC$_{50}$ of between 50 nM and 250 nM; "C" an EC$_{50}$ of between 250 nM and 1 μM; "D" an EC$_{50}$ of between 1 μM and 2 μM; and "E" an EC$_{50}$ of greater than 2 μM.

TABLE 2

EC$_{50}$ values of exemplary compounds of the invention in the ATF4-Luc assay.

| Compound No. | ATF4-Luc EC$_{50}$ |
| --- | --- |
| 100 | B |
| 101 | A |
| 102 | D |
| 103 | B |
| 104 | C |
| 105 | A |
| 106 | C |
| 107 | C |
| 108 | C |
| 109 | A |
| 110 | B |
| 111 | B |
| 112 | E |
| 113 | A |
| 114 | C |
| 115 | A |
| 116 | B |
| 117 | B |
| 118 | C |
| 119 | C |
| 120 | B |
| 121 | B |
| 122 | B |
| 123 | B |
| 124 | E |
| 125 | C |
| 126 | A |
| 127 | C |
| 128 | A |
| 129 | B |
| 130 | B |
| 131 | A |
| 132 | A |
| 133 | A |
| 134 | C |
| 135 | B |
| 136 | B |
| 137 | C |
| 138 | B |
| 139 | A |
| 140 | B |
| 141 | B |
| 142 | A |
| 143 | C |
| 144 | E |
| 145 | B |
| 146 | C |
| 147 | D |
| 148 | B |
| 149 | D |
| 150 | D |

TABLE 2-continued

EC$_{50}$ values of exemplary compounds
of the invention in the ATF4-Luc assay.

| Compound No. | ATF4-Luc EC$_{50}$ |
|---|---|
| 151 | D |
| 152 | D |
| 153 | E |
| 154 | E |
| 155 | C |
| 156 | D |
| 157 | C |
| 158 | A |
| 159 | B |
| 160 | B |
| 161 | B |
| 162 | B |
| 163 | C |
| 164 | C |
| 165 | C |
| 166 | C |
| 167 | B |
| 168 | A |
| 169 | E |
| 170 | A |

VWMD mutations were introduced into the genome of the HEK293T ATF4-Fluc stable cell lines by using GeneArt CRISPR nuclease vector with OFP Reporter kit (ThermoFisher; see Table 3 below). Guide RNAs were designed using the CRISPR Design Tool (http://crispr.mit.edu) and ligated into the CRISPR OFP Nuclease Vector. To obtain homology directed repair (HDR) incorporating VWMD point mutations in the genome, 150 bp ssDNA ultramer oligos were synthesized by Integrated DNA Technologies containing specific mutations of interest. In addition to the VWMD mutations, the ssDNA HDR templates contained a silent mutation to the PAM site of the CRISPR gRNA sequence (to avoid further Cas9 cutting) and 75 bp of homology on each side of the mutation.

HEK293T ATF4-Fluc cells were transfected with 500 ng of the CRISPR OFP Nuclease Vector and 1 uL of 10 μM ssDNA HDR template using lipofectamine 3000 (ThermoFisher) or SF Cell Line 4D-nucleofector X Kit (Lonza) according to the manufacturer's instructions. After 2-3 days of recovery, single cells were sorted for positive OFP expression on a FACS Aria II (BD Biosciences) into wells of a 96 well plate and allowed to recover for 1-2 weeks.

The resulting clones were surveyed for CRISPR editing and HDR by harvesting the genomic DNA with the PureLink Genomic DNA kit (ThermoFisher), amplifying a ~500 bp locus near the editing site, and sequencing the amplicon. Clones that displayed an ambiguous chromatogram signal near the expected CRISPR editing site were further examined by TA cloning (Invitrogen) and sequencing of the amplicon, yielding the sequence of each allele in the clone. Typical clones obtained were hemizygous for the VWMD point mutation, with one or two alleles harboring the desired mutation, and the remaining alleles knocked out (edited to produce a premature stop codon).

TABLE 3

Exemplary VWMD point mutations
introduced into eIF2B

| eIF2B Subunit | Mutation |
|---|---|
| eIF2B1 | V183F |
| eIF2B3 | H341Q |
| eIF2B3 | I346T |
| eIF2B4 | R483W |
| eIF2B5 | R113H |
| eIF2B5 | R195H |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:
1. A compound of Formula (I):

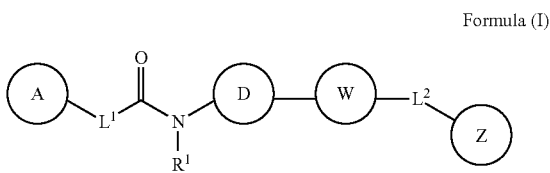

Formula (I)

or a pharmaceutically acceptable salt, solvate, hydrate, tautomer, or stereoisomer thereof, wherein:
D is

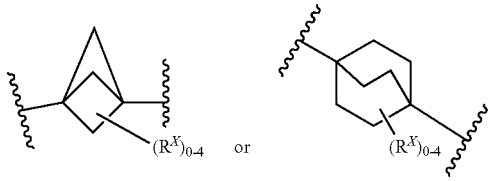

$L^1$ is $CH_2O$—* or $CH_2OCH_2$—*, $L^2$ is selected from $CH_2O$—*, $CH_2OCH_2$—*, or —O—, and "-*" indicates the attachment point to A or Z, respectively;
$R^1$ is hydrogen or $C_1$-$C_6$ alkyl;
A and W are each independently phenyl or 5-6-membered heteroaryl, wherein each phenyl or 5-6-membered heteroaryl is optionally substituted with 1-5 $R^Y$;
Z is hydrogen, phenyl, or 5-6-membered heteroaryl, wherein each phenyl or 5-6-membered heteroaryl is optionally substituted with 1-5 $R^Y$;
each $R^X$ is independently selected from the group consisting of $C_1$-$C_6$ alkyl, hydroxy-$C_1$-$C_6$ alkyl, halo-$C_1$-$C_6$ alkyl, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, —$SR^E$, —$S(O)R^D$, and —$S(O)_2R^D$;
each $R^Y$ is independently selected from the group consisting of hydrogen, $C_1$-$C_6$ alkyl, hydroxy-$C_1$-$C_6$ alkyl, halo-$C_1$-$C_6$ alkyl, halo-$C_1$-$C_6$ alkoxy, amino-$C_1$-$C_6$ alkyl, cyano-$C_1$-$C_6$ alkyl, oxo, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, —$S(R^F)_m$, —$S(O)R^D$, —$S(O)_2R^D$, and $G^1$; or
2 $R^Y$ groups on adjacent atoms, together with the atoms to which they are attached form a 3-7-membered fused cycloalkyl, 3-7-membered fused heterocyclyl, aryl, or 5-6 membered fused heteroaryl optionally substituted with 1-5 $R^X$;

each $G^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 $R^Z$;
each $R^Z$ is independently selected from the group consisting of $C_1$-$C_6$ alkyl, hydroxy-$C_1$-$C_6$ alkyl, halo-$C_1$-$C_6$ alkyl, halo, cyano, —$OR^A$, —$NR^BR^C$, —$NR^BC(O)R^D$, —$C(O)NR^BR^C$, —$C(O)R^D$, —$C(O)OH$, —$C(O)OR^D$, and —$S(O)_2R^D$;
$R^A$ is, at each occurrence, independently hydrogen, $C_1$-$C_6$ alkyl, halo-$C_1$-$C_6$ alkyl, —$C(O)NR^BR^C$, —$C(O)R^D$, —$C(O)OH$, or —$C(O)OR^D$;
each of $R^B$ and $R^C$ is independently hydrogen or $C_1$-$C_6$ alkyl; or
$R^B$ and $R^C$ together with the atom to which they are attached form a 3-7-membered heterocyclyl ring optionally substituted with 1-3 $R^Z$;
each $R^D$ is independently $C_1$-$C_6$ alkyl or halo-$C_1$-$C_6$ alkyl;
each $R^E$ is independently hydrogen $C_1$-$C_6$ alkyl, or halo-$C_1$-$C_6$ alkyl;
each $R^F$ is independently hydrogen, $C_1$-$C_6$ alkyl, or halo; and
m is 1, 3, or 5.
2. The compound of claim 1, wherein D is substituted with 0 $R^X$.
3. The compound of claim 1, wherein D is

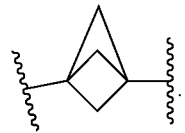 [SMILES: *C12CC(*)(C1)C2]

4. The compound of claim 1, wherein D is substituted with 1 $R^X$.
5. The compound of claim 4, wherein D is

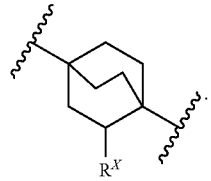

6. The compound of claim 5, wherein $R^X$ is oxo or OH.
7. The compound of claim 1, wherein $R^X$ is hydrogen.
8. The compound of claim 1, wherein A is phenyl, pyridyl, or isoxazolyl, each of which is optionally substituted with 1-2 $R^Y$ groups.
9. The compound of claim 1, wherein A is selected from:

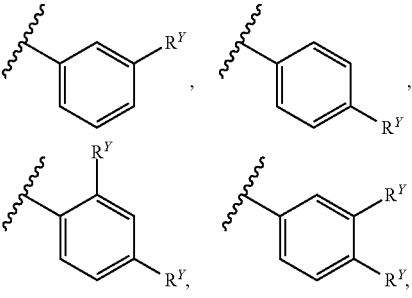

-continued

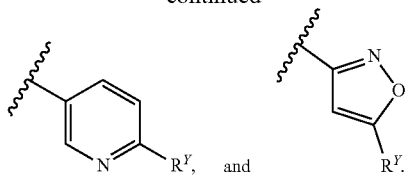

10. The compound of claim 1, wherein W is oxadiazolyl, imidazolyl, or triazolyl.

11. The compound of claim 1, wherein W is selected from:

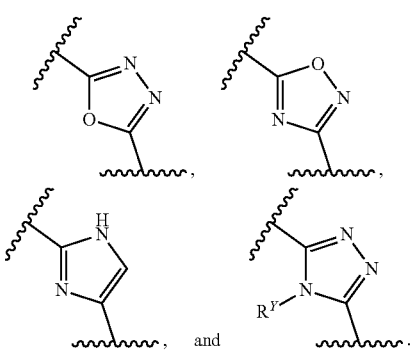

12. The compound of claim 1, wherein Z is phenyl or pyridyl, each of which is optionally substituted with 1-2 $R^Y$ groups.

13. The compound of claim 1, wherein Z is selected from:

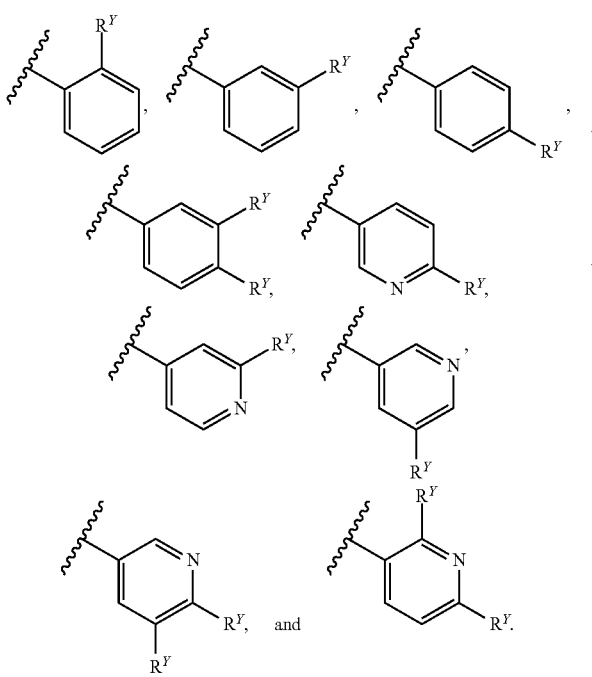

14. The compound of claim 1, wherein Z is hydrogen.

15. The compound of claim 1, wherein each $R^Y$ is independently selected from the group consisting of chloro, fluoro, $CF_3$, $CH_3$, $CH_2CH_3$, $CH(CH_3)_2$, $OCH_3$, $OCH(CH_3)_2$, CN, and $G^1$, wherein $G^1$ is cyclopropyl; or 2 $R^Y$ groups on adjacent atoms, together with the atoms to which they are attached, form a 3-7 membered fused heterocyclyl or 5-6 membered fused heteroaryl ring optionally substituted with 1-5 $R^X$.

16. The compound of claim 15, wherein the 2 $R^Y$ together with the atoms to which they are attached form a furanyl, pyrrolyl, or dioxolanyl ring, each of which is optionally substituted with 1-5 $R^X$.

17. The compound of claim 16, wherein each $R^X$ is independently fluoro.

18. A compound represented by Formula (I-a):

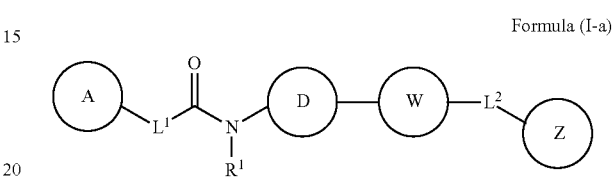

Formula (I-a)

or a pharmaceutically acceptable salt, solvate, hydrate, tautomer, or stereoisomer thereof, wherein:

D is bicyclo[1.1.1]pentanyl optionally substituted with 1-4 $R^X$ groups;

$L^1$ and $L^2$ are each independently $CH_2O$—*, $CH_2OCH_2$—*, or —O—, and "-*" indicates the attachment point to A or Z, respectively;

$R^1$ is hydrogen;

A and W are each independently phenyl, pyridyl, oxadiazolyl, imidazolyl, triazolyl, or isoxazolyl, each of which is optionally substituted with 1-5 $R^Y$ groups;

Z is hydrogen, phenyl, or pyridyl, wherein phenyl or pyridyl is optionally substituted with 1-5 $R^Y$ groups;

each $R^X$ is fluoro, oxo, or OH;

each $R^Y$ is independently chloro, fluoro, $CF_3$, $CH_3$, $CH_2CH_3$, $CH(CH_3)_2$, $OCH_3$, $OCH(CH_3)_2$, CN, or $G^1$; or 2 $R^Y$ groups on adjacent atoms, together with the atoms to which they are attached form a furanyl, pyrrolyl, or dioxolanyl ring, each of which is optionally substituted with 1-2 $R^X$; and $G^1$ is cyclopropyl.

19. A compound selected from the group consisting of:

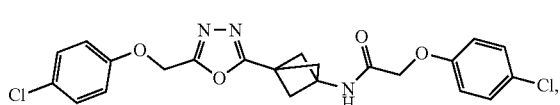

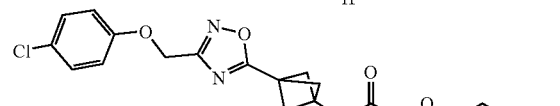

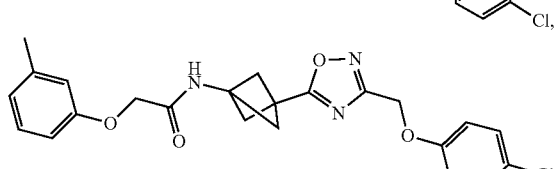

151
-continued
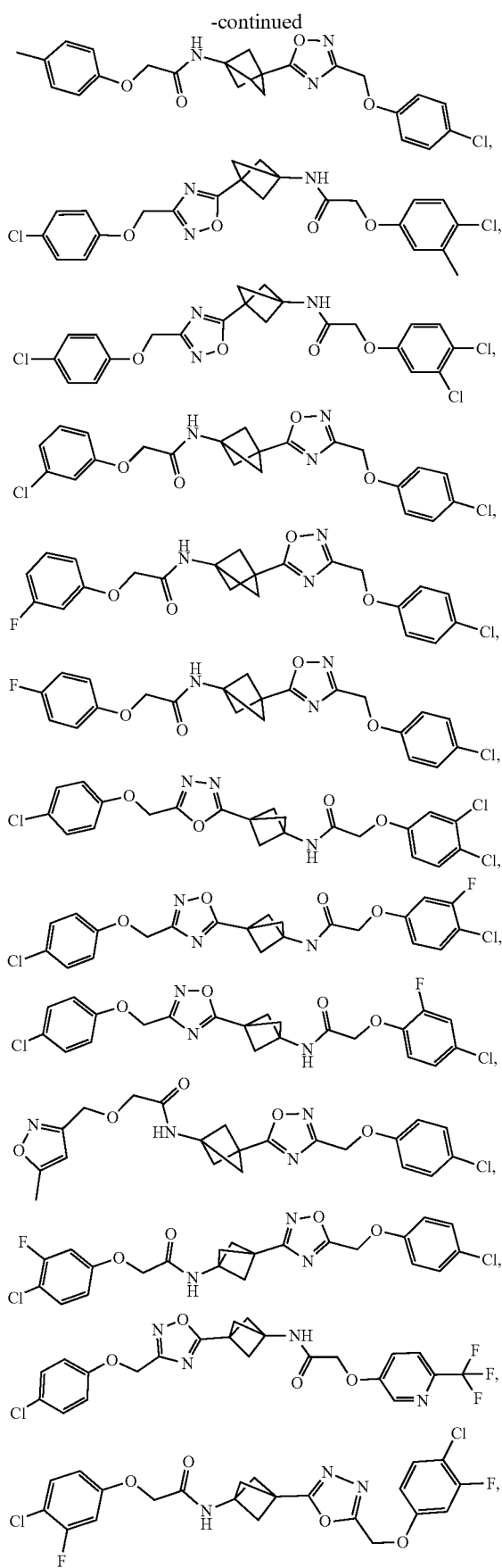
152
-continued
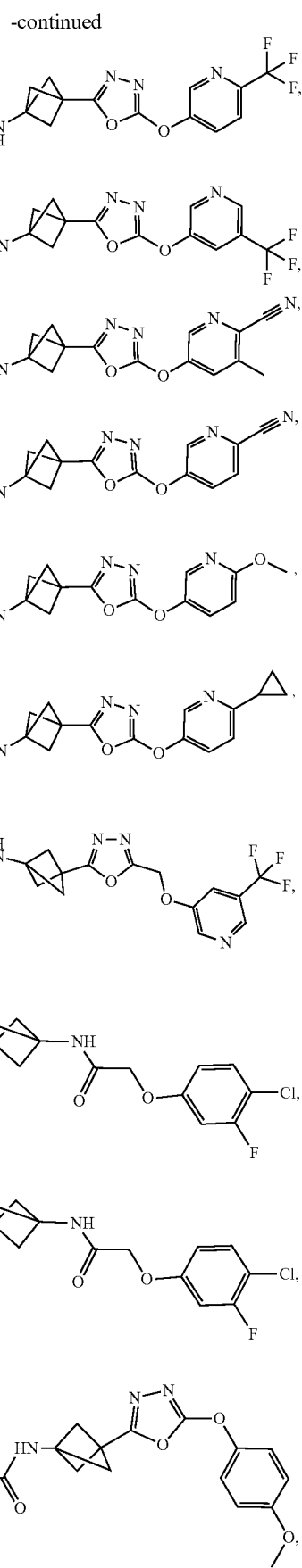

153
-continued
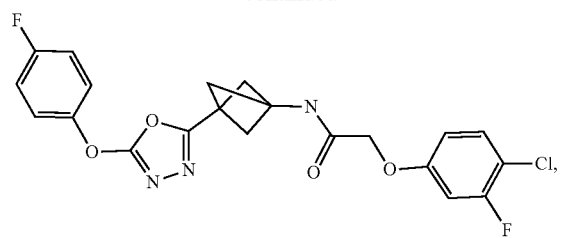
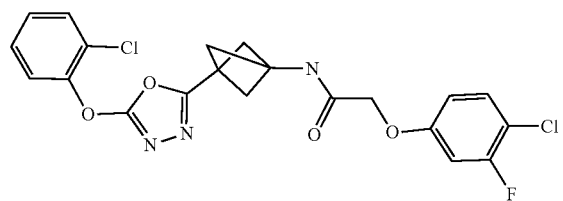
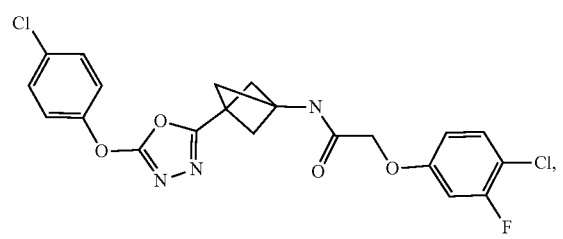
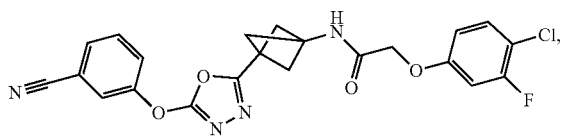
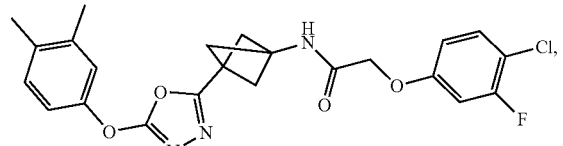
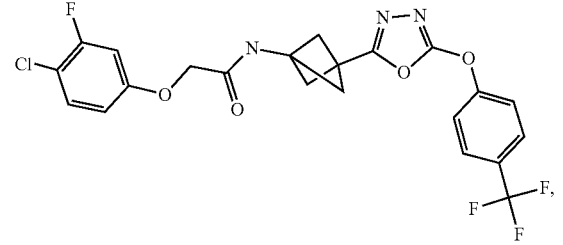
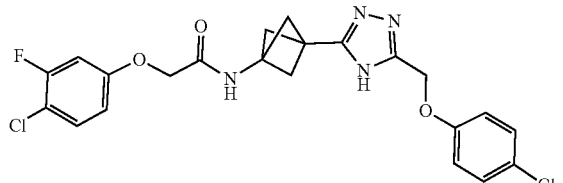
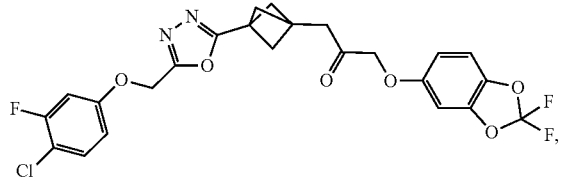
154
-continued
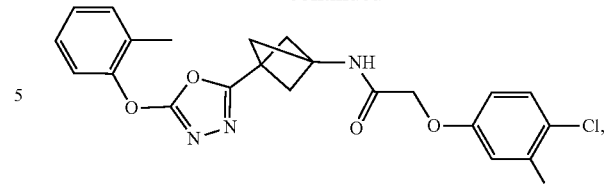
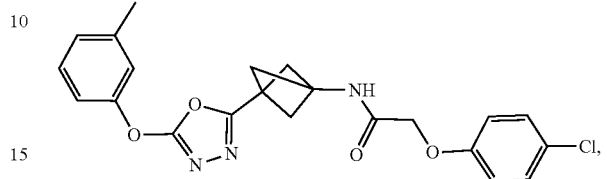
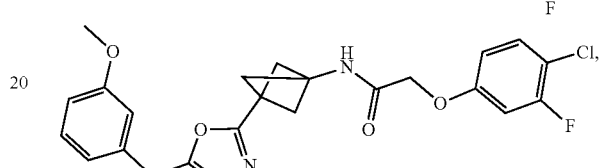
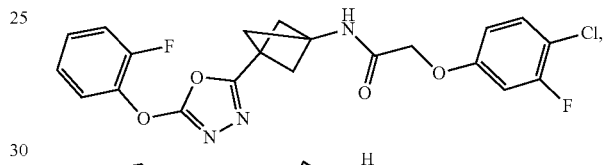
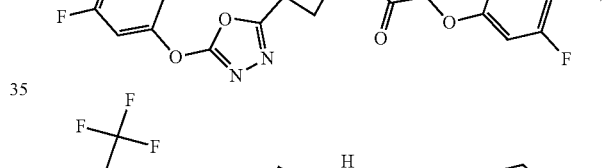
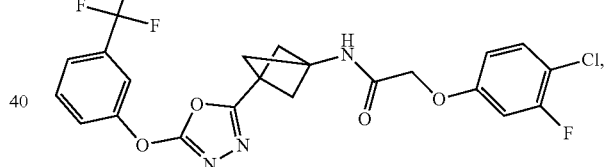
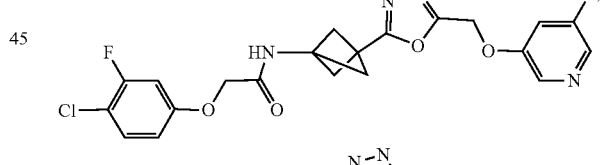
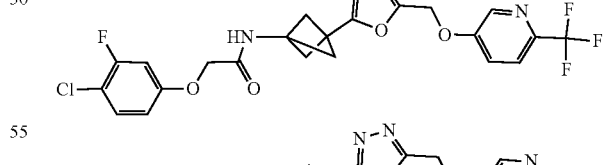
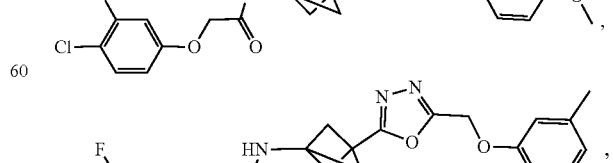
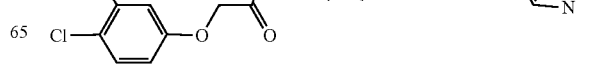

155
-continued
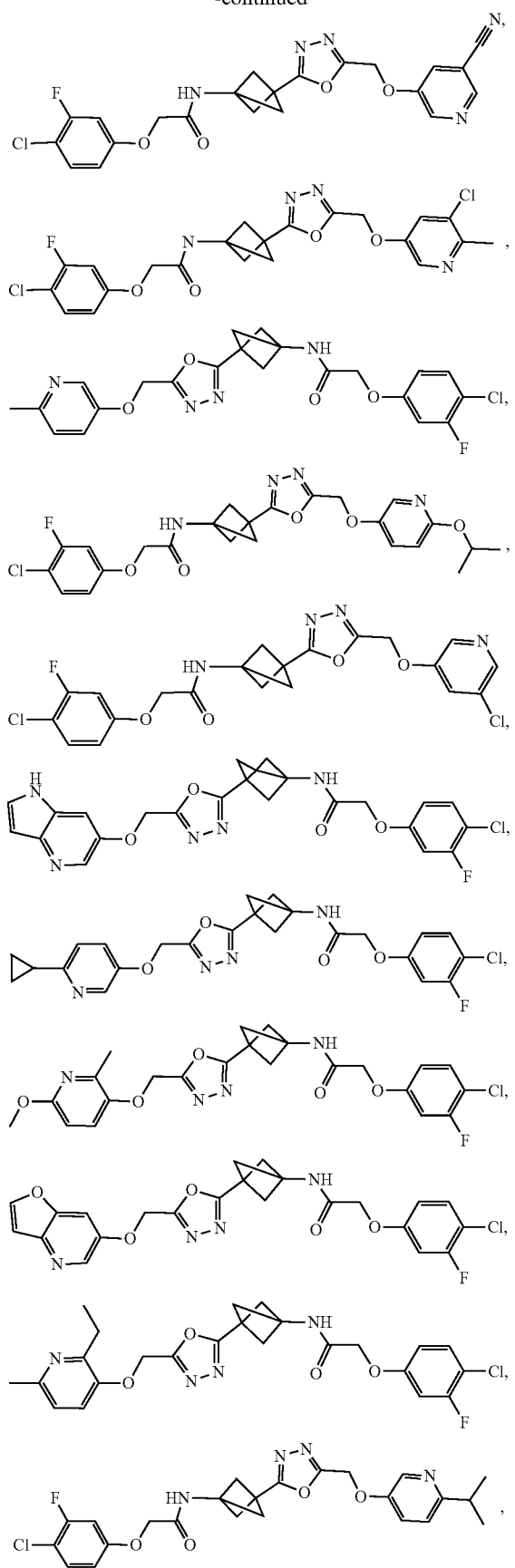
156
-continued
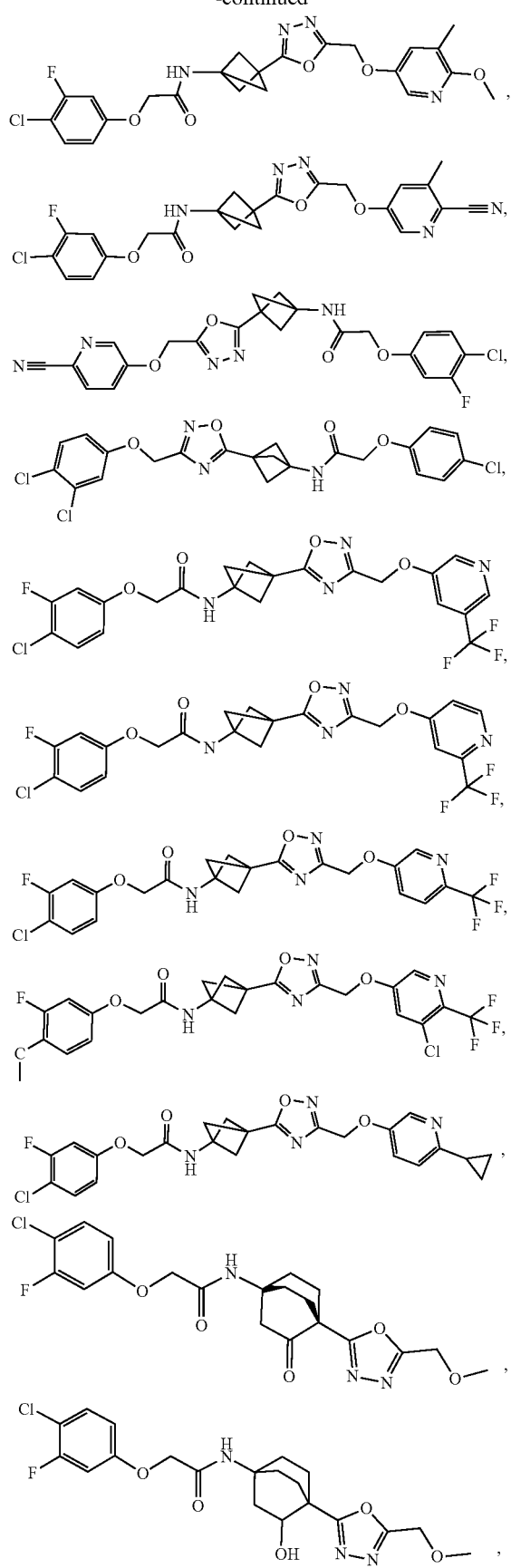

157
-continued

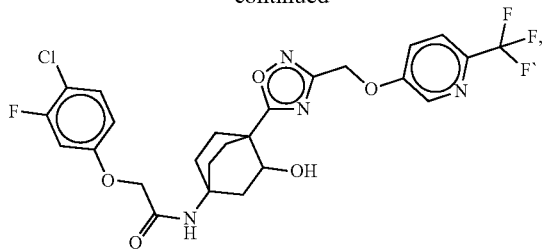

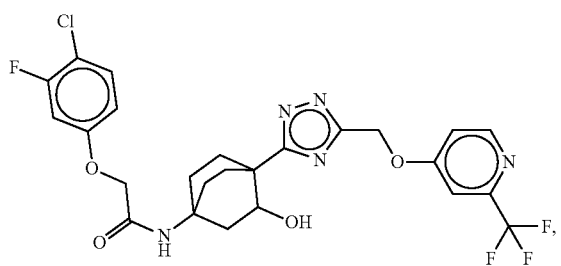

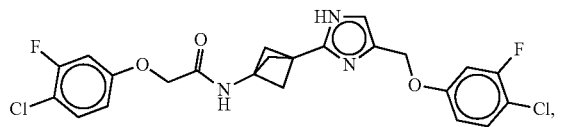

158
-continued

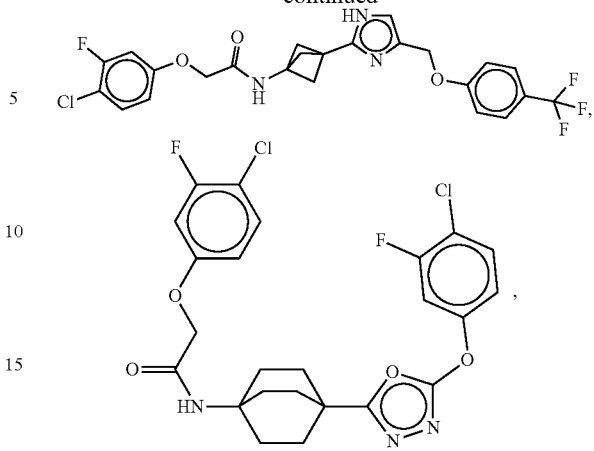

and a pharmaceutically acceptable salt thereof.

20. A pharmaceutically acceptable composition comprising a compound of claim 1 and a pharmaceutically acceptable carrier.

21. A composition for use in treating a neurodegenerative disease, a leukodystrophy, cancer, an inflammatory disease, a musculoskeletal disease, or a metabolic disease in a subject in need thereof, wherein the composition comprises a compound of claim 1 or a pharmaceutically acceptable salt, solvate, hydrate, tautomer, or stereoisomer thereof.

22. The composition of claim 21, further comprising a second agent, wherein the second agent is selected from the group consisting of an agent for treating a cancer, an agent for treating a neurodegenerative disease, an agent for treating a leukodystrophy, an agent for treating an inflammatory disease, an agent for treating a musculoskeletal disease, an agent for treating a metabolic disease, and an agent for treating a disease or disorder associated with impaired function of eIF2B, eIF2α, or a component of the eIF2 pathway or ISR pathway.

* * * * *